(12) United States Patent
Riebel et al.

(10) Patent No.: US 6,358,886 B1
(45) Date of Patent: Mar. 19, 2002

(54) 6-SUBSTITUTED 2,4-DIAMINO-1,3,5-TRIAZINE DERIVATIVES HAVING AT LEAST TWO ASYMMETRICALLY SUBSTITUTED CARBON ATOMS, THE PRODUCTION THEREOF, AND THEIR USE AS HERBICIDES

(75) Inventors: Hans-Jochem Riebel, Selters; Stefan Lehr, Langenfeld; Katharina Voigt, Monheim, all of (DE); Markus Dollinger, Overland Park, KS (US); Mark Wilhelm Drewes, Langenfeld; Ingo Wetcholowsky, Cond. Estancia Marambaia, both of (DE); Randy Allen Myers, Overland Park, KS (US); Yukiyoshi Watanabe, Oyama; Toshio Goto, Kokubunji-machi, both of (JP)

(73) Assignees: Bayer Aktienegesellschaft, Leverkusen (DE); Nihon Bayer Agrochem KK, Tokyo (JP)

(*) Notice: Subject to any disclaimer, the term of this patent is extended or adjusted under 35 U.S.C. 154(b) by 0 days.

(21) Appl. No.: 09/623,612
(22) PCT Filed: Feb. 26, 1999
(86) PCT No.: PCT/EP99/01234
§ 371 Date: Nov. 3, 2000
§ 102(e) Date: Nov. 3, 2000
(87) PCT Pub. No.: WO99/46249
PCT Pub. Date: Sep. 16, 1999

(30) Foreign Application Priority Data

Mar. 11, 1998 (DE) ............................... 198 10 394

(51) Int. Cl.⁷ ..................... C07D 251/18; A01N 43/68
(52) U.S. Cl. ..................... 504/232; 504/233; 544/206; 544/207
(58) Field of Search ............... 544/206, 207; 504/232, 233

(56) References Cited

U.S. PATENT DOCUMENTS 3,816,419 A  6/1974  Cross et al. ............. 260/249.9

(List continued on next page.)

FOREIGN PATENT DOCUMENTS

| DE | 2115318 | * 12/1971 |
| EP | 411 153 | 2/1991 |
| EP | 0 810 219 | 12/1997 |
| JP | 63/222166 | * 9/1988 |
| WO | 97/08156 | 8/1997 |
| WO | 97/29095 | 8/1997 |
| WO | 97/35481 | 10/1997 |
| WO | 98/15536 | 4/1998 |
| WO | 98/15537 | 4/1998 |
| WO | 98/15538 | 4/1998 |
| WO | 98/15539 | 4/1998 |
| WO | 98/34925 | 8/1998 |
| WO | 98/42684 | 10/1998 |
| WO | 99/18100 | 4/1999 |

OTHER PUBLICATIONS

Kelarev et al Chemical Abstracts vol. 120, entry 106941 U (1994).*
Eliel, "Stereo Chemistry of Carbon Compounds" pp. 92–95, Magraw Hill Book Co (1962).*

Primary Examiner—John M. Ford
(74) Attorney, Agent, or Firm—Joseph C. Gil

(57) ABSTRACT

The invention relates to novel substituted optically active aminotriazines having at least two asymmetrically substituted carbon atoms of the formula (I),

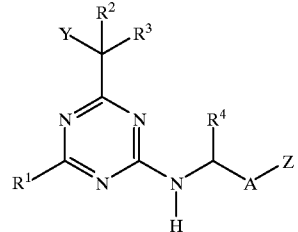

in which
A represents a single bond or represents in each case straight-chain or branched alkanediyl or oxaalkanediyl having in each case up to 6 carbon atoms,
Z represents certain carbocyclic or heterocyclic radicals and the substituents $R^1$, $R^2$, $R^3$, $R^4$ and Y are as defined in the description,
with the proviso that in each individual case $R^2$, $R^3$ and Y are different from one another and that the substituents at the two carbon atoms to which $R^2$ and $R^3$ or $R^4$ are attached are configured as follows:
(a) R configuration at the carbon atom to which $R^2$ and $R^3$ are attached and R configuration at the carbon atom to which $R^4$ is attached ("R,R-diastereomers"),
(b) R configuration at the carbon atom to which $R^2$ and $R^3$ are attached and S configuration at the carbon atom to which $R^4$ is attached ("R,S-diastereomers"),
(c) S configuration at the carbon atom to which $R^2$ and $R^3$ are attached and R configuration at the carbon atom to which $R^4$ is attached ("S,R-diastereomers"),
(d) S configuration at the carbon atom to which $R^2$ and $R^3$ are attached and S configuration at the carbon atom to which $R^4$ is attached ("S,S-diastereomers"),
(e) R configuration at the carbon atom to which $R^2$ and $R^3$ are attached and racemic configuration at the carbon atom to which $R^4$ is attached ("R,racdiastereomers"),
(f) S configuration at the carbon atom to which $R^2$ and $R^3$ are attached and racemic configuration at the carbon atom to which $R^4$ is attached ("S,rac-diastereomers"), and to a process for preparing the compounds of the formula (I) and to their use as herbicides.

8 Claims, No Drawings

U.S. PATENT DOCUMENTS

| | | |
|---|---|---|
| 3,932,167 A | 1/1976 | Cross et al. .................... 71/93 |
| 4,680,054 A | 7/1987 | Takematsu et al. ............ 71/93 |
| 4,844,731 A | 7/1989 | Takematsu et al. ............ 71/93 |
| 5,290,754 A | 3/1994 | Nishii et al. ................. 504/232 |
| 5,403,815 A | 4/1995 | Nishii et al. ................. 504/230 |
| 5,922,648 A | 7/1999 | Lorenz et al. ............... 504/232 |

* cited by examiner

6-SUBSTITUTED 2,4-DIAMINO-1,3,5-TRIAZINE DERIVATIVES HAVING AT LEAST TWO ASYMMETRICALLY SUBSTITUTED CARBON ATOMS, THE PRODUCTION THEREOF, AND THEIR USE AS HERBICIDES

This is a 371 National Application of PCT/EP99/01234, filed Feb. 26, 1999.

The invention relates to novel substituted, optically active aminotriazines having at least two asymmetrically substituted carbon atoms, to a process for their preparation and to their use as herbicides.

Substituted aminotriazines are already known from the (patent) literature (cf. U.S. Pat. No. 3,816,419, U.S. Pat. No. 3,932,167, EP-191 496, EP-273 328, EP-411 153/WO 90/09 378, WO 97/00 254, WO 97/08 156). However, these compounds—some of which also have asymmetrically substituted carbon atoms—have hitherto not attained any particular importance.

This invention, accordingly, provides the novel substituted, optically active aminotriazines having at least two asymmetrically substituted carbon atoms of the general formula (I)

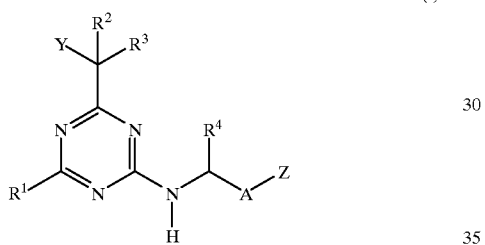

in which
- A represents a single bond or represents in each case straight-chain or branched alkanediyl or oxaalkanediyl having in each case up to 6 carbon atoms,
- $R^1$ represents amino, represents formylamino or represents in each case optionally cyano-, halogen- or $C_1$–$C_4$-alkoxy-substituted alkylamino, dialkylamino, alkylcarbonylamino, N-alkyl-N-alkylcarbonylamino, alkoxycarbonylamino, N-alkyl-N-alkoxycarbonylamino, alkylaminoalkylideneamino or dialkylaminoalkylideneamino having in each case up to 6 carbon atoms in the alkyl groups or alkylidene groups,
- $R^2$ represents hydrogen, halogen or optionally cyano-, halogen- or $C_1$–$C_4$-alkoxy-substituted alkyl having up to 6 carbon atoms,
- $R^3$ represents hydrogen, halogen or optionally cyano-, halogen- or $C_1$–$C_4$-alkoxy-substituted alkyl having up to 6 carbon atoms, or together with $R^2$ represents optionally cyano-, halogen- or $C_1$–$C_4$-alkyl-substituted alkanediyl having 2 to 5 carbon atoms,
- $R^4$ represents alkyl having up to 6 carbon atoms or represents cycloalkyl having 3 to 6 carbon atoms,
- Y represents hydrogen, hydroxyl, mercapto, amino, cyano, halogen, or represents in each case optionally cyano-, halogen- or $C_1$–$C_4$-alkoxy-substituted alkyl, alkoxy, alkylcarbonyloxy, alkoxycarbonyloxy, alkylaminocarbonyloxy, dialkylaminocarbonyloxy, alkylthio, alkylamino or dialkylamino having in each case up to 6 carbon atoms in the alkyl groups, and
- Z represents an optionally substituted monocyclic or bicyclic, carbocyclic or heterocyclic group from the group consisting of cyclopentyl, cyclohexyl, phenyl, naphthyl, tetralinyl, decalinyl, indanyl, indenyl, furyl, benzofuryl, di-hydrobenzofuryl, thienyl, benzothienyl, dihydrobenzothienyl, isobenzofuryl, dihydroisobenzofuryl, isobenzothienyl, dihydroisobenzothienyl, pyrrolyl, indolyl, isoindolyl, indolinyl, isoindolinyl, benzodioxolyl, oxazolyl, benzoxazolyl, thiazolyl, benzothiazolyl, benzimidazolyl, indazolyl, oxadiazolyl, thiadiazolyl, pyrazolyl, pyridinyl, pyrimidinyl, pyrazinyl, pyridazinyl, quinolyl, isoquinolyl, quinoxalinyl, cinnolinyl and phthalazinyl, where the possible substituents are in each case preferably selected from the group below:

hydroxyl, amino, cyano, nitro, carbamoyl, sulphamoyl, halogen, in each case optionally hydroxyl-, cyano- or halogen-substituted alkyl, alkoxy, alkylamino or dialkylamino having in each case 1 to 6 carbon atoms in the alkyl groups, in each case optionally halogen-substituted alkylcarbonyl, alkoxycarbonyl, alkylcarbonylamino, alkylaminocarbonyl, dialkylaminocarbonyl, alkylthio, alkylsulphinyl, alkylsulphonyl, alkylsulphonylamino, alkylaminosulphonyl or dialkylaminosulphonyl having in each case 1 to 6 carbon atoms in the alkyl groups, in each case optionally hydroxyl-, cyano-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl or phenoxy, and in each case optionally halogen-substituted methylenedioxy or ethylenedioxy, with the proviso that in each individual case $R^2$, $R^3$ and Y are different from one another and that the substituents at the two carbon atoms to which $R^2$ and $R^3$ or $R^4$ are attached are configured as follows:
- (a) R configuration at the carbon atom to which $R^2$ and $R^3$ are attached and R configuration at the carbon atom to which $R^4$ is attached ("R,R-diastereomers"),
- (b) R configuration at the carbon atom to which $R^2$ and $R^3$ are attached and S configuration at the carbon atom to which $R^4$ is attached ("R,S-diastereomers"),
- (c) S configuration at the carbon atom to which $R^2$ and $R^3$ are attached and R configuration at the carbon atom to which $R^4$ is attached ("S,R-diastereomers"),
- (d) S configuration at the carbon atom to which $R^2$ and $R^3$ are attached and S configuration at the carbon atom to which $R^4$ is attached ("S,S-diastereomers"),
- (e) R configuration at the carbon atom to which $R^2$ and $R^3$ are attached and racemic configuration at the carbon atom to which $R^4$ is attached ("R,rac-diastereomers"),
- (f) S configuration at the carbon atom to which $R^2$ and $R^3$ are attached and racemic configuration at the carbon atom to which $R^4$ is attached ("S,rac-diastereomers").

Since the C atom to which $R^2$, $R^3$ and Y are attached is not present in racemic form, all compounds according to the invention are optically active.

The novel substituted aminotriazines having at least two asymmetrically substituted carbon atoms of the general formula (I) are obtained when substituted biguanides of the general formula (II)

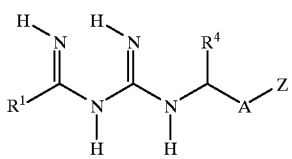

(II)

in which
A, $R^1$, $R^4$ and Z are as defined above,
—and/or acid adducts of compounds of the general formula (II)— are reacted with (optically active) carboxylic acid derivatives of the general formula (III)

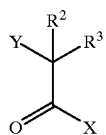

(III)

in which
$R^2$, $R^3$ and Y are as defined above and
X represents halogen or alkoxy,
if appropriate in the presence of a reaction auxiliary and if appropriate in the presence of a diluent,
and, if appropriate, further conversions within the scope of the above definition of the substituents are carried out by customary methods on the resulting compounds of the general formula (I).

The compounds of the general formula (I) can be converted by customary methods into other compounds of the general formula (I) according to the above definition of the substituents, for example by acylation of compounds of the formula (I) in which $R^1$ represents amino and/or Y represents hydroxyl, for example using acetyl chloride or propionyl chloride, or, for example, by fluorination of compounds of the formula (I) in which Y represents hydroxyl, for example using diethylaminosulphur tri-fluoride ("DAST")—cf. the Preparation Examples.

The novel substituted aminotriazines having at least two asymmetrically substituted carbon atoms of the general formula (I) have strong and selective herbicidal activity. To a certain extent, they also have fungicidal and insecticidal activity.

In the definitions, the hydrocarbon chains, such as in alkyl, are in each case straight-chain or branched—including in combination with heteroatoms, such as in alkoxy or alkylthio.

Halogen generally represents fluorine, chlorine, bromine or iodine, preferably represents fluorine, chlorine or bromine, in particular represents fluorine or chlorine.

The invention preferably provides compounds of the formula (I), in which

A represents a single bond, represents methylene (—$CH_2$—), dimethylene (ethane-1,2-diyl, —$CH_2CH_2$—), ethylidene (ethane-1,1-diyl, —CH($CH_3$,)—), oxaethanediyl (—$CH_2O$—), trimethylene (propane-1,3-diyl, —$CH_2CH_2CH_2$—), propylidene (propane-1,1-diyl, —CH($C_2H_5$)—), propane-2,3-diyl (—CH($CH_3$)$CH_2$—), 2-methylpropane-1,3-diyl (—$CH_2$CH($CH_3$)$CH_2$—), 3-oxapropane-1,3-diyl (—$CH_2CH_2O$—), 2-oxapropane-1,3-diyl (—$CH_2OCH_2$—), tetramethylene (butane-1,4-diyl, —$CH_2CH_2CH_2CH_2$—), butane-2,4-diyl (—CH($CH_3$)$CH_2CH_2$—), butane-2,3-diyl (—CH($CH_3$)CH($CH_3$)—), 3-methylbutane-2,4-diyl (—CH($CH_3$)CH($CH_3$)$CH_2$—), 4-oxabutane-2,4-diyl (—CH($CH_3$)$CH_2O$—), pentane-3,5-diyl (—CH($C_2H_5$)$CH_2CH_2$—), 5-oxa-pentane-3,5-diyl (—CH($C_2H_5$)$CH_2O$—), 4-oxapentane-2,5-diyl (—CH($CH_3$)$CH_2OCH_2$—) or 5-oxahexane-3,6-diyl (—CH($C_2H_5$)$CH_2OCH_2$), $R^1$ represents amino, represents formylamino or represents in each case optionally cyano-, fluorine-, chlorine-, methoxy- or ethoxy-substituted methylamino, ethylamino, dimethylamino, acetylamino, propionylamino, n- or i-butyroylamino, N-methyl-N-acetylamino, N-ethyl-N-acetylamino, N-methyl-N-propionylamino, methoxycarbonylamino, ethoxycarbonylamino, n- or i-propoxycarbonylamino, N-methyl-N-methoxycarbonylamino, N-ethyl-N-methoxycarbonylamino, N-methyl-N-ethoxycarbonylamino, methylaminomethyleneamino, ethylaminomethyleneamino, methylaminoethylideneamino or dimethylaminomethyleneamino, $R^2$ represents hydrogen, fluorine, chlorine, bromine, or in each case optionally cyano-, fluorine-, chlorine-, methoxy- or ethoxy-substituted methyl, ethyl, n- or i-propyl, n-, i-, s- or t-butyl, $R^3$ represents hydrogen, fluorine, chlorine, bromine, or in each case optionally cyano-, fluorine-, chlorine, methoxy- or ethoxy-substituted methyl, ethyl, n- or i-propyl, n-, i-, s- or t-butyl, or together with $R^2$ represents in each case optionally cyano-, fluorine-, chlorine-, bromine-, methyl- or ethyl-substituted dimethylene (ethane-1,2-diyl), trimethylene (propane-1,3-diyl) or tetramethylene (butane-1,4-diyl), $R^4$ represents methyl, ethyl, n- or i-propyl, or represents cyclopropyl, Y represents hydrogen, hydroxyl, mercapto, amino, cyano, fluorine, chlorine, bromine, or represents in each case optionally cyano-, fluorine-, chlorine-, methoxy- or ethoxy-substituted methyl, ethyl, n- or i-propyl, n-, i- or s-butyl, methoxy, ethoxy, n- or i-propoxy, n-, i- or s-butoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, dimethylaminocarbonyloxy, methylthio, ethylthio, n- or i-propylthio, n-, i- or s-butylthio, methylamino, ethylamino, n- or i-propylamino, n-, i- or s-butylamino or dimethylamino, and Z represents an optionally substituted monocyclic or bicyclic, carbocyclic or heterocyclic grouping from the group consisting of cyclohexyl, phenyl, naphthyl, tetralinyl, decalinyl, indanyl, indenyl, furyl, benzofuryl, dihydrobenzofuryl, thienyl, benzothienyl, dihydrobenzothienyl, isobenzofuryl, dihydroisobenzofuryl, isobenzothienyl, dihydroisobenzothienyl, pyrrolyl, indolyl, isoindolyl, indolinyl, isoindolinyl, benzodioxolyl, oxazolyl, benzoxazolyl, thiazolyl, benzothiazolyl, benzimidazolyl, indazolyl, oxadiazolyl, thiadiazolyl, pyrazolyl, pyridinyl, pyrimidinyl, pyrazinyl, pyridazinyl, quinolyl, isoquinolyl, quinoxalinyl, cinnolinyl and phthalazinyl, where the possible substituents are in each case preferably selected from the group below:
hydroxyl, amino, cyano, nitro, carbamoyl, sulphamoyl, fluorine, chlorine, bromine, in each case optionally hydroxyl-, cyano-, fluorine- or chlorine-substituted methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i-, s- or t-butylamino or dimethylamino, in each case optionally fluorine- and/or chlorine-substituted acetyl, propionyl, n- or i-butyroyl, methoxycarbonyl, ethoxycarbonyl, n- or i-propoxycarbonyl, acetylamino, propionylamino, n- or i-butyroylaminio, methylaminocarbonyl, ethylaminocarbonyl, n- or i-propylaminocarbonyl, dimethylaminocarbonyl, methylthio, ethylthio, n- or i-propylthio, n-, i-, s- or t-butylthio, methylsulphinyl, ethyl-sulphinyl, n- or i-propylsulphinyl, methylsulphonyl, ethylsulphonyl, n- or i-propylsulphonyl, methylsulphonylamino, ethylsulphonylamino, n- or i-propylsulphonylamino, methylaminosulphonyl, ethylaminosulphonyl, n- or i-propylaminosulphonyl, or dimethylaminosulphonyl, in each case optionally hydroxyl-, cyano-, nitro-, fluorine-, chlorine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substiuted phenyl or phenoxy, and in each case optionally fluorine- and/or chlorine-substituted methylenedioxy or ethylenedioxy, with the proviso that in each individual case $R^2$, $R^3$ and Y are different from one another and that the substituents at the carbon atoms to which $R^2$ and $R^3$ or $R^4$ are attached are configured as follows:

(a) R configuration at the carbon atom to which $R^2$ and $R^3$ are attached and R configuration at the carbon atom to which $R^4$ is attached ("R,R-diastereomers"), (b) R configuration at the carbon atom to which $R^2$ and $R^3$ are attached and S configuration at the carbon atom to which $R^4$ is attached ("R,S-diastereomers"), (c) S configuration at the carbon atom to which $R^2$ and $R^3$ are attached and R configuration at the carbon atom to which $R^4$ is attached ("S,R-diastereomers"), (d) S configuration at the carbon atom to which $R^2$ and $R^3$ are attached and S configuration at the carbon atom to which $R^4$ is attached ("S,S-diastereomers"), (e) R configuration at the carbon atom to which $R^2$ and $R^3$ are attached and racemic configuration at the carbon atom to which $R^4$ is attached ("R,rac-diastereomers"), (f) S configuration at the carbon atom to which $R^2$ and $R^3$ are attached and racemic configuration at the carbon atom to which $R^4$ is attached ("S,rac-diastereomers").

The invention relates in particular to compounds of the formula (I), in which

A represents a single bond, represents dimethylene (ethane-1,2-diyl, —CH$_2$CH$_2$—), oxaethanediyl (—CH$_2$O—) or 2-oxapropane-1,3-diyl (—CH$_2$OCH$_2$—), $R^1$ represents amino, represents formylamino or represents in each case optionally cyano-, fluorine-, chlorine-, methoxy- or ethoxy-substituted acetylamino, propionylamino, methoxycarbonylamino, ethoxycarbonylamino, or di-methylaminomethyleneamino, $R^2$ represents hydrogen, fluorine, chlorine, or in each case optionally cyano-, fluorine-, chlorine-, methoxy- or ethoxy-substituted methyl, ethyl, n- or i-propyl, $R^3$ represents hydrogen, fluorine, chlorine, bromine, or in each case optionally cyano-, fluorine-, chlorine-, methoxy- or ethoxy-substituted methyl, ethyl, n- or i-propyl, or together with $R^2$ represents in each case optionally cyano-, fluorine-, chlorine- or methyl-substituted dimethylene (ethane-1,2-diyl), $R^4$ represents methyl or ethyl, Y represents hydrogen, hydroxyl, cyano, fluorine, chlorine, bromine, or represents in each case optionally cyano-, fluorine-, chlorine-, methoxy- or ethoxy-substituted methyl, ethyl, n- or i-propyl, methoxy, ethoxy, n- or i-propoxy, acetyloxy, propionyloxy, methoxycarbonyloxy, ethoxycarbonyloxy, methylaminocarbonyloxy, ethylaminocarbonyloxy or dimethylaminocarbonyloxy, and Z represents an optionally substituted monocyclic or bicyclic, carbocyclic or heterocyclic grouping from the group consisting of phenyl, naphthyl, tetralinyl, decalinyl, indanyl, indenyl, furyl, benzofuryl, dihydrobenzofuryl, thienyl, benzothienyl, dihydrobenzothienyl, isobenzofuryl, dihydroisobenzofuryl, isobenzothienyl, dihydroisobenzothienyl, pyrrolyl, indolyl, isoindolyl, indolinyl, isoindolinyl, benzodioxolyl, oxazolyl, benzoxazolyl, thiazolyl, benzothiazolyl, benzimidazolyl, indazolyl, pyrazolyl, pyridinyl, pyrimidinyl, pyrazinyl, pyridazinyl, quinolyl, isoquinolyl, quinoxalinyl, cinnolinyl and phthalazinyl, where the possible substituents are in each case preferably selected from the group below:

hydroxyl, amino, cyano, nitro, carbamoyl, sulphamoyl, fluorine, chlorine, bromine, in each case optionally hydroxyl-, cyano-, fluorine- or chlorine-substituted methyl, ethyl, n- or i-propyl, n-, i-, s- or t-butyl, methoxy, ethoxy, n- or i-propoxy, dimethylamino, in each case optionally fluorine- and/or chlorine-substituted acetyl, methoxycarbonyl, ethoxycarbonyl, dimethylaminocarbonyl, methylthio, ethylthio, n- or i-propylthio, methylsulphinyl, ethylsulphinyl, methylsulphonyl, ethylsulphonyl or dimethylaminosulphonyl, in each case optionally hydroxyl-, cyano-, nitro-, fluorine-, chlorine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl or phenoxy, and in each case optionally fluorine- and/or chlorine-substituted methylenedioxy or ethylenedioxy, with the proviso that in each individual case $R^2$, $R^3$ and Y are different from one another and that the substituents at the carbon atoms to which $R^2$ and $R^3$ or $R^4$ are attached are configured as follows:

(a) R configuration at the carbon atom to which $R^2$ and $R^3$ are attached and R configuration at the carbon atom to which $R^4$ is attached ("R,R-diastereomers"), (b) R configuration at the carbon atom to which $R^2$ and $R^3$ are attached and S configuration at the carbon atom to which $R^4$ is attached ("R,S-diastereomers"), (c) S configuration at the carbon atom to which $R^2$ and $R^3$ are attached and R configuration at the carbon atom to which $R^4$ is attached ("S,R-diastereomers"), (d) S configuration at the carbon atom to which $R^2$ and $R^3$ are attached and S configuration at the carbon atom to which $R^4$ is attached ("S,S-diastereomers").

The abovementioned general or preferred radical definitions apply both to the end products of the formula (I) and correspondingly to the starting materials or intermediates required in each case for the preparation. These radical definitions can be combined with one another as desired, i.e. including combinations between the given preferred ranges.

Examples of the compounds of the general formula (I) according to the invention are listed in the groups below.

Group I

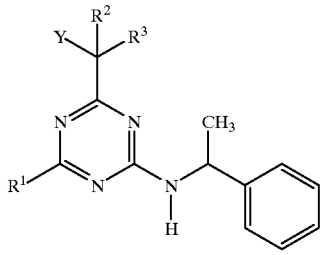

Here, $R^1$ represents, for example, amino, formylamino, acetylamino, propionylamino or dimethylaminomethyleneamino.

Here, the triazine substituent with $R^2$, $R^3$ and Y represents, for example, the groupings below:

—CH(CH$_3$)C$_2$H$_5$, —CH(CH$_3$)C$_3$H$_7$-n, —CH(CH$_3$)C$_3$H$_7$-i, —CH(C$_2$H$_5$)C$_3$H$_7$-n, —CH(C$_2$H$_5$)C$_3$H$_7$-i, —C(CH$_3$)(C$_2$H$_5$)C$_3$H$_7$-n, —C(CH$_3$)(C$_2$H$_5$)C$_3$H$_7$-i, —CH(OH)CH$_3$, —CH(OH)C$_2$H$_5$, —CH(OH)C$_3$H$_7$-n, —CH(OH)C$_3$H$_7$-i, —CH(OCHO)CH$_3$, —CH(OCHO)C$_2$H$_5$, —CH(OCHO)C$_3$H$_7$-n, —CH(OCHO)C$_3$H$_7$-i, —CH(OCOCH$_3$)CH$_3$, —CH(OCOCH$_3$)C$_2$H$_5$, —CH(OCOCH$_3$)C$_3$H$_7$-n, —CH(OCOCH$_3$)C$_3$H$_7$-i, —CH(OCOC$_2$H$_5$)CH$_3$, —CH(OCOC$_3$H$_7$-n)CH$_3$, —CH(OCOC$_3$H$_7$-i)CH$_3$, —C(OH)(CH$_3$)C$_2$H$_5$, —C(OH)(CH$_3$)C$_3$H$_7$-n, —C(OH)(CH$_3$)C$_3$H$_7$-i, —CH(SH)CH$_3$, —CHBrCH$_3$, —CHBrC$_2$H$_5$, —CHBrC$_3$H$_7$-n, —CHBrC$_3$H$_7$-i, —CBrCH$_3$)C$_2$H$_5$, —CBrCH$_3$)C$_3$H$_7$-n, —CBr(CH$_3$)C$_3$H$_7$-i, —CHClCH$_3$, —CHClC$_2$H$_5$, —CHClC$_3$H$_7$-n, —CHClC$_3$H$_7$-i, —CCl(CH$_3$)C$_2$H$_5$, —CCl(CH$_3$)C$_3$H$_7$-n, —CCl(CH$_3$)C$_3$H$_7$-i, —CHFCH$_3$, —CHFC$_2$H$_5$, —CHFC$_3$H$_7$-n, —CHFC$_3$H$_7$-i, —CF(CH$_3$)C$_2$H$_5$, —CF(CH$_3$)C$_3$H$_7$-n, —CF(CH$_3$)C$_3$H$_7$-i, —CH(CF$_3$)CH$_3$, —CH(CF$_3$)C$_2$H$_5$, —CH(CF$_3$)C$_3$H$_7$-n, —CH(CF$_3$)C$_3$H$_7$-i, —C(CF$_3$)(CH$_3$)C$_2$H$_5$, —C(CF$_3$)(CH$_3$)C$_3$H$_7$-n, —C(CF$_3$)(CH$_3$)C$_3$H$_7$-i, —CH(OH)CF$_3$, —C(OH)(CF$_3$)CH$_3$, —CF(OH)CF$_3$, —CH(CH$_3$)OCH$_3$, —CH(C$_2$H$_5$)OCH$_3$, —CH(C$_3$H$_7$-n)OCH$_3$, —CH(C$_3$H$_7$-i)OCH$_3$, —C(CH$_3$)(C$_2$H$_5$)OCH$_3$, —C(CH$_3$)(C$_3$H$_7$-n)OCH$_3$, —C(CH$_3$)(C$_3$H$_7$-i)OCH$_3$, —CH(CH$_3$)OC$_2$H$_5$, —CH(C$_2$H$_5$)OC$_2$H$_5$, —CH(C$_3$H$_7$-n)OC$_2$H$_5$, —CH(C$_3$H$_7$-i)OC$_2$H$_5$, —CH(CH$_3$)OC$_3$H$_7$-n, —CH(CH$_3$)OC$_3$H$_7$-i, —CH(C$_2$H$_5$)OC$_3$H$_7$-n, —CH(C$_2$H$_5$)OC$_3$H$_7$-i, —CH(CF$_3$)OCH$_3$, —CH(CF$_3$)OC$_2$H$_5$, —CHFCF$_3$, —CHClCF$_3$, —CF(CH$_3$)CF$_3$, —CF(C$_2$H$_5$)CF$_3$, —CF(C$_3$H$_7$-n)CF$_3$, —CF(C$_3$H$_7$-i)CF$_3$, —CH(CN)CH$_3$, —CH(CN)C$_2$H$_5$, —CH(CN)C$_3$H$_7$-n, —CH(CN)C$_3$H$_7$-i, —C(CN)(CH$_3$)C$_2$H$_5$, —C(CN)(CH$_3$)C$_3$H$_7$-n, —C(CN)(CH$_3$)C$_3$H$_7$-n, —CH(CH$_3$)SCH$_3$, —CH(C$_2$H$_5$)SCH$_3$, —CH(C$_3$H$_7$-n)SCH$_3$, —CH(C$_3$H$_7$-i)SCH$_3$, —C(CH$_3$)(C$_2$H$_5$)SCH$_3$, —C(CH$_3$)(C$_3$H$_7$-n)SCH$_3$, —C(CH$_3$)(C$_3$H$_7$-i)SCH$_3$, —CH(CH$_3$)SC$_2$H$_5$, —CH(C$_2$H$_5$)SC$_2$H$_5$, —CH(C$_3$H$_7$-n)SC$_2$H$_5$, —CH(C$_3$H$_7$-i)SC$_2$H$_5$, —CHFBr, —CHFCl, —CFBrCH$_3$, —CFClCH$_3$, —CFBrCl, —CH(CH$_2$Cl)Cl, —CH(CH$_3$)CH$_2$OCH$_3$, —CH(CH$_3$)CH$_2$OC$_2$H$_5$, —CH(C$_2$H$_5$)CH$_2$OCH$_3$, —CH(CH$_3$)CH$_2$CH$_2$OCH$_3$,

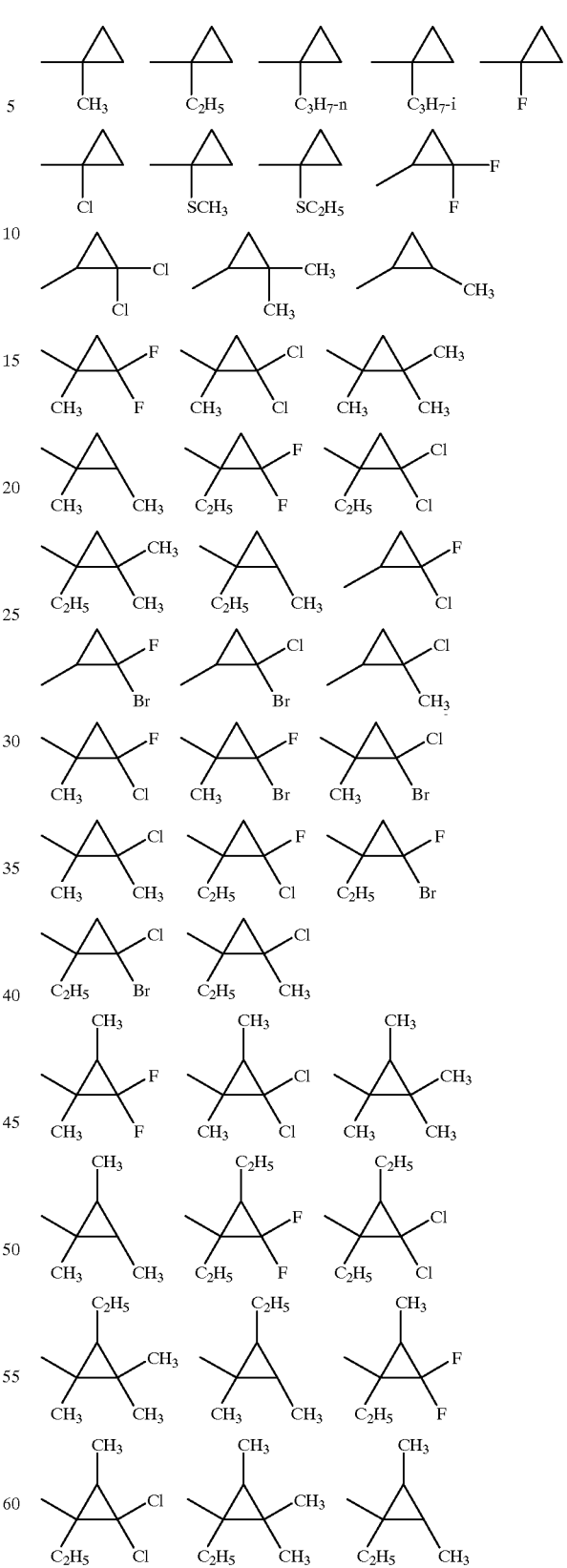

For each of the examples listed here and in the groups below by formulae and radical definitions, particular emphasis is given to the diastereomeric forms described below:

(a) R configuration at the carbon atom to which $R^2$ and $R^3$ are attached and R configuration at the carbon atom to which $R^4$ is attached ("R,R-diastereomers"), (b) R configuration at the carbon atom to which $R^2$ and $R^3$ are attached and S configuration at the carbon atom to which $R^4$ is attached ("R,S-diastereomers"), (c) S configuration at the carbon atom to which $R^2$ and $R^3$ are attached and R configuration at the carbon atom to which $R^4$ is attached ("S,R-diastereomers"), (d) S configuration at the carbon atom to which $R^2$ and $R^3$ are attached and S configuration at the carbon atom to which $R^4$ is attached ("S,S-diastereomers").

Group 2

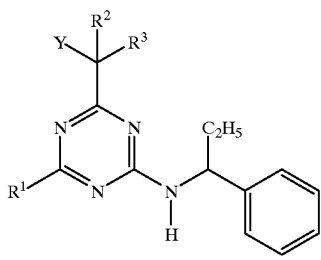

Here, $R^1$, $R^2$, $R^3$ and Y have, for example, the meanings given above in group 1.

Group 3

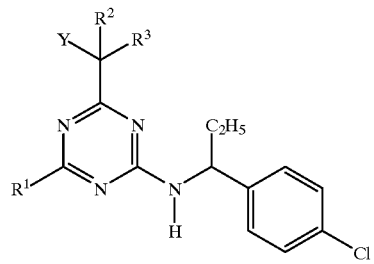

Here, $R^1$, $R^2$, $R^3$ and Y have, for example, the meanings given above in group I.

Group 4

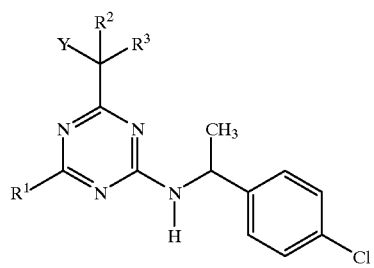

Here, $R^1$, $R^2$, $R^3$ and Y have, for example, the meanings given above in group 1.

Group 5

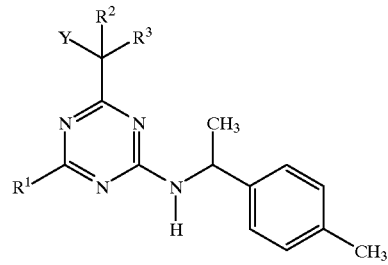

Here, $R^1$, $R^2$, $R^3$ and Y have, for example, the meanings given above in group 1.

Group 6

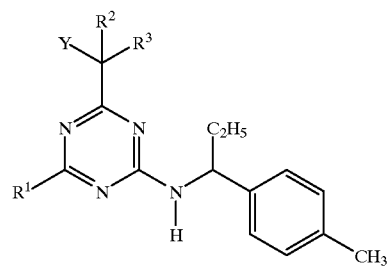

Here, $R^1$, $R^2$, $R^3$ and Y have, for example, the meanings given above in group 1.

Group 7

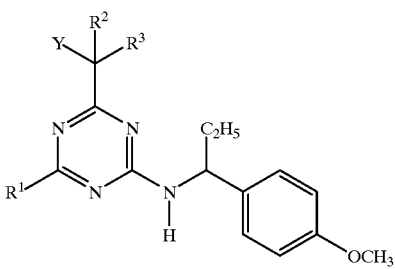

Here, $R^1$, $R^2$, $R^3$ and Y have, for example, the meanings given above in group 1.

Group 8

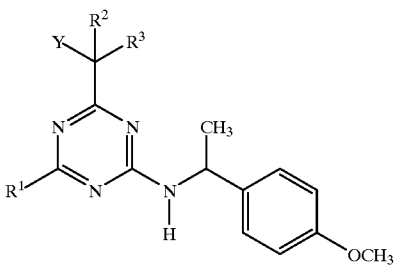

Here, $R^1$ $R^2$, $R^3$ and Y have, for example, the meanings given above in group 1.

Group 9

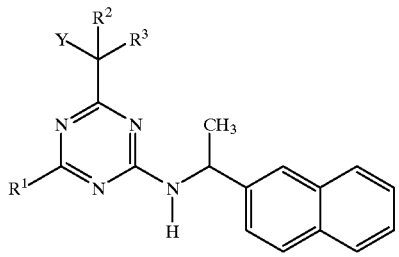

Here, $R^1$, $R^2$, R and Y have, for example, the meanings given above in group 1.

Group 10

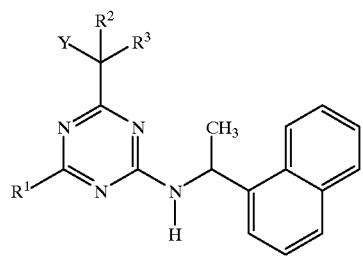

Here, $R^1$, $R^2$, $R^3$ and Y have, for example, the meanings given above in group 1.

Group 11

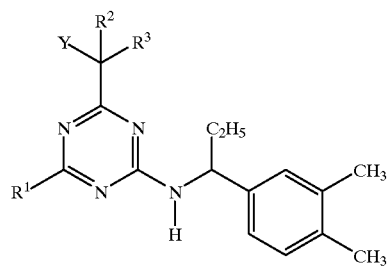

Here, $R^1$, $R^2$, $R^3$ and Y have, for example, the meanings given above in group 1.

Group 12

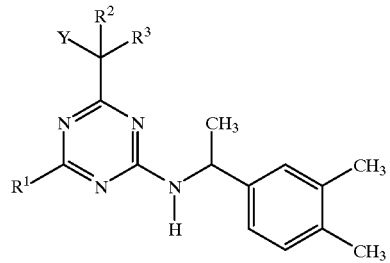

Here, $R^1$, $R^2$, $R^3$ and Y have, for example, the meanings given above in group 1.

Group 13

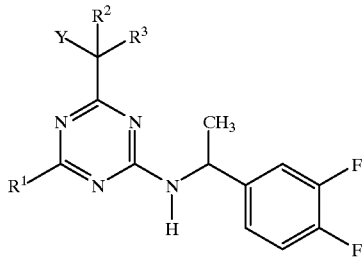

Here, $R^1$, $R^2$, $R^3$ and Y have, for example, the meanings given above in group 1.

Group 13a

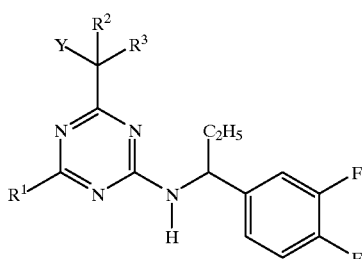

Here, $R^1$, $R^2$, $R^3$ and Y have, for example, the meanings given above in group 1.

Group 14

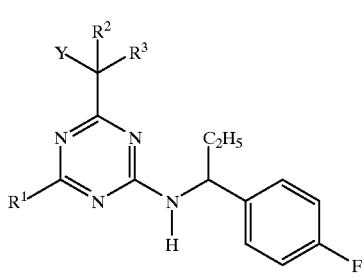

Here, $R^1$, $R^2$, $R^3$ and Y have, for example, the meanings given above in group 1.

Group 15

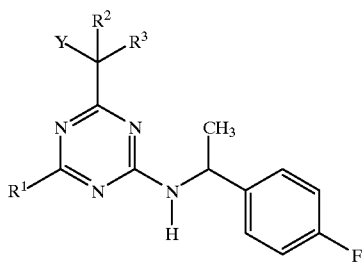

Here, $R^1$, $R^2$, $R^3$ and Y have, for example, the meanings given above in group 1.

Group 16

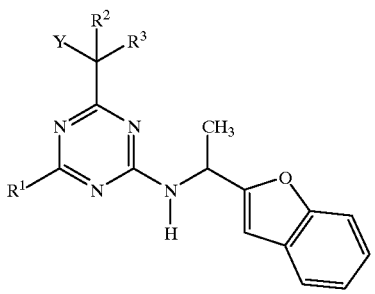

Here R$^1$, R$^2$, R$^3$ and Y have, for example, the meanings given above in group 1.

Group 17

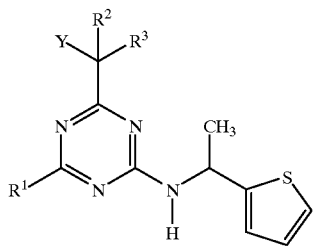

Here, R$^1$, R$^2$, R$^3$ and Y have, for example, the meanings given above in group 1.

Group 18

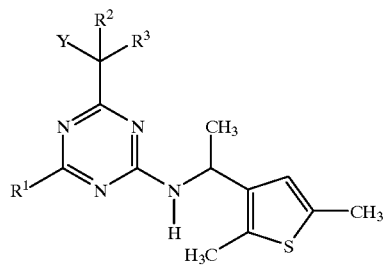

Here, R$^1$, R$^2$, R$^3$ and Y have, for example, the meanings given above in group 1.

Group 19

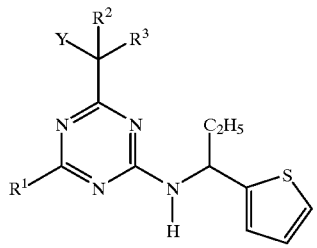

Here, R$^1$, R$^2$, R$^3$ and Y have, for example, the meanings given above in group 1.

Group 20

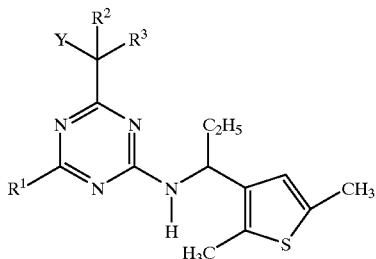

Here, R$^1$, R$^2$, R$^3$ and Y have, for example, the meanings given above in group 1.

Group 21

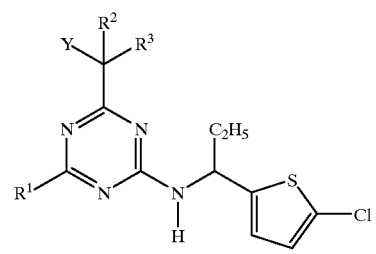

Here, R$^1$, R$^2$, R$^3$ and Y have, for example, the meanings given above in group 1.

Group 22

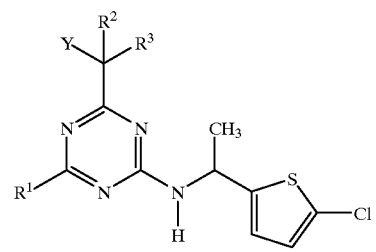

Here, R$^1$, R$^2$, R$^3$ and Y have, for example, the meanings given above in group 1.

Group 23

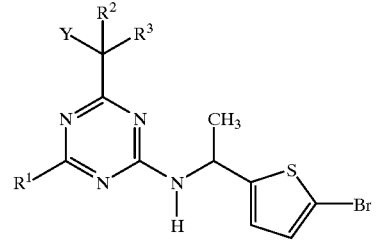

Here, R$^1$, R$^2$, R$^3$ and Y have, for example, the meanings given above in group 1.

Group 24

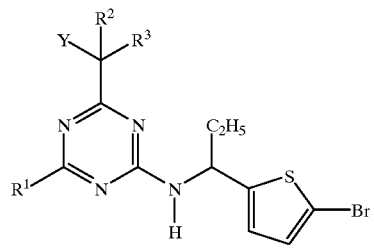

Here, $R^1$, $R^2$, $R^3$ and Y have, for example, the meanings given above in group 1.

Group 25

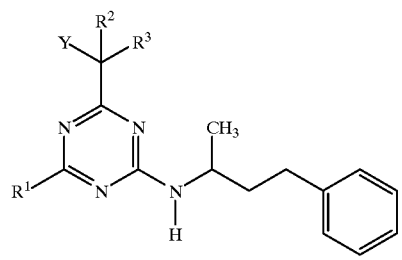

Here, $R^1$, $R^2$, $R^3$ and Y have, for example, the meanings given above in group 1.

Group 26

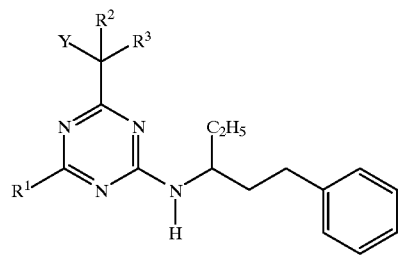

Here $R^1$, $R^2$, $R^3$ and Y have, for example, the meanings given above in group 1.

Group 27

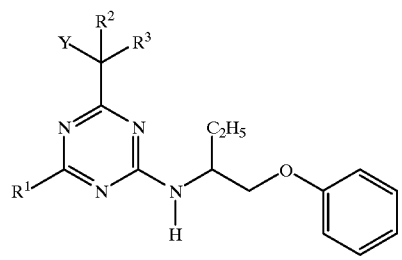

Here, $R^1$, $R^2$, $R^3$ and Y have, for example, the meanings given above in group 1.

Group 28

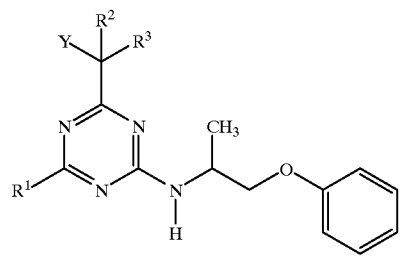

Here $R^1$, $R^2$, $R^3$ and Y have, for example, the meanings given above in group 1.

Group 29

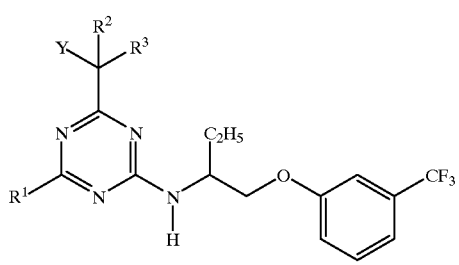

Here, $R^1$, $R^2$, $R^3$ and Y have, for example, the meanings given above in group 1.

Group 30

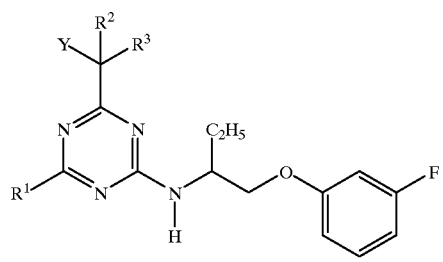

Here, $R^1$, $R^2$, $R^3$ and Y have, for example, the meanings given above in group 1.

Group 31

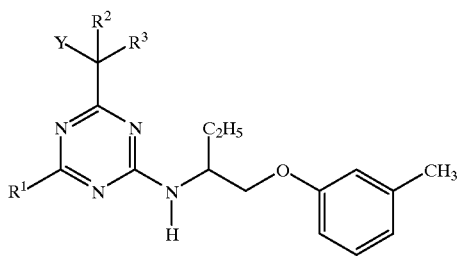

Here, $R^1$, $R^2$, $R^3$ and Y have, for example, the meanings given above in group 1.

Group 32

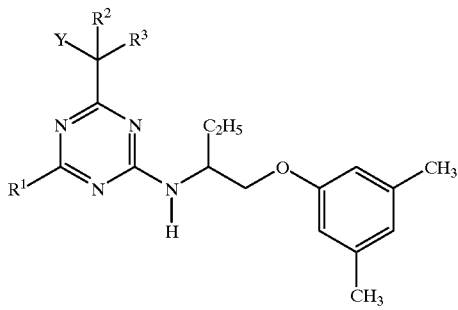

Here, $R^1$, $R^2$, $R^3$ and Y have, for example, the meanings given above in group 1.

Group 33

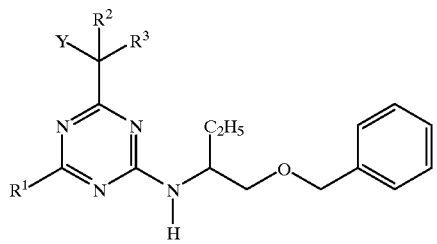

Here, $R^1$, $R^2$, $R^3$ and Y have, for example, the meanings given above in group 1.

Group 34

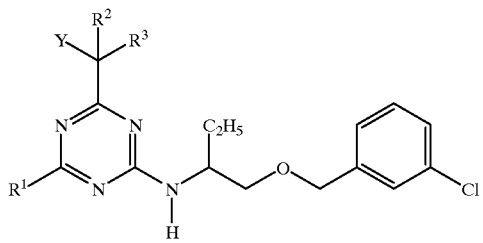

Here, $R^1$, $R^2$, $R^3$ and Y have, for example, the meanings given above in group 1.

Group 35

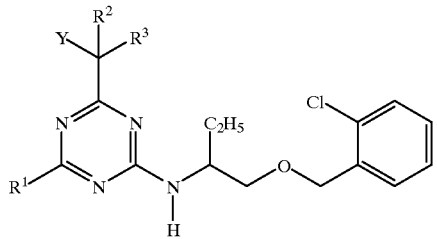

Here, $R^1$, $R^2$, $R^3$ and Y have, for example, the meanings given above in group 1.

Group 36

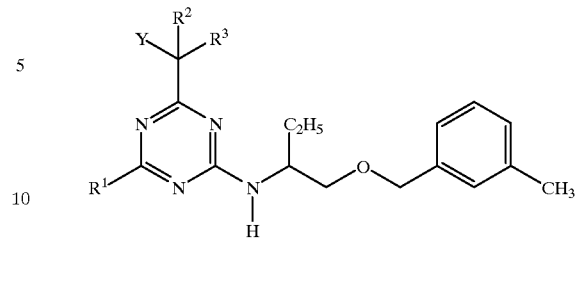

Here, $R^1$, $R^2$, $R^3$ and Y have, for example, the meanings given above in group 1.

Group 37

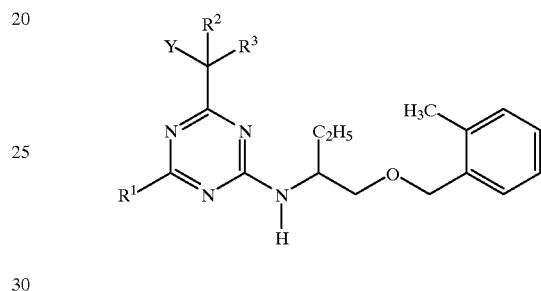

Here, $R^1$, $R^2$, $R^3$ and Y have, for example, the meanings given above in group 1.

Group 38

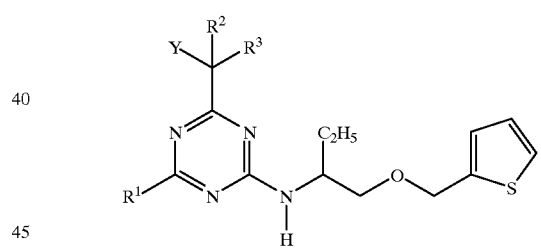

Here, $R^1$, $R^2$, $R^3$ and Y have, for example, the meanings given above in group 1.

Group 39

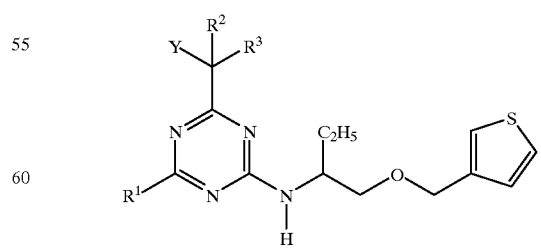

Here, $R^1$, $R^2$, $R^3$ and Y have, for example, the meanings given above in group 1.

Group 40

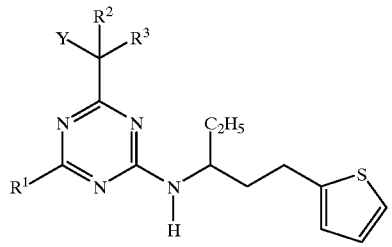

Here, $R^1$, $R^2$, $R^3$ and Y have, for example, the meanings given above in group 1.

Group 41

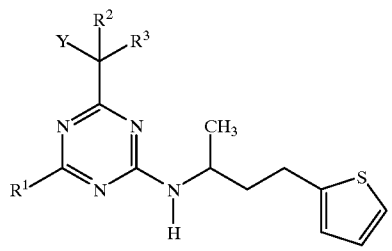

Here, $R^1$, $R^2$, $R^3$ and Y have, for example, the meanings given above in group 1.

Group 42

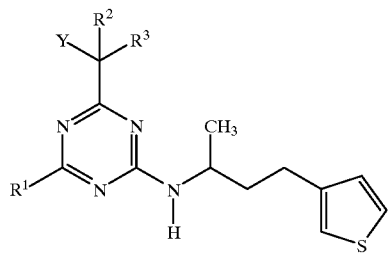

Here, $R^1$, $R^2$, $R^3$ and Y have, for example, the meanings given above in group 1.

Group 43

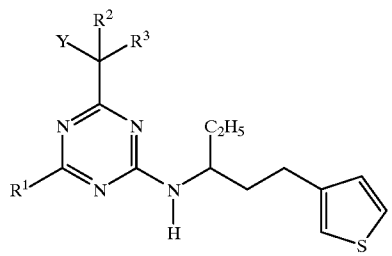

Here, $R^1$, $R^2$, $R^3$ and Y have, for example, the meanings given above in group 1.

Group 44

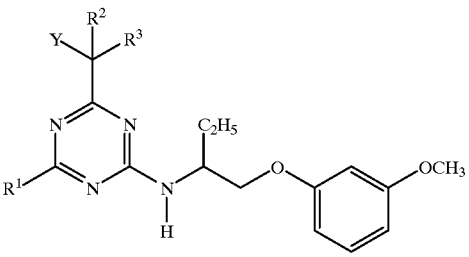

Here, $R^1$, $R^2$, $R^3$ and Y have, for example, the meanings given above in group 1.

Group 45

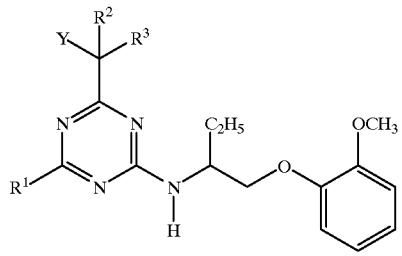

Here, $R^1$, $R^2$, $R^3$ and Y have, for example, the meanings given above in group 1.

Group 46

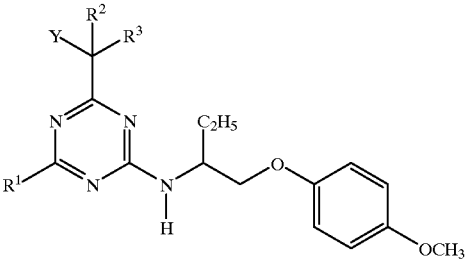

Here, $R^1$, $R^2$, $R^3$ and Y have, for example, the meanings given above in group 1.

Group 47

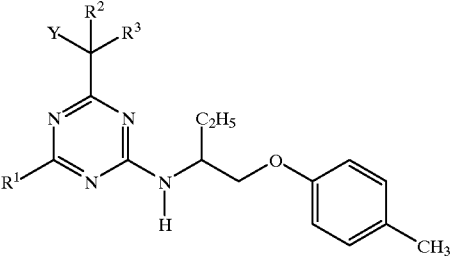

Here, $R^1$, $R^2$, $R^3$ and Y have, for example, the meanings given above in group 1.

Group 48

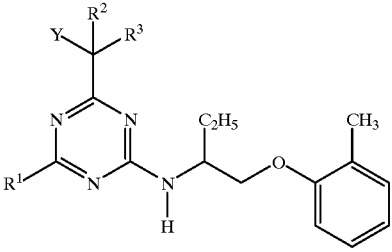

Here, $R^1$, $R^2$, $R^3$ and Y have, for example, the meanings given above in group 1.

Group 49

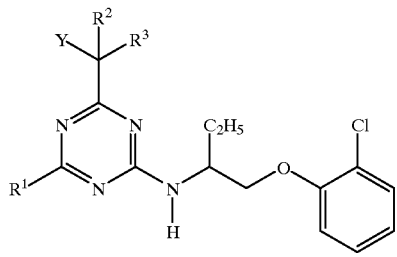

Here, $R^1$, $R^2$, $R^3$ and Y have, for example, the meanings given above in group 1.

Group 50

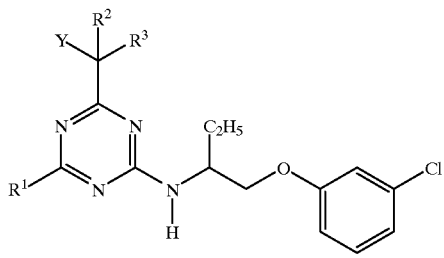

Here, $R^1$, $R^2$, $R^3$ and Y have, for example, the meanings given above in group 1.

Using, for example, (S)-1-(1-phenylpropyl)biguanide and ethyl (S)-1-chloropropionate as starting materials, the course of the reaction in the process according to the invention can be illustrated by the following formula scheme:

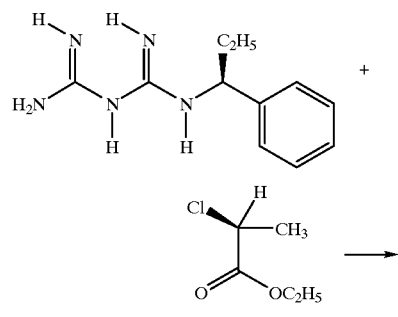

-continued

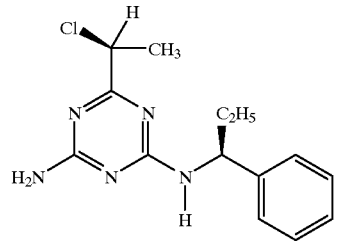

The formula (II) provides a general definition of the substituted biguanides to be used as starting materials in the process according to the invention for preparing compounds of the formula (I). In the formula (II), A, $R^1$, $R^4$ and Z each preferably or in particular have those meanings which have already been mentioned above in connection with the description of the compounds of the formula (I) according to the invention as being preferred or as being particularly preferred for A, $R^1$, $R^4$ and Z.

The starting materials of the general formula (II) are known and/or can be prepared by processes known per se (cf. EP-509 544, U.S. Pat. No. 3,816,419, U.S. Pat. No. 3,860,648, WO 97/00 254, WO 97/08 156, DE-19 641 691 (Le A 31 995), DE-19 641 692 (Le A 32 037), DE-19 641 693 (Le A 31 975), Preparation Examples).

The formula (III) provides a general definition of the carboxylic acid derivatives further to be used as starting materials in the process according to the invention. In the formula (III), $R^2$, $R^3$ and Y each preferably or in particular have those meanings which have already been mentioned above in connection with the description of the compounds of the formula (I) according to the invention as being preferred or as being particularly preferred for $R^2$, $R^3$ and Y; X preferably represents fluorine, chlorine, bromine or $C_1$–$C_4$-alkoxy, in particular represents methoxy or ethoxy.

The starting materials of the general formula (III) are known and/or can be prepared by processes known per se (cf. J. Chem. Soc. Perkin Trans. I, 1979, 2248–2252; Preparation Examples).

The process according to the invention for preparing the compounds of the general formula (I) is preferably carried out using a reaction auxiliary. Suitable reaction auxiliaries for the process according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]octane (DABCO), 1,5-diazabicyclo[4,3,0]non-5-ene (DBN), or 1,8-diazabicyclo[5,4,0]undec-7-ene (DBU).

The process according to the invention for preparing the compounds of the general formula (I) is preferably carried out using a diluent. Suitable diluents for carrying out the process according to the invention are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide; alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

When carrying out the process according to the invention, the reaction temperatures can be varied within a relatively wide range. In general, the process is carried out at temperatures between 0° C. and 150° C., preferably between 10° C. and 100° C.

The process according to the invention is generally carried out under atmospheric pressure. However, it is also possible to carry out the process according to the invention under elevated or reduced pressure—in general between 0.1 bar and 10 bar.

For carrying out the process according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred for several hours at the required temperature. Work-up is carried out by customary methods (cf. the Preparation Examples).

The active compounds according to the invention can be used as defoliants, desiccants, haulm killers and, especially, as weed killers. By weeds in the broadest sense there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.

Monocotyledonous crops of the genera: Oryza, Zea, Triticum, Hordeum, Avena, Secale, Sorghum, Panicum, Saccharum, Ananas, Asparagus, Allium.

However, the use of the active compounds according to the invention is in no way restricted to these genera, but also extends in the same manner to other plants.

Depending on the concentration, the compounds are suitable for total weed control, for example on industrial terrain and rail tracks and on paths and areas with or without tree growth. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention are particularly suitable for selective control of monocotyledonous and dicotyledonous weeds in monocotyledonous and dicotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use colorants, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlomitrofen, chlorsulfuron, chlorotoluron, cinmethylin, cinosulfuron, clethodim, clodinafop(-propargyl), clomazone, clomeprop, clopyralid, clopyrasulfuron(-methyl), cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron(-methyl), ethofumesate, ethoxyfen, ethoxysulfuron, etobenzanid, fenoxaprop(-P-ethyl), flamprop(-isopropyl), flamprop(-isopropyl-L), flamprop(-methyl), flazasulfuron, fluazifop(-P-butyl), flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(-isopropylammonium), halosafen, haloxyfop(-ethoxyethyl), haloxyfop(-P-methyl), hexazinone, imazamethabenz(-methyl), imazamethapyr, imazamox, imazapyr, imazaquin, imazethapyr, imazosulfuron, ioxynil, isopropalin, isoproturon, isouron, isoxaben, isoxaflutole, isoxapyrifop, lactofen, lenacil, linuron, MCPA, MCPP, mefenacet, metamitron, metazachltor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron (-ethyl), pyrazoxyfen, pyribenzoxim, pyributicarb, pyridate, pyriminobac(-methyl), pyrithiobac(-sodium), quinchlorac, quinmerac, quinoclamine, quizalofop(-P-ethyl), quizalofop (-P-tefuryl), rimsulfuron, sethoxydim, simazine, simetryn, sulcotrione, sulfentrazone, sulfometuron(-methyl), sulfosate, sulfosulfuron, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

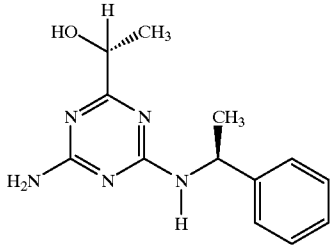

At 20° C., a solution of 2.4 g (44 mmol) of sodium methoxide in 10 ml of methanol is added dropwise with stirring to a mixture of 9.7 g (40 mmol) of (S)-1-(1-phenyl-ethyl)-biguanide, 4.5 g (40 mmol) of ethyl (R)-lactate and 80 ml of methanol, and the reaction mixture is then stirred at room temperature (approximately 20° C.) for another 15 hours. The mixture is then diluted to about three times its original volume using approximately equivalent amounts by volume of methylene chloride and water, the mixture is shaken and the organic phase is then separated off, washed with water, dried with sodium sulphate and filtered. From the filtrate, the solvent is carefully distilled off under water-pump vacuum.

This gives 4.4 g (42% of theory) of 2-amino-4-(R)-(1-hydroxyethyl)-6-(S)-(1-phenyl-ethylamino)-1,3,5-triazine as an amorphousousous residue.

$[\alpha]_D^{20} = -93.5°$.

Analogously to Preparation Example 1, and in accordance with the general description of the preparation process according to the invention, it is also possible to prepare, for example, the compounds of the formula (I) listed in Table 1 below. Here, as stated above in the definition of the compounds of the formula (I), the stereochemical specifications (for the characterization of the diastereomer types) are abbreviated by R,R or R,S or S,R or S,S or R,rac or S,rac; i.e. in each case the first specification refers to the triazine substituent —CR²R³Y and the second to the amino substituent —CHR⁴(A—Z).

TABLE 1

Examples of compounds of the formula (I)

(I)

[Structure of formula (I): triazine ring with substituents R¹, and CR²R³Y, and NH-CHR⁴-A-Z]

| Ex. No. | A | R¹ | R² | R³ | R⁴ | Y | Z | Physical data and stereochemical spec. |
|---|---|---|---|---|---|---|---|---|
| 2 | —CH₂—O—CH₃ | NH₂ | H | CH₃ | C₂H₅ | OH | 3,5-dimethylphenyl | (amorphous) (R, rac) |
| 3 | —CH₂—O—CH₃ | NH₂ | H | CH₃ | C₂H₅ | OH | 3,5-dimethylphenyl | (amorphous) (S, rac) |
| 4 | —CH₂—O—CH₃ | NH₂ | H | CH₃ | C₂H₅ | Cl | 3,5-dimethylphenyl | (amorphous) (S, rac) |
| 5 | —CH₂—O—CH₃ | NH₂ | H | CH₃ | C₂H₅ | Cl | 3,5-dimethylphenyl | (amorphous) (R, rac) |
| 6 | —CH₂—O—CH₃ | NH₂ | H | CH₃ | C₂H₅ | Cl | 3-methylphenyl | (amorphous) (R, rac) |
| 7 | —CH₂—O—CH₃ | NH₂ | H | CH₃ | C₂H₅ | Cl | 3-methylphenyl | (amorphous) (S, rac) |

TABLE 1-continued

Examples of compounds of the formula (I)

(I)

| Ex. No. | A | R¹ | R² | R³ | R⁴ | Y | Z | Physical data and stereochemical spec. |
|---|---|---|---|---|---|---|---|---|
| 8 | −CH₂−O−CH₃ | −C(=O)NH−CH₃ (on C₂H₅) i.e. C₂H₅ with CONHCH₃ | H | CH₃ | C₂H₅ | Cl | phenyl (4-methyl) | (amorphous) (R, rac) |
| 9 | −CH₂−O−CH₃ | C₂H₅ with C(=O)NHCH₃ | H | CH₃ | C₂H₅ | Cl | phenyl (4-methyl) | (amorphous) (S, rac) |
| 10 | −CH₂−CH₂− | NH₂ | H | CH₃ | C₂H₅ | OH | 2-methylthiophene | $[\alpha]_D^{20}$ = −8.6° (S, rac) |
| 11 | −CH₂−CH₂− | NH₂ | H | CH₃ | C₂H₅ | OH | 2-methylthiophene | $[\alpha]_D^{20}$ = −12.1° (R, rac) |
| 12 | −CH₂−CH₂− | NH₂ | H | CH₃ | C₂H₅ | OH | 3-methylthiophene | $[\alpha]_D^{20}$ = +8.5° (R, rac) |
| 13 | −CH₂−CH₂− | NH₂ | H | CH₃ | C₂H₅ | Cl | 2-methylthiophene | $[\alpha]_D^{20}$ = +8.3° (R, rac) |
| 14 | −CH₂−CH₂− | NH₂ | H | CH₃ | C₂H₅ | Cl | 2-methylthiophene | $[\alpha]_D^{20}$ = −8.2° (S, rac) |
| 15 | −CH₂−CH₂− | NH₂ | H | CH₃ | C₂H₅ | Cl | 3-methylthiophene | $[\alpha]_D^{20}$ = −6.0° (S, rac) |
| 16 | −CH₂−CH₂− | NH₂ | H | CH₃ | C₂H₅ | Cl | 3-methylthiophene | $[\alpha]_D^{20}$ = +6.3° (R, rac) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 17 | — | NH₂ | H | CH₃ | CH₃ | OH | 4-methylphenyl | $[\alpha]_D^{20}$ = −120° (S, S) |
| 18 | — | NH₂ | H | CH₃ | CH₃ | Cl | 4-methylphenyl | $[\alpha]_D^{20}$ = −107° (R, S) |
| 19 | — | NH₂ | H | CH₃ | CH₃ | Cl | 4-methylphenyl | $[\alpha]_D^{20}$ = −126° (S, S) |
| 20 | — | NH₂ | H | CH₃ | C₂H₅ | OH | 4-methylphenyl | $[\alpha]_D^{20}$ = −107° (S, S) |
| 21 | — | NH₂ | H | CH₃ | C₂H₅ | OH | 4-methylphenyl | $[\alpha]_D^{20}$ = −102° (R, S) |
| 22 | — | NH₂ | H | CH₃ | C₂H₅ | Cl | 4-methylphenyl | (amorphous) (S, S) |
| 23 | — | NH₂ | H | CH₃ | C₂H₅ | Cl | 4-methylphenyl | $[\alpha]_D^{20}$ = −105° (R, S) |
| 24 | — | NH₂ | H | CH₃ | C₂H₅ | F | 4-methylphenyl | oil (R, S) |
| 25 | — | NH₂ | H | CH₃ | C₂H₅ | F | 4-methylphenyl | oil (R, S) |

TABLE 1-continued

Examples of compounds of the formula (I)

(I)

| Ex. No. | A | R¹ | R² | R³ | R⁴ | Y | Z | Physical data and stereochemical spec. |
|---|---|---|---|---|---|---|---|---|
| 26 | -CH₂-CH-CH₂- | NH₂ | H | CH₃ | CH₃ | F | 4-methylphenyl | $[\alpha]_D^{20}$ = +13° (S, R) |
| 27 | -CH₂-CH-CH₂- | NH₂ | H | CH₃ | CH₃ | F | 4-methylphenyl | $[\alpha]_D^{20}$ = −23° (R, R) |
| 28 | — | CH₃-C(O)-NH- | H | CH₃ | CH₃ | Cl | 4-methylphenyl | (R, S) |
| 29 | — | C₂H₅-C(O)-NH- | H | CH₃ | CH₃ | Cl | 4-methylphenyl | (R, S) |
| 30 | — | (CH₃)₂N-CH=N- | H | CH₃ | CH₃ | Cl | 4-methylphenyl | (R, S) |
| 31 | — | CH₃-C(O)-NH- | H | CH₃ | CH₃ | Cl | 4-methylphenyl | (S, S) |
| 32 | — | C₂H₅-C(O)-NH- | H | CH₃ | CH₃ | Cl | 4-methylphenyl | (S, S) |
| 33 | — | (CH₃)₂N-CH=N- | H | CH₃ | CH₃ | Cl | 4-methylphenyl | (S, S) |
| 34 | — | H-C(O)-NH- | H | CH₃ | C₂H₅ | Cl | 4-methylphenyl | (S, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 35 | — | CH₃C(O)NH— | H | CH₃ | C₂H₅ | Cl | 4-methylphenyl | (S, S) |
| 36 | — | C₂H₅C(O)NH— | H | CH₃ | C₂H₅ | Cl | 4-methylphenyl | (S, S) |
| 37 | — | (CH₃)₂N–CH=N— | H | CH₃ | C₂H₅ | Cl | 4-methylphenyl | (S, S) |
| 38 | — | HC(O)NH— | H | CH₃ | C₂H₅ | Cl | 4-methylphenyl | (R, S) |
| 39 | — | CH₃C(O)NH— | H | CH₃ | C₂H₅ | Cl | 4-methylphenyl | (R, S) |
| 40 | — | C₂H₅C(O)NH— | H | CH₃ | C₂H₅ | Cl | 4-methylphenyl | (R, S) |
| 41 | — | (CH₃)₂N–CH=N— | H | CH₃ | C₂H₅ | Cl | 4-methylphenyl | (R, S) |
| 42 | — | NH₂ | H | CH₃ | CH₃ | F | 4-methylphenyl | (S, S) |
| 43 | — | NH₂ | H | CH₃ | CH₃ | F | 4-methylphenyl | (R, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 44 | — | NH₂ | H | CH₃ | CH₃ | Cl | 4-Cl-C₆H₄ | (S, S) |
| 45 | — | NH₂ | H | CH₃ | CH₃ | Cl | 4-Cl-C₆H₄ | (R, S) |
| 46 | — | NH₂ | H | CH₃ | CH₃ | OH | 4-Cl-C₆H₄ | (R, S) |
| 47 | — | NH₂ | H | CH₃ | CH₃ | OH | 4-Cl-C₆H₄ | (S, S) |
| 48 | — | NH₂ | H | CH₃ | CH₃ | F | 4-Cl-C₆H₄ | (R, S) |
| 49 | — | NH₂ | H | CH₃ | CH₃ | F | 4-Cl-C₆H₄ | (S, S) |
| 50 | — | NH₂ | H | CH₃ | CH₃ | F | 4-Cl-C₆H₄ | Log p: 1.80[a] (R, R) |
| 51 | — | NH₂ | H | CH₃ | CH₃ | F | 4-Cl-C₆H₄ | (S, R) |
| 52 | — | NH₂ | H | CH₃ | CH₃ | OH | 4-CH₃-C₆H₄ | (S, S) |

TABLE 1-continued

Examples of compounds of the formula (I)

(I)

| Ex. No. | A | R¹ | R² | R³ | R⁴ | Y | Z | Physical data and stereochemical spec. |
|---|---|---|---|---|---|---|---|---|
| 53 | — | NH₂ | H | CH₃ | CH₃ | OH | 4-CH₃-C₆H₄ | (R, S) |
| 54 | — | NH₂ | H | CH₃ | CH₃ | Cl | 4-CH₃-C₆H₄ | (S, S) |
| 55 | — | NH₂ | H | CH₃ | CH₃ | Cl | 4-CH₃-C₆H₄ | (R, S) |
| 56 | — | NH₂ | H | CH₃ | CH₃ | F | 4-CH₃-C₆H₄ | (S, S) |
| 57 | — | NH₂ | H | CH₃ | CH₃ | F | 4-CH₃-C₆H₄ | (R, S) |
| 58 | — | NH₂ | H | CH₃ | CH₃ | OH | 4-OCH₃-C₆H₄ | (S, S) |
| 59 | — | NH₂ | H | CH₃ | CH₃ | OH | 4-OCH₃-C₆H₄ | (R, S) |
| 60 | — | NH₂ | H | CH₃ | CH₃ | Cl | 4-OCH₃-C₆H₄ | (S, S) |
| 61 | — | NH₂ | H | CH₃ | CH₃ | Cl | 4-OCH₃-C₆H₄ | (R, S) |

TABLE 1-continued

Examples of compounds of the formula (I)

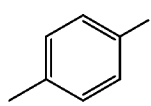

| Ex. No. | A | $R^1$ | $R^2$ | $R^3$ | $R^4$ | Y | Z | Physical data and stereo-chemical spec. |
|---|---|---|---|---|---|---|---|---|
| 62 | — | $NH_2$ | H | $CH_3$ | $CH_3$ | F | 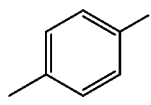 4-OCH$_3$-phenyl | (S, S) |
| 63 | — | $NH_2$ | H | $CH_3$ | $CH_3$ | F | 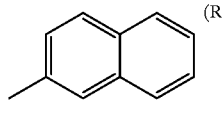 4-OCH$_3$-phenyl | (R, S) |
| 64 | — | $NH_2$ | H | $CH_3$ | $CH_3$ | OH | 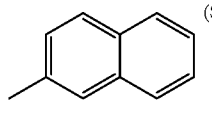 2-naphthyl | (R, R) |
| 65 | — | $NH_2$ | H | $CH_3$ | $CH_3$ | OH | 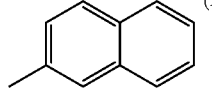 2-naphthyl | (S, R) |
| 66 | — | $NH_2$ | H | $CH_3$ | $CH_3$ | Cl | 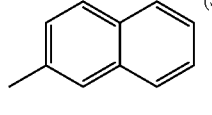 2-naphthyl | (R, R) |
| 67 | — | $NH_2$ | H | $CH_3$ | $CH_3$ | Cl | 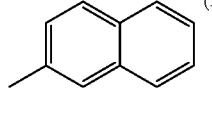 2-naphthyl | (S, R) |
| 68 | — | $NH_2$ | H | $CH_3$ | $CH_3$ | F | 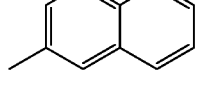 2-naphthyl | (R, R) |
| 69 | — | $NH_2$ | H | $CH_3$ | $CH_3$ | F | 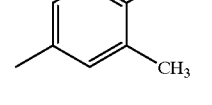 2-naphthyl | (S, R) |
| 70 | — | $NH_2$ | H | $CH_3$ | $CH_3$ | Cl | 2,4-dimethylphenyl | (R, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 71 | — | $NH_2$ | H | $CH_3$ | $CH_3$ | Cl | 3,4-dimethylphenyl | (S, S) |
| 72 | — | $NH_2$ | H | $CH_3$ | $CH_3$ | F | 3,4-dimethylphenyl | (R, S) |
| 73 | — | $NH_2$ | H | $CH_3$ | $CH_3$ | F | 3,4-dimethylphenyl | (R, R) |
| 74 | — | $NH_2$ | H | $CH_3$ | $CH_3$ | F | 3,4-dimethylphenyl | (S, S) |
| 75 | — | $NH_2$ | H | $CH_3$ | $CH_3$ | F | 3,4-dimethylphenyl | (S, R) |
| 76 | — | $NH_2$ | H | $CH_3$ | $CH_3$ | Cl | 4-fluorophenyl | (R, S) |
| 77 | — | $NH_2$ | H | $CH_3$ | $CH_3$ | Cl | 4-fluorophenyl | (S, S) |
| 78 | — | $NH_2$ | H | $CH_3$ | $CH_3$ | F | 4-fluorophenyl | (R, S) |
| 79 | — | $NH_2$ | H | $CH_3$ | $CH_3$ | F | 4-fluorophenyl | (S, S) |

TABLE 1-continued
Examples of compounds of the formula (I)
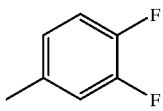
| Ex. No. | A | R¹ | R² | R³ | R⁴ | Y | Z | Physical data and stereo- chemical spec. |
|---|---|---|---|---|---|---|---|---|
| 80 | — | NH₂ | H | CH₃ | CH₃ | F | 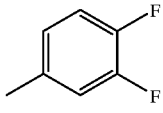 | (R, R) |
| 81 | — | NH₂ | H | CH₃ | CH₃ | F | 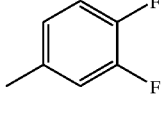 | (S, R) |
| 82 | — | NH₂ | H | CH₃ | CH₃ | Cl | 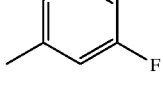 | (R, S) |
| 83 | — | NH₂ | H | CH₃ | CH₃ | Cl | 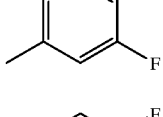 | (S, S) |
| 84 | — | NH₂ | H | CH₃ | CH₃ | F | 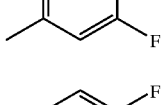 | (R, S) |
| 85 | — | NH₂ | H | CH₃ | CH₃ | F | 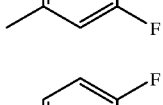 | (S, S) |
| 86 | — | NH₂ | H | CH₃ | C₂H₅ | F | 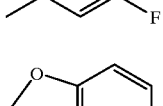 | (R, S) |
| 87 | — | NH₂ | H | CH₃ | C₂H₅ | F | 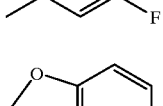 | (S, S) |
| 88 | — | NH₂ | H | CH₃ | CH₃ | F | 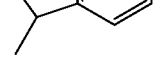 | (R, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 89 | — | NH₂ | H | CH₃ | CH₃ | F | 3-methyl-2,3-dihydrobenzofuran | (S, S) |
| 90 | — | NH₂ | H | CH₃ | CH₃ | F | 3-methyl-2,3-dihydrobenzofuran | (R, S) |
| 91 | — | NH₂ | H | CH₃ | CH₃ | F | 3-methyl-2,3-dihydrobenzofuran | (S, S) |
| 92 | — | NH₂ | H | CH₃ | C₂H₅ | Cl | 2-methylthiophene | (R, R) |
| 93 | — | NH₂ | H | CH₃ | C₂H₅ | Cl | 2-methylthiophene | (S, R) |
| 94 | — | NH₂ | H | CH₃ | C₂H₅ | F | 2-methylthiophene | (S, R) |
| 95 | — | NH₂ | H | CH₃ | C₂H₅ | F | 2-methylthiophene | (R, R) |
| 96 | -CH₂CH₂CH₂- | NH₂ | H | CH₃ | C₂H₅ | F | 4-methylphenyl | (R, R) |
| 97 | -CH₂CH₂CH₂- | NH₂ | H | CH₃ | C₂H₅ | F | 4-methylphenyl | (R, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 98 | -CH₂-CH₂- | NH₂ | H | CH₃ | C₂H₅ | F | 4-methylphenyl | (S, R) |
| 99 | -CH₂-CH₂- | NH₂ | H | CH₃ | C₂H₅ | F | 4-methylphenyl | (S, S) |
| 100 | -CH₂-CH₂- | NHC(O)CH₃ | H | CH₃ | C₂H₅ | F | 4-methylphenyl | (R, R) |
| 101 | -CH₂-CH₂- | NHC(O)CH₃ | H | CH₃ | C₂H₅ | F | 4-methylphenyl | (S, R) |
| 102 | -CH₂-O- | NH₂ | H | CH₃ | CH₃ | F | 4-methylphenyl | (R, R) |
| 103 | -CH₂-O- | NH₂ | H | CH₃ | CH₃ | F | 4-methylphenyl | (S, R) |
| 104 | -CH₂-O- | NH₂ | H | CH₃ | CH₃ | F | 4-methylphenyl | (R, S) |
| 105 | -CH₂-O- | NH₂ | H | CH₃ | CH₃ | F | 4-methylphenyl | (S, S) |
| 106 | -CH₂-O- | NH₂ | H | CH₂ | C₂H₅ | F | 4-methylphenyl | (R, R) |

TABLE 1-continued

Examples of compounds of the formula (I)

| Ex. No. | A | R¹ | R² | R³ | R⁴ | Y | Z | Physical data and stereochemical spec. |
|---|---|---|---|---|---|---|---|---|
| 107 | -CH₂-O-CH₃ | NH₂ | H | CH₂ | C₂H₅ | F | 3-methylphenyl | (S, R) |
| 108 | -CH₂-O-CH₃ | NH₂ | H | CH₂ | C₂H₅ | F | 3-methylphenyl | (R, S) |
| 109 | -CH₂-O-CH₃ | NH₂ | H | CH₂ | C₂H₅ | F | 3-methylphenyl | (S, S) |
| 110 | -CH₂-O-CH₃ | NH₂ | H | CH₃ | CH₃ | F | 3,5-dimethylphenyl | (R, S) |
| 111 | -CH₂-O-CH₃ | NH₂ | H | CH₃ | CH₃ | F | 3,5-dimethylphenyl | (R, R) |
| 112 | -CH₂-O-CH₃ | NH₂ | H | CH₃ | CH₃ | F | 3,5-dimethylphenyl | (S, S) |
| 113 | -CH₂-O-CH₃ | NH₂ | H | CH₃ | CH₃ | F | 3,5-dimethylphenyl | (S, R) |

TABLE 1-continued

Examples of compounds of the formula (I)

| Ex. No. | A | R¹ | R² | R³ | R⁴ | Y | Z | Physical data and stereochemical spec. |
|---|---|---|---|---|---|---|---|---|
| 114 | -CH₂-O-CH₃ | CH₃-C(=O)-NH- | H | CH₃ | CH₃ | F | 3,5-dimethylphenyl | (S, R) |
| 115 | -CH₂-O-CH₃ | CH₃-C(=O)-NH- | H | CH₃ | CH₃ | F | 3,5-dimethylphenyl | (R, R) |
| 116 | -CH₂-O-CH₃ | C₂H₅-C(=O)-NH- | H | CH₃ | CH₃ | F | 3,5-dimethylphenyl | (S, R) |
| 117 | -CH₂-O-CH₃ | C₂H₅-C(=O)-NH- | H | CH₃ | CH₃ | F | 3,5-dimethylphenyl | (R, R) |
| 118 | -CH₂-O-CH₃ | (CH₃)₂N-CH=N- | H | CH₃ | CH₃ | F | 3,5-dimethylphenyl | (S, R) |
| 119 | -CH₂-O-CH₃ | (CH₃)₂N-CH=N- | H | CH₃ | CH₃ | F | 3,5-dimethylphenyl | (R, R) |

TABLE 1-continued
Examples of compounds of the formula (I)
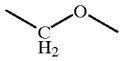
(I)
| Ex. No. | A | R¹ | R² | R³ | R⁴ | Y | Z | Physical data and stereochemical spec. |
|---|---|---|---|---|---|---|---|---|
| 120 | 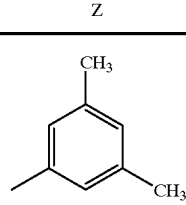 | NH₂ | H | CH₃ | C₂H₅ | F | 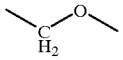 | (S, R) |
| 121 | 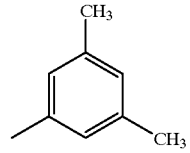 | NH₂ | H | CH₃ | C₂H₅ | F | 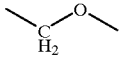 | (R, R) |
| 122 | 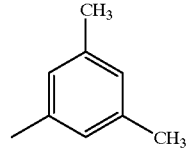 | NH₂ | H | CH₃ | C₂H₅ | F | 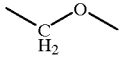 | (S, S) |
| 123 | 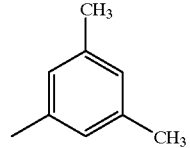 | NH₂ | H | CH₃ | C₂H₅ | F | 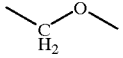 | (R, S) |
| 124 | 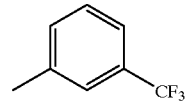 | NH₂ | H | CH₃ | CH₃ | F | 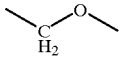 | (S, R) |
| 125 | 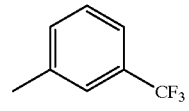 | NH₂ | H | CH₃ | CH₃ | F | 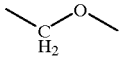 | (R, R) |
| 126 | 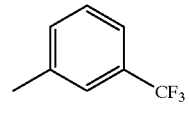 | NH₂ | H | CH₃ | CH₃ | F | | (S, S) |

TABLE 1-continued

Examples of compounds of the formula (I)

| Ex. No. | A | R¹ | R² | R³ | R⁴ | Y | Z | Physical data and stereo-chemical spec. |
|---|---|---|---|---|---|---|---|---|
| 127 | —CH₂—O—CH₃ | NH₂ | H | CH₃ | CH₃ | F | 3-CF₃-phenyl | (R, S) |
| 128 | —CH₂—O—CH₃ | NH₂ | H | CH₃ | C₂H₅ | F | 3-CF₃-phenyl | (S, R) |
| 129 | —CH₂—O—CH₃ | NH₂ | H | CH₃ | C₂H₅ | F | 3-CF₃-phenyl | (R, R) |
| 130 | —CH₂—O—CH₃ | NH₂ | H | CH₃ | CH₃ | F | 3-CH₃-phenyl | (S, R) |
| 131 | —CH₂—O—CH₃ | NH₂ | H | CH₃ | CH₃ | F | 3-CH₃-phenyl | (R, R) |
| 132 | —CH₂—O—CH₃ | NH₂ | H | CH₃ | CH₃ | F | 3-CH₃-phenyl | (S, S) |
| 133 | —CH₂—O—CH₃ | NH₂ | H | CH₃ | CH₃ | F | 3-CH₃-phenyl | (R, S) |
| 134 | —CH₂—O—CH₃ | NH₂ | H | CH₃ | C₂H₅ | F | 3-CH₃-phenyl | (S, R) |
| 135 | —CH₂—O—CH₃ | NH₂ | H | CH₃ | C₂H₅ | F | 3-CH₃-phenyl | (R, R) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 136 | CH₂-O-CH₃ | NH₂ | H | CH₃ | C₂H₅ | F | 3-CH₃-C₆H₄ | (S, S) |
| 137 | CH₂-O-CH₃ | NH₂ | H | CH₃ | C₂H₅ | F | 3-CH₃-C₆H₄ | (R, S) |
| 138 | CH₂-O-CH₃ | NH₂ | H | CH₃ | C₂H₅ | F | 3-CH₃-C₆H₄ | (S, S) |
| 139 | CH₂-O-CH₃ | NH₂ | H | CH₃ | C₂H₅ | F | 3-CF₃-C₆H₄ | (R, S) |
| 140 | CH₂-O-CH₃ | NH₂ | H | CH₃ | CH₃ | F | 3-F-C₆H₄ | (R, R) |
| 141 | CH₂-O-CH₃ | NH₂ | H | CH₃ | CH₃ | F | 3-F-C₆H₄ | (R, S) |
| 142 | CH₂-O-CH₃ | NH₂ | H | CH₃ | CH₃ | F | 3-F-C₆H₄ | (S, R) |
| 143 | CH₂-O-CH₃ | NH₂ | H | CH₃ | CH₃ | F | 3-F-C₆H₄ | (S, S) |
| 144 | CH₂-O-CH₃ | NH₂ | H | CH₃ | C₂H₅ | F | 3-F-C₆H₄ | (S, R) |

TABLE 1-continued

Examples of compounds of the formula (I)

(I)

| Ex. No. | A | R¹ | R² | R³ | R⁴ | Y | Z | Physical data and stereochemical spec. |
|---|---|---|---|---|---|---|---|---|
| 145 | CH₃-O-CH₂- | NH₂ | H | CH₃ | C₂H₅ | F | 3-F-phenyl | amorphousous (R, R) |
| 146 | CH₃-O-CH₂- | NH₂ | H | CH₃ | C₂H₅ | F | 3-F-phenyl | (S, S) |
| 147 | CH₃-O-CH₂- | NH₂ | H | CH₃ | C₂H₅ | F | 3-F-phenyl | (R, S) |
| 148 | C₂H₅-O-CH₂- | NH₂ | H | CH₃ | CH₃ | F | phenyl | (S, R) |
| 149 | C₂H₅-O-CH₂- | NH₂ | H | CH₃ | CH₃ | F | phenyl | (R, R) |
| 150 | C₂H₅-O-CH₂- | NH₂ | H | CH₃ | CH₃ | F | phenyl | (S, S) |
| 151 | C₂H₅-O-CH₂- | NH₂ | H | CH₃ | CH₃ | F | phenyl | (R, S) |
| 152 | C₂H₅-O-CH₂- | NH₂ | H | CH₃ | C₂H₅ | F | phenyl | (S, R) |
| 153 | C₂H₅-O-CH₂- | NH₂ | H | CH₃ | C₂H₅ | F | phenyl | (R, R) |

TABLE 1-continued

Examples of compounds of the formula (I)

$$(I)$$

| Ex. No. | A | R¹ | R² | R³ | R⁴ | Y | Z | Physical data and stereo-chemical spec. |
|---|---|---|---|---|---|---|---|---|
| 154 | CH₃CH₂-O-CH₂- | NH₂ | H | CH₃ | C₂H₅ | F | 4-methylphenyl | (S, S) |
| 155 | CH₃CH₂-O-CH₂- | NH₂ | H | CH₃ | C₂H₅ | F | 4-methylphenyl | (R, S) |
| 156 | CH₃CH₂-O-CH₂- | NH₂ | H | CH₃ | CH₃ | F | 4-chlorophenyl | (S, R) |
| 157 | CH₃CH₂-O-CH₂- | NH₂ | H | CH₃ | CH₃ | F | 4-chlorophenyl | (R, R) |
| 158 | CH₃CH₂-O-CH₂- | NH₂ | H | CH₃ | CH₃ | F | 4-chlorophenyl | (S, S) |
| 159 | CH₃CH₂-O-CH₂- | NH₂ | H | CH₃ | CH₃ | F | 4-chlorophenyl | (R, S) |
| 160 | CH₃CH₂-O-CH₂- | NH₂ | H | CH₃ | C₂H₅ | F | 4-chlorophenyl | (S, R) |
| 161 | CH₃CH₂-O-CH₂- | NH₂ | H | CH₃ | C₂H₅ | F | 4-chlorophenyl | (R, R) |
| 162 | CH₃CH₂-O-CH₂- | NH₂ | H | CH₃ | C₂H₅ | F | 4-chlorophenyl | (S, S) |

TABLE 1-continued

Examples of compounds of the formula (I)

(I)

| Ex. No. | A | R¹ | R² | R³ | R⁴ | Y | Z | Physical data and stereochemical spec. |
|---|---|---|---|---|---|---|---|---|
| 163 | ~O~ | NH₂ | H | CH₃ | C₂H₅ | F | 4-Cl-C₆H₄ | (R, S) |
| 164 | ~O~ | NH₂ | H | CH₃ | CH₃ | F | 4-F-C₆H₄ | (S, R) |
| 165 | ~O~ | NH₂ | H | CH₃ | CH₃ | F | 4-F-C₆H₄ | (S, S) |
| 166 | ~O~ | NH₂ | H | CH₃ | CH₃ | F | 4-F-C₆H₄ | (R, R) |
| 167 | ~O~ | NH₂ | H | CH₃ | CH₃ | F | 4-F-C₆H₄ | (R, S) |
| 168 | ~O~ | NH₂ | H | CH₃ | C₂H₅ | F | 4-F-C₆H₄ | (S, R) |
| 169 | ~O~ | NH₂ | H | CH₃ | C₂H₅ | F | 4-F-C₆H₄ | (R, R) |
| 170 | ~O~ | NH₂ | H | CH₃ | C₂H₅ | F | 4-F-C₆H₄ | (S, S) |
| 171 | ~O~ | NH₂ | H | CH₃ | C₂H₅ | F | 4-F-C₆H₄ | (R, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 172 | ~O~ | NH$_2$ | H | CH$_3$ | CH$_3$ | F | 4-CH$_3$-C$_6$H$_4$ | (S, R) |
| 173 | ~O~ | NH$_2$ | H | CH$_3$ | CH$_3$ | F | 4-CH$_3$-C$_6$H$_4$ | (R, R) |
| 174 | ~O~ | NH$_2$ | H | CH$_3$ | CH$_3$ | F | 4-CH$_3$-C$_6$H$_4$ | (S, S) |
| 175 | ~O~ | NH$_2$ | H | CH$_3$ | CH$_3$ | F | 4-CH$_3$-C$_6$H$_4$ | (R, S) |
| 176 | ~O~ | NH$_2$ | H | CH$_3$ | C$_2$H$_5$ | F | 4-CH$_3$-C$_6$H$_4$ | (S, R) |
| 177 | ~O~ | NH$_2$ | H | CH$_3$ | C$_2$H$_5$ | F | 4-CH$_3$-C$_6$H$_4$ | (R, R) |
| 178 | ~O~ | NH$_2$ | H | CH$_3$ | C$_2$H$_5$ | F | 4-CH$_3$-C$_6$H$_4$ | (S, S) |
| 179 | ~O~ | NH$_2$ | H | CH$_3$ | C$_2$H$_5$ | F | 4-CH$_3$-C$_6$H$_4$ | (R, S) |
| 180 | ~O~ | NH$_2$ | H | CH$_3$ | CH$_3$ | F | 3-Cl-C$_6$H$_4$ | (S, R) |

TABLE 1-continued

Examples of compounds of the formula (I)

| Ex. No. | A | R¹ | R² | R³ | R⁴ | Y | Z | Physical data and stereo-chemical spec. |
|---|---|---|---|---|---|---|---|---|
| 181 | ~O~ | $NH_2$ | H | $CH_3$ | $CH_3$ | F | 3-Cl-phenyl | (R, R) |
| 182 | ~O~ | $NH_2$ | H | $CH_3$ | $CH_3$ | F | 3-Cl-phenyl | (S, S) |
| 183 | ~O~ | $NH_2$ | H | $CH_3$ | $CH_3$ | F | 3-Cl-phenyl | (R, S) |
| 184 | ~O~ | $NH_2$ | H | $CH_3$ | $C_2H_5$ | F | 3-Cl-phenyl | (S, R) |
| 185 | ~O~ | $NH_2$ | H | $CH_3$ | $C_2H_5$ | F | 3-Cl-phenyl | (R, R) |
| 186 | ~O~ | $NH_2$ | H | $CH_3$ | $C_2H_5$ | F | 3-Cl-phenyl | (S, S) |
| 187 | ~O~ | $NH_2$ | H | $CH_3$ | $C_2H_5$ | F | 3-Cl-phenyl | (R, S) |
| 188 | ~O~ | $NH_2$ | H | $CH_3$ | $CH_3$ | F | 3-F-phenyl | (S, R) |
| 189 | ~O~ | $NH_2$ | H | $CH_3$ | $CH_3$ | F | 3-F-phenyl | (R, R) |

TABLE 1-continued

Examples of compounds of the formula (I)

| Ex. No. | A | R¹ | R² | R³ | R⁴ | Y | Z | Physical data and stereo-chemical spec. |
|---|---|---|---|---|---|---|---|---|
| 190 | CH₃CH₂-O-CH₂- | NH₂ | H | CH₃ | CH₃ | F | 3-F-C₆H₄- | (S, S) |
| 191 | CH₃CH₂-O-CH₂- | NH₂ | H | CH₃ | CH₃ | F | 3-F-C₆H₄- | (R, S) |
| 192 | CH₃CH₂-O-CH₂- | NH₂ | H | CH₃ | C₂H₅ | F | 3-F-C₆H₄- | (S, R) |
| 193 | CH₃CH₂-O-CH₂- | NH₂ | H | CH₃ | C₂H₅ | F | 3-F-C₆H₄- | (R, R) |
| 194 | CH₃CH₂-O-CH₂- | NH₂ | H | CH₃ | C₂H₅ | F | 3-F-C₆H₄- | (S, S) |
| 195 | CH₃CH₂-O-CH₂- | NH₂ | H | CH₃ | C₂H₅ | F | 3-F-C₆H₄- | (R, S) |
| 196 | CH₃CH₂-O-CH₂- | NH₂ | H | CH₃ | CH₃ | F | 3-CH₃-C₆H₄- | (S, R) |
| 197 | CH₃CH₂-O-CH₂- | NH₂ | H | CH₃ | CH₃ | F | 3-CH₃-C₆H₄- | (R, R) |
| 198 | CH₃CH₂-O-CH₂- | NH₂ | H | CH₃ | CH₃ | F | 3-CH₃-C₆H₄- | (S, S) |

TABLE 1-continued
Examples of compounds of the formula (I)
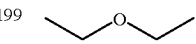
(I)
| Ex. No. | A | R¹ | R² | R³ | R⁴ | Y | Z | Physical data and stereo-chemical spec. |
|---|---|---|---|---|---|---|---|---|
| 199 | 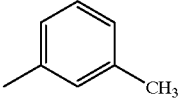 | NH$_2$ | H | CH$_3$ | CH$_3$ | F | 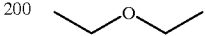 | (R, S) |
| 200 | 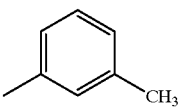 | NH$_2$ | H | CH$_3$ | C$_2$H$_5$ | F | 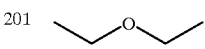 | (S, R) |
| 201 | 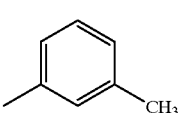 | NH$_2$ | H | CH$_3$ | C$_2$H$_5$ | F |  | (R, R) |
| 202 | 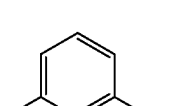 | NH$_2$ | H | CH$_3$ | C$_2$H$_5$ | F |  | (S, S) |
| 203 | 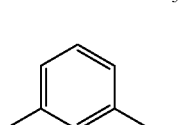 | NH$_2$ | H | CH$_3$ | C$_2$H$_5$ | F |  | (R, S) |
| 204 | 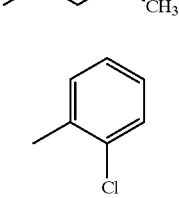 | NH$_2$ | H | CH$_3$ | CH$_3$ | F | 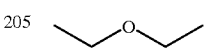 | (S, R) |
| 205 | 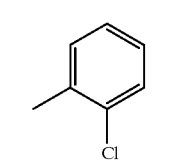 | NH$_2$ | H | CH$_3$ | CH$_3$ | F |  | (R, R) |
| 206 | 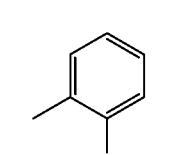 | NH$_2$ | H | CH$_3$ | CH$_3$ | F |  | (S, S) |

TABLE 1-continued

Examples of compounds of the formula (I)

| Ex. No. | A | R¹ | R² | R³ | R⁴ | Y | Z | Physical data and stereo-chemical spec. |
|---|---|---|---|---|---|---|---|---|
| 207 | CH₂-O-C₂H₅ | NH₂ | H | CH₃ | CH₃ | F | 2-Cl-C₆H₄ | (R, S) |
| 208 | CH₂-O-C₂H₅ | NH₂ | H | CH₃ | C₂H₅ | F | 2-Cl-C₆H₄ | (S, R) |
| 209 | CH₂-O-C₂H₅ | NH₂ | H | CH₃ | C₂H₅ | F | 2-Cl-C₆H₄ | (R, R) |
| 210 | CH₂-O-C₂H₅ | NH₂ | H | CH₃ | C₂H₅ | F | 2-Cl-C₆H₄ | (S, S) |
| 211 | CH₂-O-C₂H₅ | NH₂ | H | CH₃ | C₂H₅ | F | 2-Cl-C₆H₄ | (R, S) |
| 212 | CH₂-O-C₂H₅ | NH₂ | H | CH₃ | CH₃ | F | 2-F-C₆H₄ | (S, R) |
| 213 | CH₂-O-C₂H₅ | NH₂ | H | CH₃ | CH₃ | F | 2-F-C₆H₄ | (R, R) |

TABLE 1-continued

Examples of compounds of the formula (I)

(I)

| Ex. No. | A | R¹ | R² | R³ | R⁴ | Y | Z | Physical data and stereo- chemical spec. |
|---|---|---|---|---|---|---|---|---|
| 214 | ~O~ | NH$_2$ | H | CH$_3$ | CH$_3$ | F | 2-fluorophenyl | (S, S) |
| 215 | ~O~ | NH$_2$ | H | CH$_3$ | CH$_3$ | F | 2-fluorophenyl | (R, S) |
| 216 | ~O~ | NH$_2$ | H | CH$_3$ | C$_2$H$_5$ | F | 2-fluorophenyl | (S, R) |
| 217 | ~O~ | NH$_2$ | H | CH$_3$ | C$_2$H$_5$ | F | 2-fluorophenyl | (R, R) |
| 218 | ~O~ | NH$_2$ | H | CH$_3$ | C$_2$H$_5$ | F | 2-fluorophenyl | (S, S) |
| 219 | ~O~ | NH$_2$ | H | CH$_3$ | C$_2$H$_5$ | F | 2-fluorophenyl | (R, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 220 | ⁓O⁓ | NH₂ | H | CH₃ | CH₃ | F | 2-methylphenyl | (S, R) |
| 221 | ⁓O⁓ | NH₂ | H | CH₃ | CH₃ | F | 2-methylphenyl | (R, R) |
| 222 | ⁓O⁓ | NH₂ | H | CH₃ | CH₃ | F | 2-methylphenyl | (S, S) |
| 223 | ⁓O⁓ | NH₂ | H | CH₃ | CH₃ | F | 2-methylphenyl | (R, S) |
| 224 | ⁓O⁓ | NH₂ | H | CH₃ | C₂H₅ | F | 2-methylphenyl | (S, R) |
| 225 | ⁓O⁓ | NH₂ | H | CH₃ | C₂H₅ | F | 2-methylphenyl | (R, R) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 226 | ⌒O⌒ | NH₂ | H | CH₃ | C₂H₅ | F | 2-methylphenyl | (S, S) |
| 227 | ⌒O⌒ | NH₂ | H | CH₃ | C₂H₅ | F | 2-methylphenyl | (R, S) |
| 228 | ⌒O⌒ | NH₂ | H | CH₃ | CH₃ | F | 2-methylthienyl | (S, R) |
| 229 | ⌒O⌒ | NH₂ | H | CH₃ | CH₃ | F | 2-methylthienyl | (R, R) |
| 230 | ⌒O⌒ | NH₂ | H | CH₃ | CH₃ | F | 2-methylthienyl | (S, S) |
| 231 | ⌒O⌒ | NH₂ | H | CH₃ | CH₃ | F | 2-methylthienyl | (R, S) |
| 232 | ⌒O⌒ | NH₂ | H | CH₃ | C₂H₅ | F | 2-methylthienyl | (S, R) |
| 233 | ⌒O⌒ | NH₂ | H | CH₃ | C₂H₅ | F | 2-methylthienyl | (R, R) |
| 234 | ⌒O⌒ | NH₂ | H | CH₃ | C₂H₅ | F | 2-methylthienyl | (S, S) |

TABLE 1-continued

Examples of compounds of the formula (I)

| Ex. No. | A | R¹ | R² | R³ | R⁴ | Y | Z | Physical data and stereochemical spec. |
|---|---|---|---|---|---|---|---|---|
| 235 | -CH₂-O-C₂H₅ | NH₂ | H | CH₃ | C₂H₅ | F | 2-methylthiophene | (R, S) |
| 236 | -CH₂-O-C₂H₅ | NH₂ | H | CH₃ | CH₃ | F | 3-methylthiophene | (S, R) |
| 237 | -CH₂-O-C₂H₅ | NH₂ | H | CH₃ | CH₃ | F | 3-methylthiophene | (R, R) |
| 238 | -CH₂-O-C₂H₅ | NH₂ | H | CH₃ | CH₃ | F | 3-methylthiophene | (S, S) |
| 239 | -CH₂-O-C₂H₅ | NH₂ | H | CH₃ | CH₃ | F | 3-methylthiophene | (R, S) |
| 240 | -CH₂-O-C₂H₅ | NH₂ | H | CH₃ | C₂H₅ | F | 3-methylthiophene | (S, R) |
| 241 | -CH₂-O-C₂H₅ | NH₂ | H | CH₃ | C₂H₅ | F | 3-methylthiophene | (R, R) |
| 242 | -CH₂-O-C₂H₅ | NH₂ | H | CH₃ | C₂H₅ | F | 3-methylthiophene | (S, S) |

TABLE 1-continued

Examples of compounds of the formula (I)

| Ex. No. | A | R¹ | R² | R³ | R⁴ | Y | Z | Physical data and stereochemical spec. |
|---|---|---|---|---|---|---|---|---|
| 243 | —CH₂—O—C₂H₅ | NH₂ | H | CH₃ | C₂H₅ | F | 3-methylthiophene | (R, S) |
| 244 | —CH₂CH₂CH₂— | NH₂ | H | CH₃ | CH₃ | F | 2-methylthiophene | (S, R) |
| 245 | —CH₂CH₂CH₂— | NH₂ | H | CH₃ | CH₃ | F | 2-methylthiophene | (R, R) |
| 246 | —CH₂CH₂CH₂— | NH₂ | H | CH₃ | CH₃ | F | 2-methylthiophene | (S, S) |
| 247 | —CH₂CH₂CH₂— | NH₂ | H | CH₃ | CH₃ | F | 2-methylthiophene | (R, S) |
| 248 | —CH₂CH₂CH₂— | NH₂ | H | CH₃ | C₂H₅ | F | 2-methylthiophene | (S, R) |
| 249 | —CH₂CH₂CH₂— | NH₂ | H | CH₃ | C₂H₅ | F | 2-methylthiophene | (R, R) |
| 250 | —CH₂CH₂CH₂— | NH₂ | H | CH₃ | C₂H₅ | F | 2-methylthiophene | (S, S) |
| 251 | —CH₂CH₂CH₂— | NH₂ | H | CH₃ | C₂H₅ | F | 2-methylthiophene | (R, S) |
| 252 | —CH₂CH₂CH₂— | NH₂ | H | CH₃ | CH₃ | F | 3-methylthiophene | (S, R) |

TABLE 1-continued

Examples of compounds of the formula (I)

| Ex. No. | A | R¹ | R² | R³ | R⁴ | Y | Z | Physical data and stereo-chemical spec. |
|---|---|---|---|---|---|---|---|---|
| 253 | -CH₂-CH₂- | NH₂ | H | CH₃ | CH₃ | F | 3-thienyl | (R, R) |
| 254 | -CH₂-CH₂- | NH₂ | H | CH₃ | CH₃ | F | 3-thienyl | (S, S) |
| 255 | -CH₂-CH₂- | NH₂ | H | CH₃ | CH₃ | F | 3-thienyl | (R, S) |
| 256 | -CH₂-CH₂- | NH₂ | H | CH₃ | C₂H₅ | F | 3-thienyl | (S, R) |
| 257 | -CH₂-CH₂- | NH₂ | H | CH₃ | C₂H₅ | F | 3-thienyl | (R, R) |
| 258 | -CH₂-CH₂- | NH₂ | H | CH₃ | C₂H₅ | F | 3-thienyl | (S, S) |
| 259 | -CH₂-CH₂- | NH₂ | H | CH₃ | C₂H₅ | F | 3-thienyl | (R, S) |
| 260 | -CH₂-CH₂- | NH₂ | H | CH₃ | CH₃ | Cl | 3-thienyl | (S, R) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 261 | -CH₂-CH₂-CH₂- | NH₂ | H | CH₃ | CH₃ | Cl | 3-methylthiophene | (R, R) |
| 262 | -CH₂-CH₂-CH₂- | NH₂ | H | CH₃ | CH₃ | Cl | 3-methylthiophene | (S, S) |
| 263 | -CH₂-CH₂-CH₂- | NH₂ | H | CH₃ | CH₃ | Cl | 3-methylthiophene | (R, S) |
| 264 | -CH₂-CH₂-CH₂- | NH₂ | H | CH₃ | C₂H₅ | Cl | 3-methylthiophene | (S, R) |
| 265 | -CH₂-CH₂-CH₂- | NH₂ | H | CH₃ | C₂H₅ | Cl | 3-methylthiophene | (R, R) |
| 266 | -CH₂-CH₂-CH₂- | NH₂ | H | CH₃ | C₂H₅ | Cl | 3-methylthiophene | (S, S) |
| 267 | -CH₂-CH₂-CH₂- | NH₂ | H | CH₃ | C₂H₅ | Cl | 3-methylthiophene | (R, S) |
| 268 | -CH₂-CH₂-CH₂- | NH₂ | H | CH₃ | CH₃ | OH | 2-methylthiophene | $[\alpha]_D^{20}$ = -5.8° (S, rac) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 269 | -CH₂-CH₂- | NH₂ | H | CH₃ | CH₃ | OH | 2-thienyl | $[\alpha]_D^{20}$ = +6.5° (R, rac) |
| 270 | -CH₂-CH₂- | NH₂ | H | CH₃ | CH₃ | Cl | 2-thienyl | (amorphous) (S, rac) |
| 271 | -CH₂-CH₂- | NH₂ | H | CH₃ | CH₃ | Cl | 2-thienyl | $[\alpha]_D^{20}$ = +6.5° (R, rac) |
| 272 | -CH₂-CH₂- | NH₂ | H | CH₃ | CH₃ | OH | 3-thienyl | (amorphous) (S, rac) |
| 273 | -CH₂-CH₂- | NH₂ | H | CH₃ | CH₃ | OH | 3-thienyl | $[\alpha]_D^{20}$ = +22° (R, rac) |
| 274 | -CH₂-CH₂- | NH₂ | H | CH₃ | CH₃ | Cl | 3-thienyl | $[\alpha]_D^{20}$ = -3.8° (S, rac) |
| 275 | -CH₂-CH₂- | NH₂ | H | CH₃ | CH₃ | Cl | 3-thienyl | $[\alpha]_D^{20}$ = +5.4° (R, rac) |
| 276 | -CH₂-O- | NH₂ | H | CH₃ | C₂H₅ | F | 3,5-difluorophenyl | (amorphous) (S, R) |

TABLE 1-continued

Examples of compounds of the formula (I)

| Ex. No. | A | R¹ | R² | R³ | R⁴ | Y | Z | Physical data and stereo-chemical spec. |
|---|---|---|---|---|---|---|---|---|
| 277 | —CH₂—O—CH₃ | NH₂ | H | CH₃ | C₂H₅ | F | 3,5-difluorophenyl | (amorphous) log p: 2.72[b.)] (R, R) |
| 278 | — | NH₂ | H | CH₃ | C₂H₅ | OH | phenyl | $[\alpha]_D^{20}$ = +108° (S, R) |
| 279 | — | NH₂ | H | CH₃ | C₂H₅ | OH | phenyl | $[\alpha]_D^{20}$ = +133° (R, R) |
| 280 | — | NH₂ | H | CH₃ | C₂H₅ | F | phenyl | $[\alpha]_D^{20}$ = +106° log p: 1.65[a.)] (S, R) |
| 281 | — | NH₂ | H | CH₃ | C₂H₅ | F | phenyl | $[\alpha]_D^{20}$ = +152° log p: 1.64[a.)] (R, R) |
| 282 | —CH₂—O—CH₃ | NH₂ | H | CH₃ | C₂H₅ | F | 2-chlorophenyl | (amorphous) (R, R) |
| 283 | —CH₂—O—CH₃ | NH₂ | H | CH₃ | C₂H₅ | F | 2-chlorophenyl | (amorphous) (S, R) |
| 284 | —CH₂—O—CH₃ | —C(=O)—NH—CH₃ | H | CH₃ | C₂H₅ | F | 3,5-dimethylphenyl | (R, R) |

TABLE 1-continued

Examples of compounds of the formula (I)

| Ex. No. | A | R¹ | R² | R³ | R⁴ | Y | Z | Physical data and stereo-chemical spec. |
|---|---|---|---|---|---|---|---|---|
| 285 | CH₂OCH₃ | C(=O)NH(CH₃), C₂H₅ | H | CH₃ | C₂H₅ | F | 3,5-dimethylphenyl | (R, R) |
| 286 | CH₂OCH₃ | CH=N(CH₃), N(CH₃)₂ | H | CH₃ | C₂H₅ | F | 3,5-dimethylphenyl | (R, R) |
| 287 | CH₂OCH₃ | NH₂ | H | CH₃ | C₂H₅ | F | 3,5-dimethylphenyl | (R, R) |
| 288 | CH₂OCH₃ | C(=O)NH(CH₃), CH₃ | H | CH₃ | C₂H₅ | F | 3,5-dimethylphenyl | (R, R) |
| 289 | CH₂OCH₃ | C(=O)NH(CH₃), CH₃ | H | CH₃ | C₂H₅ | F | 3,5-difluorophenyl | (R, R) |
| 290 | CH₂OCH₃ | C(=O)NH(CH₃), C₂H₅ | H | CH₃ | C₂H₅ | F | 3,5-difluorophenyl | (R, R) |
| 291 | CH₂OCH₃ | CH=N(CH₃), N(CH₃)₂ | H | CH₃ | C₂H₅ | F | 3,5-difluorophenyl | (R, R) |

TABLE 1-continued

Examples of compounds of the formula (I)

| Ex. No. | A | R¹ | R² | R³ | R⁴ | Y | Z | Physical data and stereo-chemical spec. |
|---|---|---|---|---|---|---|---|---|
| 292 | -CH₂-O-CH₃ | NH₂ | H | CH₃ | C₂H₅ | F | 3-methyl-phenyl-OCH₃ | (R, R) |
| 293 | -CH₂-O-CH₃ | -C(=O)(CH₃)NH-CH₃ | H | CH₃ | C₂H₅ | F | 3-methyl-phenyl-OCH₃ | (R, R) |
| 294 | -CH₂-O-CH₃ | -C(=O)(C₂H₅)NH-CH₃ | H | CH₃ | C₂H₅ | F | 3-methyl-phenyl-OCH₃ | (R, R) |
| 295 | -CH₂-O-CH₃ | NH₂ | H | CH₃ | C₂H₅ | F | 3,5-dichloro-phenyl | (R, R) |
| 296 | -CH₂-O-CH₃ | NH₂ | H | CH₃ | C₂H₅ | F | 3,5-dichloro-phenyl | (S, R) |
| 297 | -CH₂-O-CH₃ | -C(=O)(CH₃)NH-CH₃ | H | CH₃ | C₂H₅ | F | 3,5-dichloro-phenyl | (R, R) |

TABLE 1-continued

Examples of compounds of the formula (I)

| Ex. No. | A | R¹ | R² | R³ | R⁴ | Y | Z | Physical data and stereochemical spec. |
|---|---|---|---|---|---|---|---|---|
| 298 | –CH₂–O–CH₃ | C₂H₅–C(=O)–NH– | H | CH₃ | C₂H₅ | F | 3,5-dichlorophenyl | (R, R) |
| 299 | –CH₂–O–CH₃ | (CH₃)₂N–CH=N– | H | CH₃ | C₂H₅ | F | 3,5-dichlorophenyl | (R, R) |
| 300 | –CH₂–O–CH₃ | CH₃–C(=O)–NH– | H | CH₃ | C₂H₅ | F | 3-fluorophenyl | (R, R) |
| 301 | –CH₂–O–CH₃ | NH₂ | H | CH₃ | C₂H₅ | F | 3-chloro-2-methylphenyl | (R, R) |
| 302 | –CH₂–O–CH₃ | NH₂ | H | CH₃ | C₂H₅ | F | 3-nitrophenyl | (R, R) |
| 303 | –CH₂–O–CH₃ | NH₂ | H | CH₃ | C₂H₅ | F | 3-ethoxyphenyl | (R, R) |
| 304 | –CH₂–O–CH₃ | NH₂ | H | CH₃ | C₂H₅ | F | 3-chlorophenyl | (R, R) |

TABLE 1-continued

Examples of compounds of the formula (I)

| Ex. No. | A | R¹ | R² | R³ | R⁴ | Y | Z | Physical data and stereochemical spec. |
|---|---|---|---|---|---|---|---|---|
| 305 | -CH₂-O-CH₃ | NH₂ | H | CH₃ | C₂H₅ | F | 3-Cl-phenyl | (S, R) |
| 306 | -CH₂-O-CH₃ | NH₂ | H | CH₃ | C₂H₅ | F | 2-CH₃-4-F-phenyl | (R, R) |
| 307 | -CH₂-O-CH₃ | NH₂ | H | CH₃ | C₂H₅ | F | 2-CH₃-4-F-phenyl | (S, R) |
| 308 | -CH₂-O-CH₃ | CH₃C(O)NH- | H | CH₃ | C₂H₅ | F | 2-CH₃-4-F-phenyl | (R, R) |
| 309 | -CH₂-O-CH₃ | C₂H₅C(O)NH- | H | CH₃ | C₂H₅ | F | 2-CH₃-4-F-phenyl | (R, R) |
| 310 | — | NH₂ | H | CH₃ | CH₃ | F | 4-CH₃-phenyl | log p: 1.39[a] (R, R) |
| 311 | — | HC(O)NH- | H | CH₃ | CH₃ | F | 4-CH₃-phenyl | (R, R) |

TABLE 1-continued
Examples of compounds of the formula (I)
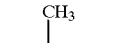
| Ex. No. | A | R¹ | R² | R³ | R⁴ | Y | Z | Physical data and stereo-chemical spec. |
|---|---|---|---|---|---|---|---|---|
| 312 | — | 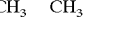 | H | CH₃ | CH₃ | F |  | (R, R) |
| 313 | — | 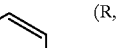 | H | CH₃ | CH₃ | F |  | (R, R) |
| 314 | — | 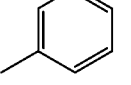 | H | CH₃ | CH₃ | F | 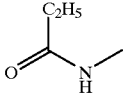 | (R, S) |
| 315 | — |  | H | CH₃ | CH₃ | F |  | (R, S) |
| 316 | — | 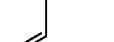 | H | CH₃ | CH₃ | F |  | (R, S) |
| 317 | — | NH₂ | H | CH₃ | CH₃ | F | 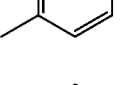 | (R, rac) |
| 318 | — | 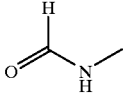 | H | CH₃ | CH₃ | F |  | (R, rac) |
| 319 | — |  | H | CH₃ | C₂H₅ | F | 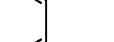 | log p: 2.52[a)] (R, R) |
| 320 | — |  | H | CH₃ | C₂H₅ | F | 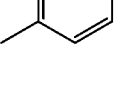 | (R, R) |

TABLE 1-continued

Examples of compounds of the formula (I)

| Ex. No. | A | R¹ | R² | R³ | R⁴ | Y | Z | Physical data and stereochemical spec. |
|---|---|---|---|---|---|---|---|---|
| 321 | — | C₂H₅-C(=O)-NH- | H | CH₃ | C₂H₅ | F | phenyl | log p: 2.70[a] (R, R) |
| 322 | — | NH₂ | H | CH₃ | C₂H₅ | F | phenyl | (R, R) |
| 323 | — | H-C(=O)-NH- | H | CH₃ | C₂H₅ | F | phenyl | (R, S) |
| 324 | — | CH₃-C(=O)-NH- | H | CH₃ | C₂H₅ | F | phenyl | (R, S) |
| 325 | — | C₂H₅-C(=O)-NH- | H | CH₃ | C₂H₅ | F | phenyl | (R, S) |
| 326 | — | n-C₃H₇-C(=O)-NH- | H | CH₃ | C₂H₅ | F | phenyl | (R, S) |
| 327 | — | NH₂ | H | CH₃ | C₂H₅ | F | phenyl | R, rac) |
| 328 | — | H-C(=O)-NH- | H | CH₃ | CH₃ | F | 4-Cl-phenyl | log p: 2.61[a] (R, R) |
| 329 | — | CH₃-C(=O)-NH- | H | CH₃ | CH₃ | F | 4-Cl-phenyl | (R, R) |

TABLE 1-continued

Examples of compounds of the formula (I)

| Ex. No. | A | R¹ | R² | R³ | R⁴ | Y | Z | Physical data and stereo-chemical spec. |
|---|---|---|---|---|---|---|---|---|
| 330 | — | C₂H₅-C(=O)-NH- | H | CH₃ | CH₃ | F | 4-Cl-C₆H₄- | log p: 2.79[a]<br>M.p.: 119° C.<br>(R, R) |
| 331 | — | i-C₃H₇-C(=O)-NH- | H | CH₃ | CH₃ | F | 4-Cl-C₆H₄- | (R, R) |
| 332 | — | H-C(=O)-NH- | H | CH₃ | CH₃ | F | 4-Cl-C₆H₄- | (R, S) |
| 333 | — | CH₃-C(=O)-NH- | H | CH₃ | CH₃ | F | 4-Cl-C₆H₄- | (R, S) |
| 334 | — | C₂H₅-C(=O)-NH- | H | CH₃ | CH₃ | F | 4-Cl-C₆H₄- | (R, S) |
| 335 | — | i-C₃H₇-C(=O)-NH- | H | CH₃ | CH₃ | F | 4-Cl-C₆H₄- | (R, S) |
| 336 | — | NH₂ | H | CH₃ | CH₃ | F | 4-Cl-C₆H₄- | (R, rac) |
| 337 | — | NH₂ | H | CH₃ | C₂H₅ | F | 4-Cl-C₆H₄- | (R, R) |
| 338 | — | H-C(=O)-NH- | H | CH₃ | C₂H₅ | F | 4-Cl-C₆H₄- | (R, R) |

TABLE 1-continued

Examples of compounds of the formula (I)

(I)

| Ex. No. | A | R¹ | R² | R³ | R⁴ | Y | Z | Physical data and stereochemical spec. |
|---|---|---|---|---|---|---|---|---|
| 339 | — | CH₃C(O)NH— | H | CH₃ | C₂H₅ | F | 4-Cl-C₆H₄— | (R, R) |
| 340 | — | C₂H₅C(O)NH— | H | CH₃ | C₂H₅ | F | 4-Cl-C₆H₄— | (R, R) |
| 341 | — | NH₂ | H | CH₃ | C₂H₅ | F | 4-Cl-C₆H₄— | (R, S) |
| 342 | — | HC(O)NH— | H | CH₃ | C₂H₅ | F | 4-Cl-C₆H₄— | (R, S) |
| 343 | — | CH₃C(O)NH— | H | CH₃ | C₂H₅ | F | 4-Cl-C₆H₄— | (R, S) |
| 344 | — | C₂H₅C(O)NH— | H | CH₃ | C₂H₅ | F | 4-Cl-C₆H₄— | (R, S) |
| 345 | — | NH₂ | H | CH₃ | C₂H₅ | F | 4-Cl-C₆H₄— | (R, rac) |
| 346 | — | NH₂ | H | CH₃ | C₂H₅ | F | 4-CH₃-C₆H₄— | (R, R) |
| 347 | — | HC(O)NH— | H | CH₃ | CH₃ | F | 4-CH₃-C₆H₄— | (R, R) |

TABLE 1-continued

Examples of compounds of the formula (I)

| Ex. No. | A | R¹ | R² | R³ | R⁴ | Y | Z | Physical data and stereochemical spec. |
|---|---|---|---|---|---|---|---|---|
| 348 | — | CH₃–C(=O)–NH– | H | CH₃ | CH₃ | F | 4-CH₃-C₆H₄– | (R, R) |
| 349 | — | C₂H₅–C(=O)–NH– | H | CH₃ | CH₃ | F | 4-CH₃-C₆H₄– | (R, R) |
| 350 | — | H–C(=O)–NH– | H | CH₃ | CH₃ | F | 4-CH₃-C₆H₄– | (R, S) |
| 351 | — | CH₃–C(=O)–NH– | H | CH₃ | CH₃ | F | 4-CH₃-C₆H₄– | (R, S) |
| 352 | — | C₂H₅–C(=O)–NH– | H | CH₃ | CH₃ | F | 4-CH₃-C₆H₄– | (R, S) |
| 353 | — | NH₂ | H | CH₃ | CH₃ | F | 4-CH₃-C₆H₄– | (R, rac) |
| 354 | — | NH₂ | H | CH₃ | C₂H₅ | F | 4-CH₃-C₆H₄– | (R, R) |
| 355 | — | H–C(=O)–NH– | H | CH₃ | C₂H₅ | F | 4-CH₃-C₆H₄– | (R, R) |
| 356 | — | CH₃–C(=O)–NH– | H | CH₃ | C₂H₅ | F | 4-CH₃-C₆H₄– | (R, R) |

TABLE 1-continued
Examples of compounds of the formula (I)
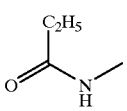
(I)
| Ex. No. | A | R¹ | R² | R³ | R⁴ | Y | Z | Physical data and stereo-chemical spec. |
|---|---|---|---|---|---|---|---|---|
| 357 | — | 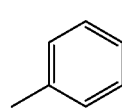 | H | CH₃ | C₂H₅ | F | 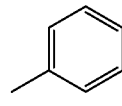 CH₃ | (R, R) |
| 368 | — | NH₂ | H | CH₃ | C₂H₅ | F | 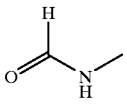 CH₃ | (R, S) |
| 359 | — | 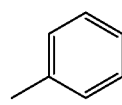 | H | CH₃ | C₂H₅ | F | 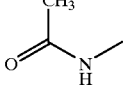 CH₃ | (R, S) |
| 360 | — | 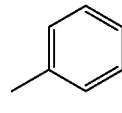 | H | CH₃ | C₂H₅ | F | 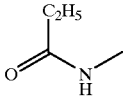 CH₃ | (R, S) |
| 361 | — | 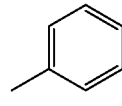 | H | CH₃ | C₂H₅ | F | 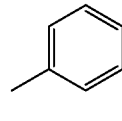 CH₃ | (R, S) |
| 362 | — | NH₂ | H | CH₃ | C₂H₅ | F | 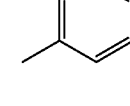 CH₃ | (R, rac) |
| 363 | — | NH₂ | H | CH₃ | CH₃ | F | 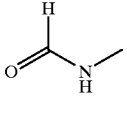 F | (R, R) |
| 364 | — | 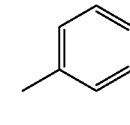 | H | CH₃ | CH₃ | F | 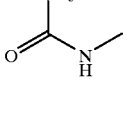 F | (R, R) |
| 365 | — | 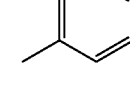 | H | CH₃ | CH₃ | F |  F | (R, R) |

TABLE 1-continued
Examples of compounds of the formula (I)
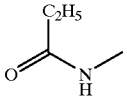
| Ex. No. | A | R¹ | R² | R³ | R⁴ | Y | Z | Physical data and stereo-chemical spec. |
|---|---|---|---|---|---|---|---|---|
| 366 | — | 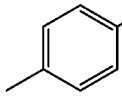 C₂H₅ | H | CH₃ | CH₃ | F | 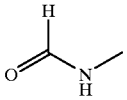 F | (R, R) |
| 367 | — | 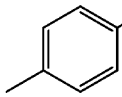 H | H | CH₃ | CH₃ | F | 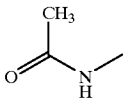 F | (R, S) |
| 368 | — | 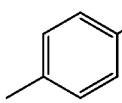 CH₃ | H | CH₃ | CH₃ | F | 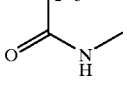 F | (R, S) |
| 369 | — | 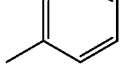 C₂H₅ | H | CH₃ | CH₃ | F | 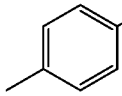 F | (R, S) |
| 370 | — | NH₂ | H | CH₃ | CH₃ | F | 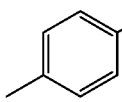 F | (R, rac) |
| 371 | — | NH₂ | H | CH₃ | C₂H₅ | F | 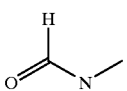 F | log p: 1.77[a]) (R, R) |
| 372 | — | 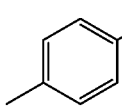 H | H | CH₃ | C₂H₅ | F | 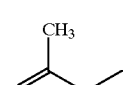 F | (R, R) |
| 373 | — | 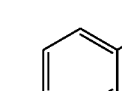 CH₃ | H | CH₃ | C₂H₅ | F | 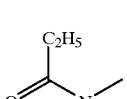 F | (R, R) |
| 374 | — | 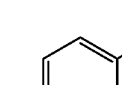 C₂H₅ | H | CH₃ | C₂H₅ | F | F | (R, R) |

TABLE 1-continued
Examples of compounds of the formula (I)
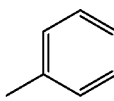
(I)
| Ex. No. | A | R¹ | R² | R³ | R⁴ | Y | Z | Physical data and stereochemical spec. |
|---|---|---|---|---|---|---|---|---|
| 375 | — | NH₂ | H | CH₃ | C₂H₅ | F | 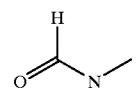 4-F-C₆H₄ | (R, S) |
| 376 | — | 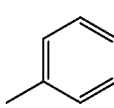 HC(O)NH– | H | CH₃ | C₂H₅ | F | 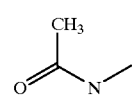 4-F-C₆H₄ | (R, S) |
| 377 | — | 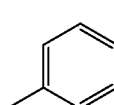 CH₃C(O)NH– | H | CH₃ | C₂H₅ | F | 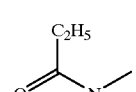 4-F-C₆H₄ | (R, S) |
| 378 | — | 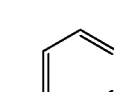 C₂H₅C(O)NH– | H | CH₃ | C₂H₅ | F | 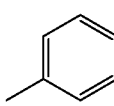 4-F-C₆H₄ | (R, S) |
| 379 | — | NH₂ | H | CH₃ | C₂H₅ | F | 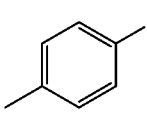 4-F-C₆H₄ | (R, rac) |
| 380 | — | NH₂ | H | CH₃ | CH₃ | F | 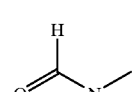 4-OCH₃-C₆H₄ | (R, R) |
| 381 | — | 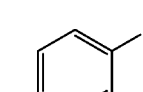 HC(O)NH– | H | CH₃ | CH₃ | F | 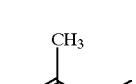 4-OCH₃-C₆H₄ | (R, R) |
| 382 | — | 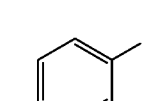 CH₃C(O)NH– | H | CH₃ | CH₃ | F | 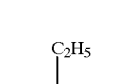 4-OCH₃-C₆H₄ | (R, R) |
| 383 | — | 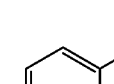 C₂H₅C(O)NH– | H | CH₃ | CH₃ | F | 4-OCH₃-C₆H₄ | (R, R) |

TABLE 1-continued

Examples of compounds of the formula (I)

| Ex. No. | A | R¹ | R² | R³ | R⁴ | Y | Z | Physical data and stereochemical spec. |
|---|---|---|---|---|---|---|---|---|
| 384 | — | HC(O)NH- | H | CH₃ | CH₃ | F | 4-OCH₃-C₆H₄- | (R, S) |
| 385 | — | CH₃C(O)NH- | H | CH₃ | CH₃ | F | 4-OCH₃-C₆H₄- | (R, S) |
| 386 | — | C₂H₅C(O)NH- | H | CH₃ | CH₃ | F | 4-OCH₃-C₆H₄- | (R, S) |
| 387 | — | NH₂ | H | CH₃ | CH₃ | F | 4-OCH₃-C₆H₄- | (R, rac) |
| 388 | — | NH₂ | H | CH₃ | C₂H₅ | F | 4-OCH₃-C₆H₄- | (R, R) |
| 389 | — | HC(O)NH- | H | CH₃ | C₂H₅ | F | 4-NO₂-C₆H₄- | (R, R) |
| 390 | — | CH₃C(O)NH- | H | CH₃ | C₂H₅ | F | 4-OCH₃-C₆H₄- | (R, R) |
| 391 | — | C₂H₅C(O)NH- | H | CH₃ | C₂H₅ | F | 4-OCH₃-C₆H₄- | (R, R) |
| 392 | — | NH₂ | H | CH₃ | C₂H₅ | F | 4-OCH₃-C₆H₄- | (R, S) |

TABLE 1-continued

Examples of compounds of the formula (I)

(I)

| Ex. No. | A | R¹ | R² | R³ | R⁴ | Y | Z | Physical data and stereochemical spec. |
|---|---|---|---|---|---|---|---|---|
| 393 | — | H-C(=O)-NH- | H | CH₃ | C₂H₅ | F | 4-OCH₃-C₆H₄- | (R, S) |
| 394 | — | CH₃-C(=O)-NH- | H | CH₃ | C₂H₅ | F | 4-OCH₃-C₆H₄- | (R, S) |
| 395 | — | C₂H₅-C(=O)-NH- | H | CH₃ | C₂H₅ | F | 4-OCH₃-C₆H₄- | (R, S) |
| 396 | — | NH₂ | H | CH₃ | C₂H₅ | F | 4-OCH₃-C₆H₄- | (R, rac) |
| 397 | — | NH₂ | H | CH₃ | CH₃ | F | 4-NO₂-C₆H₄- | (R, R) |
| 398 | — | H-C(=O)-NH- | H | CH₃ | CH₃ | F | 4-NO₂-C₆H₄- | (R, R) |
| 399 | — | CH₃-C(=O)-NH- | H | CH₃ | CH₃ | F | 4-NO₂-C₆H₄- | (R, R) |
| 400 | — | C₂H₅-C(=O)-NH- | H | CH₃ | CH₃ | F | 4-NO₂-C₆H₄- | (R, R) |
| 401 | — | NH₂ | H | CH₃ | CH₃ | F | 4-NO₂-C₆H₄- | (R, S) |

TABLE 1-continued

Examples of compounds of the formula (I)

(I)

| Ex. No. | A | R¹ | R² | R³ | R⁴ | Y | Z | Physical data and stereochemical spec. |
|---|---|---|---|---|---|---|---|---|
| 402 | — | H-C(=O)-NH- | H | CH₃ | CH₃ | F | 4-NO₂-C₆H₄- | (R, S) |
| 403 | — | CH₃-C(=O)-NH- | H | CH₃ | CH₃ | F | 4-NO₂-C₆H₄- | (R, S) |
| 404 | — | C₂H₅-C(=O)-NH- | H | CH₃ | CH₃ | F | 4-NO₂-C₆H₄- | (R, S) |
| 405 | — | NH₂ | H | CH₃ | CH₃ | F | 4-NO₂-C₆H₄- | (R, rac) |
| 406 | — | NH₂ | H | CH₃ | C₂H₅ | F | 4-NO₂-C₆H₄- | (R, R) |
| 407 | — | H-C(=O)-NH- | H | CH₃ | C₂H₅ | F | 4-NO₂-C₆H₄- | (R, R) |
| 408 | — | CH₃-C(=O)-NH- | H | CH₃ | C₂H₅ | F | 4-NO₂-C₆H₄- | (R, R) |
| 409 | — | C₂H₅-C(=O)-NH- | H | CH₃ | C₂H₅ | F | 4-NO₂-C₆H₄- | (R, R) |
| 410 | — | NH₂ | H | CH₃ | C₂H₅ | F | 4-NO₂-C₆H₄- | (R, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 411 | — | H-C(O)-NH- | H | CH₃ | C₂H₅ | F | 4-NO₂-C₆H₄- | (R, S) |
| 412 | — | CH₃-C(O)-NH- | H | CH₃ | C₂H₅ | F | 4-NO₂-C₆H₄- | (R, S) |
| 413 | — | C₂H₅-C(O)-NH- | H | CH₃ | C₂H₅ | F | 4-NO₂-C₆H₄- | (R, S) |
| 414 | — | NH₂ | H | CH₃ | C₂H₅ | F | 4-NO₂-C₆H₄- | (R, rac) |
| 415 | — | NH₂ | H | CH₃ | CH₃ | F | 4-CF₃-C₆H₄- | (R, R) |
| 416 | — | H-C(O)-NH- | H | CH₃ | CH₃ | F | 4-CF₃-C₆H₄- | (R, R) |
| 417 | — | CH₃-C(O)-NH- | H | CH₃ | CH₃ | F | 4-CF₃-C₆H₄- | (R, R) |
| 418 | — | C₂H₅-C(O)-NH- | H | CH₃ | CH₃ | F | 4-CF₃-C₆H₄- | (R, R) |
| 419 | — | NH₂ | H | CH₃ | CH₃ | F | 4-CF₃-C₆H₄- | (R, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 420 | — | CHO-NH- | H | CH₃ | CH₃ | F | 4-CF₃-C₆H₄- | (R, S) |
| 421 | — | CH₃CO-NH- | H | CH₃ | CH₃ | F | 4-CF₃-C₆H₄- | (R, S) |
| 422 | — | C₂H₅CO-NH- | H | CH₃ | CH₃ | F | 4-CF₃-C₆H₄- | (R, S) |
| 423 | — | NH₂ | H | CH₃ | CH₃ | F | 4-CF₃-C₆H₄- | (R, rac) |
| 424 | — | NH₂ | H | CH₃ | C₂H₅ | F | 4-CF₃-C₆H₄- | (R, R) |
| 425 | — | CHO-NH- | H | CH₃ | C₂H₅ | F | 4-CF₃-C₆H₄- | (R, R) |
| 426 | — | CH₃CO-NH- | H | CH₃ | C₂H₅ | F | 4-CF₃-C₆H₄- | (R, R) |
| 427 | — | C₂H₅CO-NH- | H | CH₃ | C₂H₅ | F | 4-CF₃-C₆H₄- | (R, R) |
| 428 | — | NH₂ | H | CH₃ | C₂H₅ | F | 4-CF₃-C₆H₄- | (R, S) |

TABLE 1-continued

Examples of compounds of the formula (I)

| Ex. No. | A | R¹ | R² | R³ | R⁴ | Y | Z | Physical data and stereochemical spec. |
|---|---|---|---|---|---|---|---|---|
| 429 | — | H-C(=O)-NH- | H | CH₃ | C₂H₅ | F | 4-CF₃-C₆H₄- | (R, S) |
| 430 | — | CH₃-C(=O)-NH- | H | CH₃ | C₂H₅ | F | 4-CF₃-C₆H₄- | (R, S) |
| 431 | — | C₂H₅-C(=O)-NH- | H | CH₃ | C₂H₅ | F | 4-CF₃-C₆H₄- | (R, S) |
| 432 | — | NH₂ | H | CH₃ | C₂H₅ | F | 4-CF₃-C₆H₄- | (R, rac) |
| 433 | — | NH₂ | H | CH₃ | CH₃ | F | 3-F-C₆H₄- | (R, R) |
| 434 | — | H-C(=O)-NH- | H | CH₃ | CH₃ | F | 3-F-C₆H₄- | (R, R) |
| 435 | — | CH₃-C(=O)-NH- | H | CH₃ | CH₃ | F | 3-F-C₆H₄- | (R, R) |
| 436 | — | C₂H₅-C(=O)-NH- | H | CH₃ | CH₃ | F | 3-F-C₆H₄- | (R, R) |

TABLE 1-continued
Examples of compounds of the formula (I)
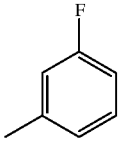
(I)
| Ex. No. | A | R¹ | R² | R³ | R⁴ | Y | Z | Physical data and stereo-chemical spec. |
|---|---|---|---|---|---|---|---|---|
| 437 | — | NH₂ | H | CH₃ | CH₃ | F | 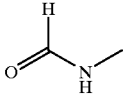 | (R, S) |
| 438 | — | 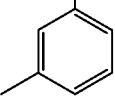 | H | CH₃ | CH₃ | F | 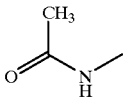 | (R, S) |
| 439 | — | 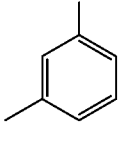 | H | CH₃ | CH₃ | F | 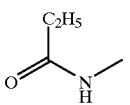 | (R, S) |
| 440 | — | 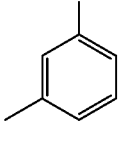 | H | CH₃ | CH₃ | F | 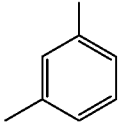 | (R, S) |
| 441 | — | NH₂ | H | CH₃ | CH₃ | F | 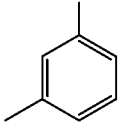 | (R, rac) |
| 442 | — | NH₂ | H | CH₃ | C₂H₅ | F | 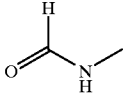 | (R, R) |
| 443 | — | 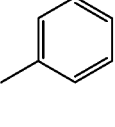 | H | CH₃ | C₂H₅ | F | 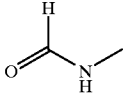 | (R, R) |

TABLE 1-continued

Examples of compounds of the formula (I)

| Ex. No. | A | R¹ | R² | R³ | R⁴ | Y | Z | Physical data and stereo-chemical spec. |
|---|---|---|---|---|---|---|---|---|
| 444 | — | CH₃–C(O)–NH– | H | CH₃ | C₂H₅ | F | 3-F-C₆H₄– | (R, R) |
| 445 | — | C₂H₅–C(O)–NH– | H | CH₃ | C₂H₅ | F | 3-F-C₆H₄– | (R, R) |
| 446 | — | NH₂ | H | CH₃ | C₂H₅ | F | 3-F-C₆H₄– | (R, S) |
| 447 | — | H–C(O)–NH– | H | CH₃ | C₂H₅ | F | 3-F-C₆H₄– | (R, S) |
| 448 | — | CH₃–C(O)–NH– | H | CH₃ | C₂H₅ | F | 3-F-C₆H₄– | (R, S) |
| 449 | — | C₂H₅–C(O)–NH– | H | CH₃ | C₂H₅ | F | 3-F-C₆H₄– | (R, S) |
| 450 | — | NH₂ | H | CH₃ | C₂H₅ | F | 3-F-C₆H₄– | (R, rac) |

TABLE 1-continued

Examples of compounds of the formula (I)

(I)

| Ex. No. | A | R¹ | R² | R³ | R⁴ | Y | Z | Physical data and stereo- chemical spec. |
|---|---|---|---|---|---|---|---|---|
| 451 | — | NH₂ | H | CH₃ | CH₃ | F | 2-F-C₆H₄ | (R, R) |
| 452 | — | HC(O)NH— | H | CH₃ | CH₃ | F | 2-F-C₆H₄ | (R, R) |
| 453 | — | CH₃C(O)NH— | H | CH₃ | CH₃ | F | 2-F-C₆H₄ | (R, R) |
| 454 | — | C₂H₅C(O)NH— | H | CH₃ | CH₃ | F | 2-F-C₆H₄ | (R, R) |
| 455 | — | NH₂ | H | CH₃ | CH₃ | F | 2-F-C₆H₄ | (R, S) |
| 456 | — | HC(O)NH— | H | CH₃ | CH₃ | F | 2-F-C₆H₄ | (R, S) |
| 457 | — | CH₃C(O)NH— | H | CH₃ | CH₃ | F | 2-F-C₆H₄ | (R, S) |

TABLE 1-continued

Examples of compounds of the formula (I)

| Ex. No. | A | R¹ | R² | R³ | R⁴ | Y | Z | Physical data and stereochemical spec. |
|---|---|---|---|---|---|---|---|---|
| 458 | — | C₂H₅-C(=O)-NH- | H | CH₃ | CH₃ | F | 2-F-C₆H₄-CH₂- | (R, S) |
| 459 | — | NH₂ | H | CH₃ | CH₃ | F | 2-F-C₆H₄-CH₂- | (R, rac) |
| 460 | — | NH₂ | H | CH₃ | C₂H₅ | F | 2-F-C₆H₄-CH₂- | (R, R) |
| 461 | — | H-C(=O)-NH- | H | CH₃ | C₂H₅ | F | 2-F-C₆H₄-CH₂- | (R, R) |
| 462 | — | CH₃-C(=O)-NH- | H | CH₃ | C₂H₅ | F | 2-F-C₆H₄-CH₂- | (R, R) |
| 463 | — | C₂H₅-C(=O)-NH- | H | CH₃ | C₂H₅ | F | 2-F-C₆H₄-CH₂- | (R, R) |

TABLE 1-continued
Examples of compounds of the formula (I)
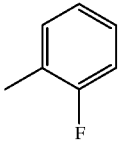
| Ex. No. | A | R¹ | R² | R³ | R⁴ | Y | Z | Physical data and stereo-chemical spec. |
|---|---|---|---|---|---|---|---|---|
| 464 | — | NH$_2$ | H | CH$_3$ | C$_2$H$_5$ | F | 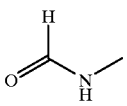 | (R, S) |
| 465 | — | 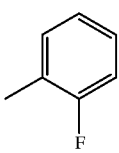 | H | CH$_3$ | C$_2$H$_5$ | F | 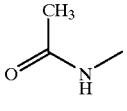 | (R, S) |
| 466 | — | 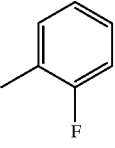 | H | CH$_3$ | C$_2$H$_5$ | F | 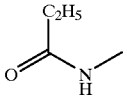 | (R, S) |
| 467 | — | 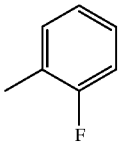 | H | CH$_3$ | C$_2$H$_5$ | F | 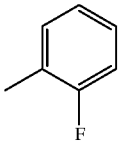 | (R, S) |
| 468 | — | NH$_2$ | H | CH$_3$ | C$_2$H$_5$ | F | 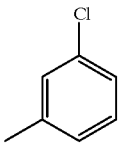 | (R, rac) |
| 469 | — | NH$_2$ | H | CH$_3$ | CH$_3$ | F | 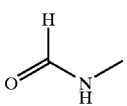 | (R, R) |
| 470 | — | 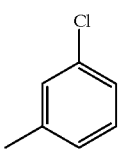 | H | CH$_3$ | CH$_3$ | F | | (R, R) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 471 | — | CH₃–C(O)–NH– | H | CH₃ | CH₃ | F | 3-Cl-C₆H₄– | (R, R) |
| 472 | — | C₂H₅–C(O)–NH– | H | CH₃ | CH₃ | F | 3-Cl-C₆H₄– | (R, R) |
| 473 | — | NH₂ | H | CH₃ | CH₃ | F | 3-Cl-C₆H₄– | (R, S) |
| 474 | — | H–C(O)–NH– | H | CH₃ | CH₃ | F | 3-Cl-C₆H₄– | (R, S) |
| 475 | — | CH₃–C(O)–NH– | H | CH₃ | CH₃ | F | 3-Cl-C₆H₄– | (R, S) |
| 476 | — | C₂H₅–C(O)–NH– | H | CH₃ | CH₃ | F | 3-Cl-C₆H₄– | (R, S) |
| 477 | — | NH₂ | H | CH₃ | CH₃ | F | 3-Cl-C₆H₄– | (R, rac) |

TABLE 1-continued
Examples of compounds of the formula (I)
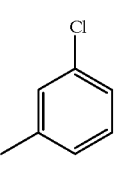
(I)
| Ex. No. | A | R¹ | R² | R³ | R⁴ | Y | Z | Physical data and stereo-chemical spec. |
|---|---|---|---|---|---|---|---|---|
| 478 | — | NH$_2$ | H | CH$_3$ | C$_2$H$_5$ | F | 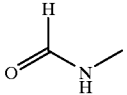 | (R, R) |
| 479 | — | 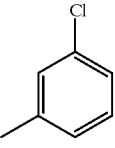 | H | CH$_3$ | C$_2$H$_5$ | F | 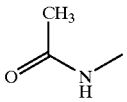 | (R, R) |
| 480 | — | 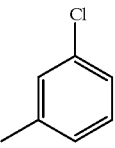 | H | CH$_3$ | C$_2$H$_5$ | F | 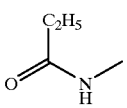 | (R, R) |
| 481 | — | 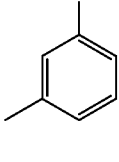 | H | CH$_3$ | C$_2$H$_5$ | F | 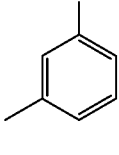 | (R, R) |
| 482 | — | NH$_2$ | H | CH$_3$ | C$_2$H$_5$ | F | 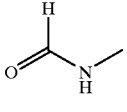 | (R, S) |
| 483 | — | 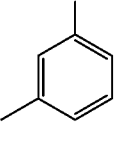 | H | CH$_3$ | C$_2$H$_5$ | F | 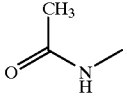 | (R, S) |
| 484 | — | 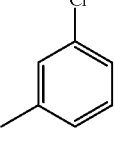 | H | CH$_3$ | C$_2$H$_5$ | F | | (R, S) |

TABLE 1-continued

Examples of compounds of the formula (I)

| Ex. No. | A | R¹ | R² | R³ | R⁴ | Y | Z | Physical data and stereo-chemical spec. |
|---|---|---|---|---|---|---|---|---|
| 485 | — | CH₃CH₂-C(=O)-NH- (with C₂H₅ branch) | H | CH₃ | C₂H₅ | F | 3-Cl-phenyl-CH₃ | (R, S) |
| 486 | — | NH₂ | H | CH₃ | C₂H₅ | F | 3-Cl-phenyl-CH₃ | (R, rac) |
| 487 | — | NH₂ | H | CH₃ | CH₃ | F | 3-OCH₃-phenyl-CH₃ | (R, R) |
| 488 | — | H-C(=O)-NH- | H | CH₃ | CH₃ | F | 3-OCH₃-phenyl-CH₃ | (R, R) |
| 489 | — | CH₃-C(=O)-NH- | H | CH₃ | CH₃ | F | 3-OCH₃-phenyl-CH₃ | (R, R) |
| 490 | — | C₂H₅-C(=O)-NH- | H | CH₃ | CH₃ | F | 3-OCH₃-phenyl-CH₃ | (R, R) |
| 491 | — | NH₂ | H | CH₃ | CH₃ | F | 3-OCH₃-phenyl-CH₃ | (R, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 492 | — | H-C(=O)-NH-CH₃ | H | CH₃ | CH₃ | F | 3-OCH₃-C₆H₄-CH₃ | (R, S) |
| 493 | — | CH₃-C(=O)-NH-CH₃ | H | CH₃ | CH₃ | F | 3-OCH₃-C₆H₄-CH₃ | (R, S) |
| 494 | — | C₂H₅-C(=O)-NH-CH₃ | H | CH₃ | CH₃ | F | 3-OCH₃-C₆H₄-CH₃ | (R, S) |
| 495 | — | NH₂ | H | CH₃ | CH₃ | F | 3-OCH₃-C₆H₄-CH₃ | (R, rac) |
| 496 | — | NH₂ | H | CH₃ | C₂H₅ | F | 3-OCH₃-C₆H₄-CH₃ | (R, R) |
| 497 | — | H-C(=O)-NH-CH₃ | H | CH₃ | C₂H₅ | F | 3-OCH₃-C₆H₄-CH₃ | (R, R) |
| 498 | — | CH₃-C(=O)-NH-CH₃ | H | CH₃ | C₂H₅ | F | 3-OCH₃-C₆H₄-CH₃ | (R, R) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 499 | — | C₂H₅-C(=O)-NH-CH₃ | H | CH₃ | C₂H₅ | F | 3-OCH₃-C₆H₄-CH₃ | (R, R) |
| 500 | — | NH₂ | H | CH₃ | C₂H₅ | F | 3-OCH₃-C₆H₄-CH₃ | (R, S) |
| 501 | — | H-C(=O)-NH-CH₃ | H | CH₃ | C₂H₅ | F | 3-OCH₃-C₆H₄-CH₃ | (R, S) |
| 502 | — | CH₃-C(=O)-NH-CH₃ | H | CH₃ | C₂H₅ | F | 3-OCH₃-C₆H₄-CH₃ | (R, S) |
| 503 | — | C₂H₅-C(=O)-NH-CH₃ | H | CH₃ | C₂H₅ | F | 3-OCH₃-C₆H₄-CH₃ | (R, S) |
| 504 | — | NH₂ | H | CH₃ | CH₃ | F | 3-OCH₃-C₆H₄-CH₃ | (R, rac) |
| 505 | — | NH₂ | H | CH₃ | CH₃ | F | 3-CH₃-C₆H₄-CH₃ | (R, R) |

TABLE 1-continued
Examples of compounds of the formula (I)
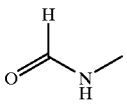
(I)
| Ex. No. | A | R¹ | R² | R³ | R⁴ | Y | Z | Physical data and stereo- chemical spec. |
|---|---|---|---|---|---|---|---|---|
| 506 | — | 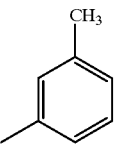 | H | CH₃ | CH₃ | F | 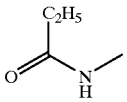 | (R, R) |
| 507 | — | 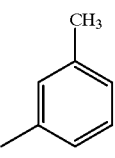 | H | CH₃ | CH₃ | F | 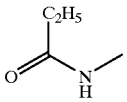 | (R, R) |
| 508 | — | 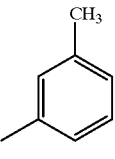 | H | CH₃ | CH₃ | F | 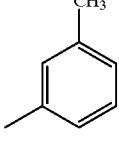 | (R, R) |
| 509 | — | NH₂ | H | CH₃ | CH₃ | F | 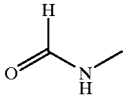 | (R, S) |
| 510 | — | 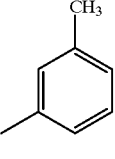 | H | CH₃ | CH₃ | F | 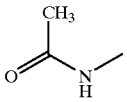 | (R, S) |
| 511 | — | 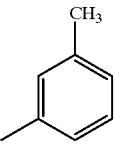 | H | CH₃ | CH₃ | F | 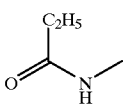 | (R, S) |
| 512 | — | 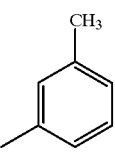 | H | CH₃ | CH₃ | F | | (R, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 513 | — | NH₂ | H | CH₃ | CH₃ | F | 3-methylphenyl | (R, rac) |
| 514 | — | NH₂ | H | CH₃ | C₂H₅ | F | 3-methylphenyl | (R, R) |
| 515 | — | HC(=O)NH– | H | CH₃ | C₂H₅ | F | 3-methylphenyl | (R, R) |
| 516 | — | CH₃C(=O)NH– | H | CH₃ | C₂H₅ | F | 3-methylphenyl | (R, R) |
| 517 | — | C₂H₅C(=O)NH– | H | CH₃ | C₂H₅ | F | 3-methylphenyl | (R, R) |
| 518 | — | NH₂ | H | CH₃ | C₂H₅ | F | 3-methylphenyl | (R, S) |
| 519 | — | HC(=O)NH– | H | CH₃ | C₂H₅ | F | 3-methylphenyl | (R, S) |

TABLE 1-continued

Examples of compounds of the formula (I)

(I)

| Ex. No. | A | R¹ | R² | R³ | R⁴ | Y | Z | Physical data and stereochemical spec. |
|---|---|---|---|---|---|---|---|---|
| 520 | — | CH₃-C(=O)-NH- | H | CH₃ | C₂H₅ | F | 3-methylphenyl | (R, S) |
| 521 | — | C₂H₅-C(=O)-NH- | H | CH₃ | C₂H₅ | F | 3-methylphenyl | (R, S) |
| 522 | — | NH₂ | H | CH₃ | C₂H₅ | F | 3-methylphenyl | (R, rac) |
| 523 | — | NH₂ | H | CH₃ | CH₃ | F | 2-methylphenyl | (R, R) |
| 524 | — | H-C(=O)-NH- | H | CH₃ | CH₃ | F | 2-methylphenyl | (R, R) |
| 525 | — | CH₃-C(=O)-NH- | H | CH₃ | CH₃ | F | 2-methylphenyl | (R, R) |

TABLE 1-continued

Examples of compounds of the formula (I)

| Ex. No. | A | R¹ | R² | R³ | R⁴ | Y | Z | Physical data and stereochemical spec. |
|---|---|---|---|---|---|---|---|---|
| 526 | — | C₂H₅-C(=O)-NH- | H | CH₃ | CH₃ | F | 2-methylphenyl | (R, R) |
| 527 | — | NH₂ | H | CH₃ | CH₃ | F | 2-methylphenyl | (R, S) |
| 528 | — | H-C(=O)-NH- | H | CH₃ | CH₃ | F | 2-methylphenyl | (R, S) |
| 529 | — | CH₃-C(=O)-NH- | H | CH₃ | CH₃ | F | 2-methylphenyl | (R, S) |
| 530 | — | C₂H₅-C(=O)-NH- | H | CH₃ | CH₃ | F | 2-methylphenyl | (R, S) |
| 531 | — | NH₂ | H | CH₃ | CH₃ | F | 2-methylphenyl | (R, rac) |

TABLE 1-continued
Examples of compounds of the formula (I)
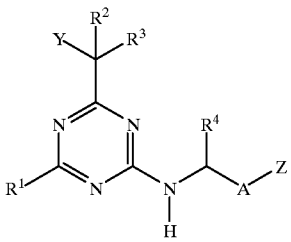
| Ex. No. | A | R$^1$ | R$^2$ | R$^3$ | R$^4$ | Y | Z | Physical data and stereo-chemical spec. |
|---|---|---|---|---|---|---|---|---|
| 532 | — | NH$_2$ | H | CH$_3$ | C$_2$H$_5$ | F | 2-methylphenyl | (R, R) |
| 533 | — | HC(O)NH— | H | CH$_3$ | C$_2$H$_5$ | F | 2-methylphenyl | (R, R) |
| 534 | — | CH$_3$C(O)NH— | H | CH$_3$ | C$_2$H$_5$ | F | 2-methylphenyl | (R, R) |
| 535 | — | C$_2$H$_5$C(O)NH— | H | CH$_3$ | C$_2$H$_5$ | F | 2-methylphenyl | (R, R) |
| 536 | — | NH$_2$ | H | CH$_3$ | C$_2$H$_5$ | F | 2-methylphenyl | (R, S) |
| 537 | — | HC(O)NH— | H | CH$_3$ | C$_2$H$_5$ | F | 2-methylphenyl | (R, S) |

TABLE 1-continued
Examples of compounds of the formula (I)
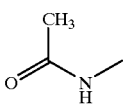
(I)
| Ex. No. | A | R¹ | R² | R³ | R⁴ | Y | Z | Physical data and stereo-chemical spec. |
|---|---|---|---|---|---|---|---|---|
| 538 | — | 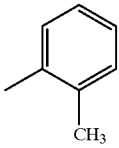 | H | CH₃ | C₂H₅ | F | 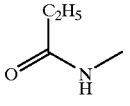 | (R, S) |
| 539 | — | 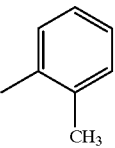 | H | CH₃ | C₂H₅ | F | 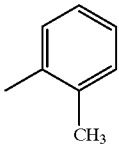 | (R, S) |
| 540 | — | NH₂ | H | CH₃ | C₂H₅ | F | 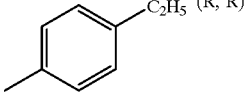 | (R, rac) |
| 541 | — | NH₂ | H | CH₃ | CH₃ | F | 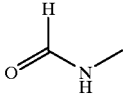 | (R, R) |
| 542 | — | 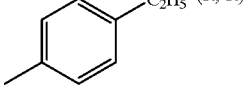 | H | CH₃ | CH₃ | F | 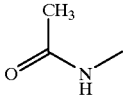 | (R, R) |
| 543 | — | 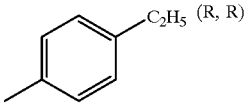 | H | CH₃ | CH₃ | F | 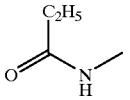 | (R, R) |
| 544 | — | 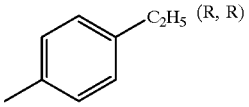 | H | CH₃ | CH₃ | F | 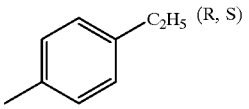 | (R, R) |
| 545 | — | NH₂ | H | CH₃ | CH₃ | F | C₂H₅ | (R, S) |

TABLE 1-continued

Examples of compounds of the formula (I)

| Ex. No. | A | R¹ | R² | R³ | R⁴ | Y | Z | Physical data and stereo-chemical spec. |
|---|---|---|---|---|---|---|---|---|
| 546 | — | H-C(=O)-NH-CH₃ (formamide) | H | CH₃ | CH₃ | F | 4-ethylphenyl | (R, S) |
| 547 | — | CH₃-C(=O)-NH-CH₃ | H | CH₃ | CH₃ | F | 4-ethylphenyl | (R, S) |
| 548 | — | C₂H₅-C(=O)-NH-CH₃ | H | CH₃ | CH₃ | F | 4-ethylphenyl | (R, S) |
| 549 | — | NH₂ | H | CH₃ | CH₃ | F | 4-ethylphenyl | (R, rac) |
| 550 | — | NH₂ | H | CH₃ | CH₃ | F | 2-thienyl | (R, R) |
| 551 | — | H-C(=O)-NH-CH₃ | H | CH₃ | CH₃ | F | 2-thienyl | (R, R) |
| 552 | — | CH₃-C(=O)-NH-CH₃ | H | CH₃ | CH₃ | F | 2-thienyl | (R, R) |
| 553 | — | C₂H₅-C(=O)-NH-CH₃ | H | CH₃ | CH₃ | F | 2-thienyl | (R, R) |
| 554 | — | NH₂ | H | CH₃ | CH₃ | F | 2-thienyl | (R, S) |

TABLE 1-continued

Examples of compounds of the formula (I)

| Ex. No. | A | R¹ | R² | R³ | R⁴ | Y | Z | Physical data and stereo-chemical spec. |
|---|---|---|---|---|---|---|---|---|
| 555 | — | H-C(=O)-NH-CH₃ | H | CH₃ | CH₃ | F | 2-thienyl | (R, S) |
| 556 | — | CH₃-C(=O)-NH-CH₃ | H | CH₃ | CH₃ | F | 2-thienyl | (R, S) |
| 557 | — | C₂H₅-C(=O)-NH-CH₃ | H | CH₃ | CH₃ | F | 2-thienyl | (R, S) |
| 558 | — | NH₂ | H | CH₃ | CH₃ | F | 2-thienyl | (R, rac) |
| 559 | — | H-C(=O)-NH-CH₃ | H | CH₃ | C₂H₅ | F | 2-thienyl | (R, R) |
| 560 | — | CH₃-C(=O)-NH-CH₃ | H | CH₃ | C₂H₅ | F | 2-thienyl | (R, R) |
| 561 | — | C₂H₅-C(=O)-NH-CH₃ | H | CH₃ | C₂H₅ | F | 2-thienyl | (R, R) |
| 562 | — | NH₂ | H | CH₃ | C₂H₅ | F | 2-thienyl | (R, S) |
| 563 | — | H-C(=O)-NH-CH₃ | H | CH₃ | C₂H₅ | F | 2-thienyl | (R, S) |

TABLE 1-continued

Examples of compounds of the formula (I)

(I)

| Ex. No. | A | R¹ | R² | R³ | R⁴ | Y | Z | Physical data and stereochemical spec. |
|---|---|---|---|---|---|---|---|---|
| 564 | — | CH₃-C(=O)-NH- | H | CH₃ | C₂H₅ | F | 2-thienyl | (R, S) |
| 565 | — | C₂H₅-C(=O)-NH- | H | CH₃ | C₂H₅ | F | 2-thienyl | (R, S) |
| 566 | — | NH₂ | H | CH₃ | C₂H₅ | F | 2-thienyl | (R, rac) |
| 567 | — | NH₂ | H | CH₃ | CH₃ | F | 3-thienyl | (R, R) |
| 568 | — | H-C(=O)-NH- | H | CH₃ | CH₃ | F | 3-thienyl | (R, R) |
| 569 | — | CH₃-C(=O)-NH- | H | CH₃ | CH₃ | F | 3-thienyl | (R, R) |
| 570 | — | C₂H₅-C(=O)-NH- | H | CH₃ | CH₃ | F | 3-thienyl | (R, R) |
| 571 | — | NH₂ | H | CH₃ | CH₃ | F | 3-thienyl | (R, S) |

TABLE 1-continued

Examples of compounds of the formula (I)

(I)

| Ex. No. | A | R¹ | R² | R³ | R⁴ | Y | Z | Physical data and stereo- chemical spec. |
|---|---|---|---|---|---|---|---|---|
| 572 | — | H-C(=O)-NH-CH₃ | H | CH₃ | CH₃ | F | 3-thienyl | (R, S) |
| 573 | — | CH₃-C(=O)-NH-CH₃ | H | CH₃ | CH₃ | F | 3-thienyl | (R, S) |
| 574 | — | C₂H₅-C(=O)-NH-CH₃ | H | CH₃ | CH₃ | F | 3-thienyl | (R, S) |
| 575 | — | NH₂ | H | CH₃ | CH₃ | F | 3-thienyl | (R, rac) |
| 576 | — | NH₂ | H | CH₃ | C₂H₅ | F | 3-thienyl | (R, R) |
| 577 | — | H-C(=O)-NH-CH₃ | H | CH₃ | C₂H₅ | F | 3-thienyl | (R, R) |
| 578 | — | CH₃-C(=O)-NH-CH₃ | H | CH₃ | C₂H₅ | F | 3-thienyl | (R, R) |
| 579 | — | C₂H₅-C(=O)-NH-CH₃ | H | CH₃ | C₂H₅ | F | 3-thienyl | (R, R) |

TABLE 1-continued

Examples of compounds of the formula (I)

(I)

| Ex. No. | A | R¹ | R² | R³ | R⁴ | Y | Z | Physical data and stereo- chemical spec. |
|---|---|---|---|---|---|---|---|---|
| 580 | — | NH₂ | H | CH₃ | C₂H₅ | F | 3-thienyl | (R, S) |
| 581 | — | HC(O)NH– | H | CH₃ | C₂H₅ | F | 3-thienyl | (R, S) |
| 582 | — | CH₃C(O)NH– | H | CH₃ | C₂H₅ | F | 3-thienyl | (R, S) |
| 583 | — | C₂H₅C(O)NH– | H | CH₃ | C₂H₅ | F | 3-thienyl | (R, S) |
| 584 | — | NH₂ | H | CH₃ | C₂H₅ | F | 3-thienyl | (R, rac) |
| 585 | — | NH₂ | H | CH₃ | CH₃ | F | 5-chloro-2-thienyl | (R, R) |
| 586 | — | HC(O)NH– | H | CH₃ | CH₃ | F | 5-chloro-2-thienyl | (R, R) |

TABLE 1-continued

Examples of compounds of the formula (I)

| Ex. No. | A | $R^1$ | $R^2$ | $R^3$ | $R^4$ | Y | Z | Physical data and stereo-chemical spec. |
|---|---|---|---|---|---|---|---|---|
| 587 | — | CH$_3$C(O)NH— | H | CH$_3$ | CH$_3$ | F | 5-chloro-2-methylthien-yl | (R, R) |
| 588 | — | C$_2$H$_5$C(O)NH— | H | CH$_3$ | CH$_3$ | F | 5-chloro-2-methylthien-yl | (R, R) |
| 589 | — | NH$_2$ | H | CH$_3$ | CH$_3$ | F | 5-chloro-2-methylthien-yl | (R, S) |
| 590 | — | HC(O)NH— | H | CH$_3$ | CH$_3$ | F | 5-chloro-2-methylthien-yl | (R, S) |
| 591 | — | CH$_3$C(O)NH— | H | CH$_3$ | CH$_3$ | F | 5-chloro-2-methylthien-yl | (R, S) |
| 592 | — | C$_2$H$_5$C(O)NH— | H | CH$_3$ | CH$_3$ | F | 5-chloro-2-methylthien-yl | (R, S) |

TABLE 1-continued
Examples of compounds of the formula (I)
(I)
| Ex. No. | A | R¹ | R² | R³ | R⁴ | Y | Z | Physical data and stereo-chemical spec. |
|---|---|---|---|---|---|---|---|---|
| 593 | — | NH₂ | H | CH₃ | CH₃ | F | 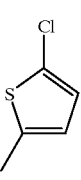 | (R, rac) |
| 594 | — | NH₂ | H | CH₃ | C₂H₅ | F | 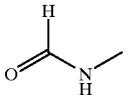 | (R, R) |
| 595 | — | 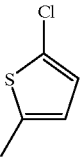 | H | CH₃ | C₂H₅ | F | 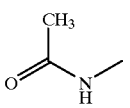 | (R, R) |
| 596 | — | 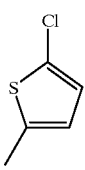 | H | CH₃ | C₂H₅ | F | 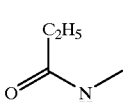 | (R, R) |
| 597 | — | 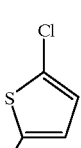 | H | CH₃ | C₂H₅ | F | 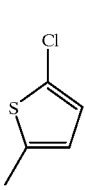 | (R, R) |
| 598 | — | NH₂ | H | CH₃ | C₂H₅ | F |  | (R, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 599 | — | H-C(=O)-NH-CH₃ | H | CH₃ | C₂H₅ | F | 5-Cl-thiophen-2-yl (5-methyl) | (R, S) |
| 600 | — | CH₃-C(=O)-NH-CH₃ | H | CH₃ | C₂H₅ | F | 5-Cl-thiophen-2-yl (5-methyl) | (R, S) |
| 601 | — | C₂H₅-C(=O)-NH-CH₃ | H | CH₃ | C₂H₅ | F | 5-Cl-thiophen-2-yl (5-methyl) | (R, S) |
| 602 | — | NH₂ | H | CH₃ | C₂H₅ | F | 5-Cl-thiophen-2-yl (5-methyl) | (R, rac) |
| 603 | — | NH₂ | H | CH₃ | CH₃ | F | 2,4-dimethylthiophen-yl | (R, R) |
| 604 | — | H-C(=O)-NH-CH₃ | H | CH₃ | CH₃ | F | 2,4-dimethylthiophen-yl | (R, R) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 605 | — | CH₃-C(=O)-NH- | H | CH₃ | CH₃ | F | 2-methyl-4-methylthiophen-... | (R, R) |
| 606 | — | C₂H₅-C(=O)-NH- | H | CH₃ | CH₃ | F | 2-methyl-4-methylthiophen-... | (R, R) |
| 607 | — | NH₂ | H | CH₃ | CH₃ | F | 2-methyl-4-methylthiophen-... | (R, S) |
| 608 | — | H-C(=O)-NH- | H | CH₃ | CH₃ | F | 2-methyl-4-methylthiophen-... | (R, S) |
| 609 | — | CH₃-C(=O)-NH- | H | CH₃ | CH₃ | F | 2-methyl-4-methylthiophen-... | (R, S) |
| 610 | — | C₂H₅-C(=O)-NH- | H | CH₃ | CH₃ | F | 2-methyl-4-methylthiophen-... | (R, S) |

TABLE 1-continued
Examples of compounds of the formula (I)
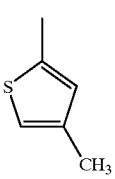
(I)
| Ex. No. | A | R¹ | R² | R³ | R⁴ | Y | Z | Physical data and stereo-chemical spec. |
|---|---|---|---|---|---|---|---|---|
| 611 | — | NH₂ | H | CH₃ | CH₃ | F | 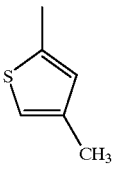 | (R, rac) |
| 612 | — | NH₂ | H | CH₃ | C₂H₅ | F | 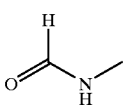 | (R, R) |
| 613 | — | 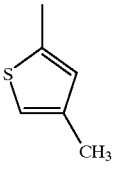 | H | CH₃ | C₂H₅ | F | 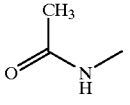 | (R, R) |
| 614 | — | 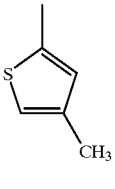 | H | CH₃ | C₂H₅ | F | 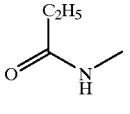 | (R, R) |
| 615 | — | 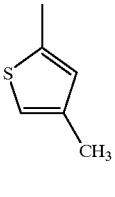 | H | CH₃ | C₂H₅ | F | 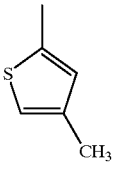 | (R, R) |
| 616 | — | NH₂ | H | CH₃ | C₂H₅ | F | | (R, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 617 | — | H-C(=O)-NH-CH₃ | H | CH₃ | C₂H₅ | F | 2,4-dimethylthiophen-5-yl | (R, S) |
| 618 | — | CH₃-C(=O)-NH-CH₃ | H | CH₃ | C₂H₅ | F | 2,4-dimethylthiophen-5-yl | (R, S) |
| 619 | — | C₂H₅-C(=O)-NH-CH₃ | H | CH₃ | C₂H₅ | F | 2,4-dimethylthiophen-5-yl | (R, S) |
| 620 | — | NH₂ | H | CH₃ | C₂H₅ | F | 2,4-dimethylthiophen-5-yl | (R, rac) |
| 621 | -CH₂-CH₂- | H-C(=O)-NH-CH₃ | H | CH₃ | CH₃ | F | 2-methylthiophen-5-yl | (R, R) |
| 622 | -CH₂-CH₂- | CH₃-C(=O)-NH-CH₃ | H | CH₃ | CH₃ | F | 2-methylthiophen-5-yl | (R, R) |
| 623 | -CH₂-CH₂- | C₂H₅-C(=O)-NH-CH₃ | H | CH₃ | CH₃ | F | 2-methylthiophen-5-yl | (R, R) |

TABLE 1-continued

Examples of compounds of the formula (I)

| Ex. No. | A | R¹ | R² | R³ | R⁴ | Y | Z | Physical data and stereochemical spec. |
|---|---|---|---|---|---|---|---|---|
| 624 | -CH₂-CH₂- | H-C(=O)-NH- | H | CH₃ | CH₃ | F | 2-thienyl | (R, S) |
| 625 | -CH₂-CH₂- | CH₃-C(=O)-NH- | H | CH₃ | CH₃ | F | 2-thienyl | (R, S) |
| 626 | -CH₂-CH₂- | C₂H₅-C(=O)-NH- | H | CH₃ | CH₃ | F | 2-thienyl | (R, S) |
| 627 | -CH₂-CH₂- | NH₂ | H | CH₃ | CH₃ | F | 2-thienyl | (R, rac) |
| 628 | -CH₂-CH₂- | H-C(=O)-NH- | H | CH₃ | C₂H₅ | F | 2-thienyl | (R, R) |
| 629 | -CH₂-CH₂- | CH₃-C(=O)-NH- | H | CH₃ | C₂H₅ | F | 2-thienyl | (R, R) |
| 630 | -CH₂-CH₂- | C₂H₅-C(=O)-NH- | H | CH₃ | C₂H₅ | F | 2-thienyl | (R, R) |
| 631 | -CH₂-CH₂- | H-C(=O)-NH- | H | CH₃ | C₂H₅ | F | 2-thienyl | (R, S) |
| 632 | -CH₂-CH₂- | CH₃-C(=O)-NH- | H | CH₃ | C₂H₅ | F | 2-thienyl | (R, S) |

TABLE 1-continued

Examples of compounds of the formula (I)

| Ex. No. | A | R¹ | R² | R³ | R⁴ | Y | Z | Physical data and stereo-chemical spec. |
|---|---|---|---|---|---|---|---|---|
| 633 | –CH₂CH₂CH₂– | C(=O)(C₂H₅)NH(CH₃) | H | CH₃ | C₂H₅ | F | 2-methylthiophene | (R, S) |
| 634 | –CH₂CH₂CH₂– | NH₂ | H | CH₃ | C₂H₅ | F | 2-methylthiophene | (R, rac) |
| 635 | –CH₂CH₂CH₂– | C(=O)(H)NH(CH₃) | H | CH₃ | CH₃ | F | 3-methylthiophene | (R, R) |
| 636 | –CH₂CH₂CH₂– | C(=O)(CH₃)NH(CH₃) | H | CH₃ | CH₃ | F | 3-methylthiophene | (R, R) |
| 637 | –CH₂CH₂CH₂– | C(=O)(C₂H₅)NH(CH₃) | H | CH₃ | CH₃ | F | 3-methylthiophene | (R, R) |
| 638 | –CH₂CH₂CH₂– | C(=O)(H)NH(CH₃) | H | CH₃ | CH₃ | F | 3-methylthiophene | (R, S) |
| 639 | –CH₂CH₂CH₂– | C(=O)(CH₃)NH(CH₃) | H | CH₃ | CH₃ | F | 3-methylthiophene | (R, S) |
| 640 | –CH₂CH₂CH₂– | C(=O)(C₂H₅)NH(CH₃) | H | CH₃ | CH₃ | F | 3-methylthiophene | (R, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 641 | -CH₂-CH-CH₂- | NH₂ | H | CH₃ | CH₃ | F | 3-thienyl | (R, rac) |
| 642 | -CH₂-CH-CH₂- | HC(O)NH- | H | CH₃ | C₂H₅ | F | 3-thienyl | (R, R) |
| 643 | -CH₂-CH-CH₂- | CH₃C(O)NH- | H | CH₃ | C₂H₅ | F | 3-thienyl | (R, R) |
| 644 | -CH₂-CH-CH₂- | C₂H₅C(O)NH- | H | CH₃ | C₂H₅ | F | 3-thienyl | (R, R) |
| 645 | -CH₂-CH-CH₂- | HC(O)NH- | H | CH₃ | C₂H₅ | F | 3-thienyl | (R, S) |
| 646 | -CH₂-CH-CH₂- | CH₃C(O)NH- | H | CH₃ | C₂H₅ | F | 3-thienyl | (R, S) |
| 647 | -CH₂-CH-CH₂- | C₂H₅C(O)NH- | H | CH₃ | C₂H₅ | F | 3-thienyl | (R, S) |
| 648 | -CH₂-CH-CH₂- | NH₂ | H | CH₃ | C₂H₅ | F | 3-thienyl | (R, rac) |

TABLE 1-continued

Examples of compounds of the formula (I)

| Ex. No. | A | R¹ | R² | R³ | R⁴ | Y | Z | Physical data and stereo-chemical spec. |
|---|---|---|---|---|---|---|---|---|
| 649 | –CH₂CH₂CH₂– | NH₂ | H | CH₃ | CH₃ | F | 2-methyl-3-thienyl | (R, R) |
| 650 | –CH₂CH₂CH₂– | HC(O)NH– | H | CH₃ | CH₃ | F | 2-methyl-3-thienyl | (R, R) |
| 651 | –CH₂CH₂CH₂– | CH₃C(O)NH– | H | CH₃ | CH₃ | F | 2-methyl-3-thienyl | (R, R) |
| 652 | –CH₂CH₂CH₂– | C₂H₅C(O)NH– | H | CH₃ | CH₃ | F | 2-methyl-3-thienyl | (R, R) |
| 653 | –CH₂CH₂CH₂– | NH₂ | H | CH₃ | CH₃ | F | 2-methyl-3-thienyl | (R, S) |
| 654 | –CH₂CH₂CH₂– | HC(O)NH– | H | CH₃ | CH₃ | F | 2-methyl-3-thienyl | (R, S) |
| 655 | –CH₂CH₂CH₂– | CH₃C(O)NH– | H | CH₃ | CH₃ | F | 2-methyl-3-thienyl | (R, S) |
| 656 | –CH₂CH₂CH₂– | C₂H₅C(O)NH– | H | CH₃ | CH₃ | F | 2-methyl-3-thienyl | (R, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 657 | -CH₂-CH₂-CH₂- | NH₂ | H | CH₃ | CH₃ | F | 2-methyl-3-thienyl (H₃C on 3-position) | (R, rac) |
| 658 | -CH₂-CH₂-CH₂- | NH₂ | H | CH₃ | C₂H₅ | F | 2-methyl-3-thienyl | (R, R) |
| 659 | -CH₂-CH₂-CH₂- | HC(=O)NH- | H | CH₃ | C₂H₅ | F | 2-methyl-3-thienyl | (R, R) |
| 660 | -CH₂-CH₂-CH₂- | CH₃C(=O)NH- | H | CH₃ | C₂H₅ | F | 2-methyl-3-thienyl | (R, R) |
| 661 | -CH₂-CH₂-CH₂- | C₂H₅C(=O)NH- | H | CH₃ | C₂H₅ | F | 2-methyl-3-thienyl | (R, R) |
| 662 | -CH₂-CH₂-CH₂- | NH₂ | H | CH₃ | C₂H₅ | F | 2-methyl-3-thienyl | (R, S) |
| 663 | -CH₂-CH₂-CH₂- | HC(=O)NH- | H | CH₃ | C₂H₅ | F | 2-methyl-3-thienyl | (R, S) |
| 664 | -CH₂-CH₂-CH₂- | CH₃C(=O)NH- | H | CH₃ | C₂H₅ | F | 2-methyl-3-thienyl | (R, S) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 665 | -CH₂-CH(-)-CH₂- | C₂H₅-C(=O)-NH- | H | CH₃ | C₂H₅ | F | 2-methyl-3-methylthiophene | (R, S) |
| 666 | -CH₂-CH(-)-CH₂- | NH₂ | H | CH₃ | C₂H₅ | F | 2-methyl-3-methylthiophene | (R, rac) |
| 667 | -CH₂-CH(-)-CH₂- | H-C(=O)-NH- | H | CH₃ | CH₃ | F | tolyl | (R, R) |
| 668 | -CH₂-CH(-)-CH₂- | CH₃-C(=O)-NH- | H | CH₃ | CH₃ | F | tolyl | (R, R) |
| 669 | -CH₂-CH(-)-CH₂- | C₂H₅-C(=O)-NH- | H | CH₃ | CH₃ | F | tolyl | (R, R) |
| 670 | -CH₂-CH(-)-CH₂- | H-C(=O)-NH- | H | CH₃ | CH₃ | F | tolyl | (S, R) |
| 671 | -CH₂-CH(-)-CH₂- | CH₃-C(=O)-NH- | H | CH₃ | CH₃ | F | tolyl | (S, R) |
| 672 | -CH₂-CH(-)-CH₂- | C₂H₅-C(=O)-NH- | H | CH₃ | CH₃ | F | tolyl | (S, R) |
| 673 | -CH₂-CH(-)-CH₂- | NH₂ | H | CH₃ | CH₃ | F | tolyl | (R, rac) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 674 | -CH₂-CH₂- | HC(O)NH- | H | CH₃ | C₂H₅ | F | phenyl-CH₃ | (R, R) |
| 675 | -CH₂-CH₂- | CH₃C(O)NH- | H | CH₃ | C₂H₅ | F | phenyl-CH₃ | (R, R) |
| 676 | -CH₂-CH₂- | C₂H₅C(O)NH- | H | CH₃ | C₂H₅ | F | phenyl-CH₃ | (R, R) |
| 677 | -CH₂-CH₂- | HC(O)NH- | H | CH₃ | C₂H₅ | F | phenyl-CH₃ | (S, R) |
| 678 | -CH₂-CH₂- | CH₃C(O)NH- | H | CH₃ | C₂H₅ | F | phenyl-CH₃ | (S, R) |
| 679 | -CH₂-CH₂- | C₂H₅C(O)NH- | H | CH₃ | C₂H₅ | F | phenyl-CH₃ | (S, R) |
| 680 | -CH₂-CH₂- | NH₂ | H | CH₃ | C₂H₅ | F | phenyl-CH₃ | (R, rac) |
| 681 | -CH₂-CH₂- | NH₂ | H | CH₃ | CH₃ | F | 3,5-di-CH₃-phenyl | (R, R) |
| 682 | -CH₂-CH₂- | HC(O)NH- | H | CH₃ | CH₃ | F | 3,5-di-CH₃-phenyl | (R, R) |

TABLE 1-continued

Examples of compounds of the formula (I)

(I)

| Ex. No. | A | $R^1$ | $R^2$ | $R^3$ | $R^4$ | Y | Z | Physical data and stereo-chemical spec. |
|---|---|---|---|---|---|---|---|---|
| 683 | –CH$_2$–CH(–)–CH$_2$– | –C(=O)–NH–CH$_3$ | H | CH$_3$ | CH$_3$ | F | 3-CH$_3$–C$_6$H$_4$– | (R, R) |
| 684 | –CH$_2$–CH(–)–CH$_2$– | –C(C$_2$H$_5$)(=O)–NH–CH$_3$ | H | CH$_3$ | CH$_3$ | F | 3-CH$_3$–C$_6$H$_4$– | (R, R) |
| 685 | –CH$_2$–CH(–)–CH$_2$– | NH$_2$ | H | CH$_3$ | CH$_3$ | F | 3-CH$_3$–C$_6$H$_4$– | (S, R) |
| 686 | –CH$_2$–CH(–)–CH$_2$– | –CH(=O)–NH–CH$_3$ | H | CH$_3$ | CH$_3$ | F | 3-CH$_3$–C$_6$H$_4$– | (S, R) |
| 687 | –CH$_2$–CH(–)–CH$_2$– | –C(CH$_3$)(=O)–NH–CH$_3$ | H | CH$_3$ | CH$_3$ | F | 3-CH$_3$–C$_6$H$_4$– | (S, R) |
| 688 | –CH$_2$–CH(–)–CH$_2$– | –C(C$_2$H$_5$)(=O)–NH–CH$_3$ | H | CH$_3$ | CH$_3$ | F | 3-CH$_3$–C$_6$H$_4$– | (S, R) |
| 689 | –CH$_2$–CH(–)–CH$_2$– | NH$_2$ | H | CH$_3$ | CH$_3$ | F | 3-CH$_3$–C$_6$H$_4$– | (R, rac) |

TABLE 1-continued

Examples of compounds of the formula (I)

| Ex. No. | A | $R^1$ | $R^2$ | $R^3$ | $R^4$ | Y | Z | Physical data and stereo-chemical spec. |
|---|---|---|---|---|---|---|---|---|
| 690 | –CH$_2$CH$_2$– | NH$_2$ | H | CH$_3$ | CH$_3$ | F | 3-F-C$_6$H$_4$ | (R, R) |
| 691 | –CH$_2$CH$_2$– | NHCHO | H | CH$_3$ | CH$_3$ | F | 3-F-C$_6$H$_4$ | (R, R) |
| 692 | –CH$_2$CH$_2$– | NHC(O)CH$_3$ | H | CH$_3$ | CH$_3$ | F | 3-F-C$_6$H$_4$ | (R, R) |
| 693 | –CH$_2$CH$_2$– | NHC(O)C$_2$H$_5$ | H | CH$_3$ | CH$_3$ | F | 3-F-C$_6$H$_4$ | (R, R) |
| 694 | –CH$_2$CH$_2$– | NH$_2$ | H | CH$_3$ | CH$_3$ | F | 3-F-C$_6$H$_4$ | (S, R) |
| 695 | –CH$_2$CH$_2$– | NHCHO | H | CH$_3$ | CH$_3$ | F | 3-F-C$_6$H$_4$ | (S, R) |

TABLE 1-continued

Examples of compounds of the formula (I)

(I)

| Ex. No. | A | R¹ | R² | R³ | R⁴ | Y | Z | Physical data and stereo-chemical spec. |
|---|---|---|---|---|---|---|---|---|
| 696 | –CH₂–CH₂– | CH₃–C(=O)–N(H)–CH₃ | H | CH₃ | CH₃ | F | 3-F-phenyl | (S, R) |
| 697 | –CH₂–CH₂– | C₂H₅–C(=O)–N(H)–CH₃ | H | CH₃ | CH₃ | F | 3-F-phenyl | (S, R) |
| 698 | –CH₂–CH₂– | NH₂ | H | CH₃ | CH₃ | F | 3-F-phenyl | (R, rac) |

The log p values given in Table 1 were determined in accordance with EEC Directive 79/831 Annex V.A8 by HPLC (High Performance Liquid Chromatography) using a reversed phase column (C 18). Temperature: 43° C.

a) Mobile phases for the determination in the acidic range: 0.1% aqueous phosphoric acid, acetonitrile; linear gradient from 10% acetonitrile to 90% acetonitrile—the corresponding data in Table 1 are marked a)

b) mobile phases for the determination in the neutral range: 0.01 molar aqueous phosphate buffer solution, acetonitrile; linear gradient from 10% acetonitrile to 90% acetonitrile—corresponding data in Table 1 are marked $^{b}$)

Calibration was carried out using unbranched alkan-2-ones (having 3 to 16 carbon atoms) with known log p values (determination of the log p values by the retention times using linear interpolation between two successive alkanones).

The lambda max values were determined using the UV spectra from 200 nm to 400 nm in the maxima of the chromatographic signals.

Starting Materials of the Formula (II)

Example (II-1)

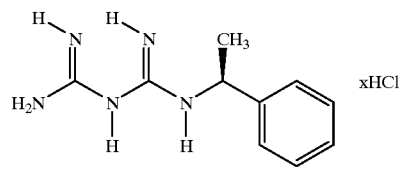

At room temperature, 72 g of hydrochloric acid (33% strength) are added with stirring to a solution of 81 g (0.60 mol) of (S)-1-phenyl-ethylamine in 150 ml of methanol. The mixture is diluted with toluene to about three times its original volume and the volatile components are carefully distilled off under waterpump vacuum. After addition of 50.4 g (0.60 mol) of cyanoguanidine, the residue is fused at from 150° C. to 170° C. (internal temperature; bath temperature about 200° C.) for three hours.

This gives 142 g (98% of theory) of (S)-1-(1-phenyl-ethyl)-biguanide hydrochloride as a glass-like material which can be used without further purification for the reaction according to the process according to the invention (cf. Example 1).

The compound (S)-1-(1-phenyl-propyl)-biguanide hydrochloride can be prepared analogously to Example (II-1) starting from (S)-1-phenyl-propylamine.

Starting Materials of the Formula (III):

Example (III-1)

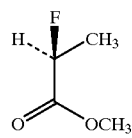

Step 1

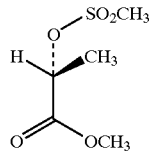

Over a period of 15 minutes, 34.3 g (0.30 mol) of methanesulphonyl chloride are added a little at a time and with stirring to a solution, cooled with ice, of 27.9 g (0.29 mol) of methyl (R)-lactate in 100 ml of pyridine. The reaction mixture is stirred at 5° C. for two hours, and then added to 100 ml of water and the mixture is extracted three times within each case 100 ml of methyl t-butyl ether (MTBE). The combined MTBE, phases are washed with ice-cold 6N hydrochloric acid (2×100 ml), with water (2×100 ml) and with ice-cold sodium bicarbonate solution (3×100 ml), dried with sodium sulphate and filtered. The filtrate is stirred with activated carbon (Norit A) for 30 minutes and filtered once more. From the filtrate, the solvent is carefully distilled off under waterpump vacuum.

This gives methyl (R)-α-methylsulphonyloxy-propionate as an amorphous residue which can be reacted without further purification according to the description of step 2 (below).

Step 2

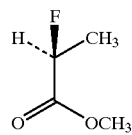

With stirring, 18.8 g (0.32 mol) of potassium fluoride are added to a mixture, heated to 125° C., of 47.9 g (0.26 mol) of methyl (R)-α-methylsulphonyloxy-propionate and 250 g of acetamide. 8 ml of a 1 molar solution of tetrabutylammonium fluoride in tetrahydrofuran are then added dropwise to the mixture. The reaction mixture is then stirred at 125° C. for 5 hours and at room temperature (approximately 20° C.) for 15 hours, then heated to 90° C. and admixed with vigorous stirring with 250 ml of water. After cooling to room temperature, the mixture is extracted three times with in each case 250 ml of dichloromethane. The combined organic phases are washed with saturated aqueous sodium chloride solution (2×100 ml) and then with water (1×100 ml), dried with sodium sulphate and filtered. The filtrate is stirred with activated carbon for 30 minutes and filtered once more. From the filtrate, the solvent is then carefully distilled off under waterpump vacuum. This gives methyl (S)-α-fluoro-propionate as an amorphous residue which can be used without further purification for the reaction according to the process according to the invention (cf. Example 1).

The compound methyl (R)-α-fluoro-propionate can be prepared analogously to Example (III-1) starting from methyl (S)-lactate.

USE EXAMPLE

Example A

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, for example, the compounds of Preparation Example 1, 18, 19, 22 and 23 exhibit strong activity against weeds.

TABLE A-1

Post-emergence test/greenhouse

| Active compound of Preparation Example No. | Application rate (g of ai./ha) | Setaria | Abutilon | Amaranthus | Xanthium |
|---|---|---|---|---|---|
| 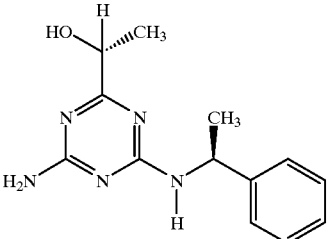 (1) | 1000 | 90 | 80 | 100 | 95 |

TABLE A-2

Post-emergence test/greenhouse

| Active compound of Preparation Example No. | Application rate (g of ai./ha) | Avena fatua | Setaria | Abutilon | Amaranthus | Galium | Sinapis | Xanthium |
|---|---|---|---|---|---|---|---|---|
| 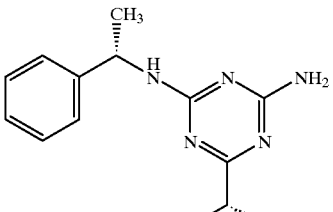 (19) | 1000 | 95 | 100 | 100 | 100 | 100 | 100 | 100 |

TABLE A-3

Post-emergence test/greenhouse

| Active compound of Preparation Example No. | Application rate (g of ai./ha) | Setaria | Abutilon | Amaranthus | Sinapis | Xanthium |
|---|---|---|---|---|---|---|
| 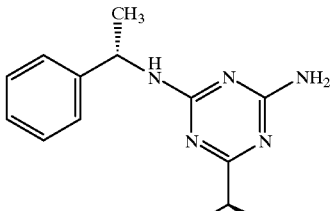 (18) | 1000 | 100 | 100 | 100 | 100 | 100 |
| 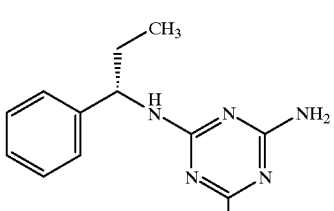 (22) | 1000 | 95 | 95 | 100 | 100 | 100 |

TABLE A-3-continued

Post-emergence test/greenhouse

| Active compound of Preparation Example No. | Application rate (g of ai./ha) | Setaria | Abutilon | Amaranthus | Sinapis | Xanthium |
|---|---|---|---|---|---|---|
| 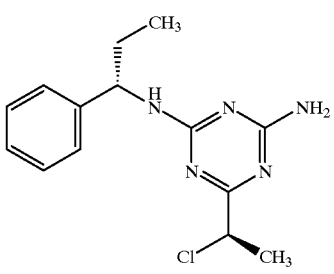 (23) | 1000 | 80 | 95 | 100 | 100 | 100 |

Example B

Pre-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)
100%=total destruction

In this test, for example, the compound of Preparation Example 1 exhibits strong activity against weeds and is tolerated well by crop plants, such as, for example, sunflowers.

TABLE B-1

Pre-emergence/greenhouse

| Active compound of Example No. | | Application rate (g of ai./ha) | Maize | Alopecurus | Setaria | Abutilon | Galium |
|---|---|---|---|---|---|---|---|
| 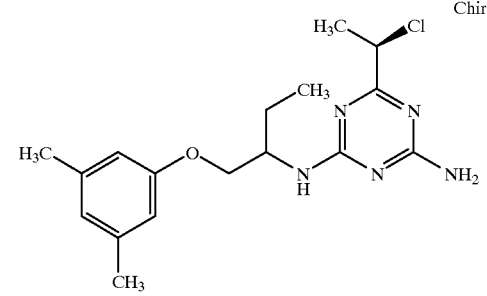 (5) | Chiral | 1000 | 20 | — | 100 | 100 | 100 |
| 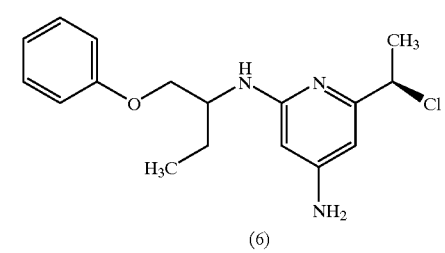 (6) | Chiral | 1000 | 10 | 100 | — | 100 | 100 |

TABLE B-2
Pre-emergence/greenhouse
| Active compound of Example No. | Application rate (g of ai./ha) | Maize | Alopecurus | Setaria | Abutilon | Amaranthus | Sinapis |
|---|---|---|---|---|---|---|---|
| 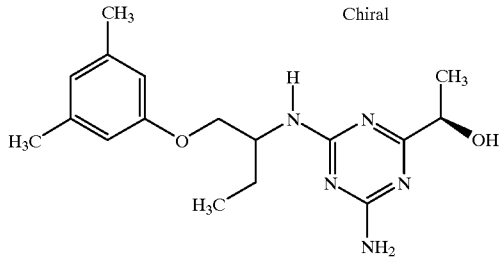 (2) | 1000 | 20 | 100 | 100 | 100 | 80 | — |
| 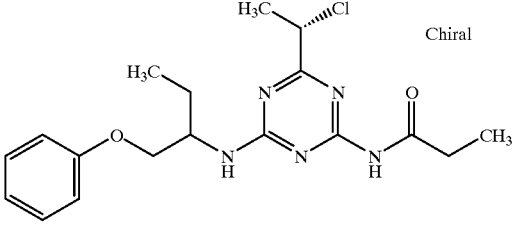 (9) | 1000 | 20 | 95 | — | 95 | 100 | 100 |
TABLE B-3
Pre-emergence/greenhouse
| Active compound of Example No. | Application rate (g of ai./ha) | Alopecurus | Setaria | Abutilon | Amaranthus | Galium | Sinapis |
|---|---|---|---|---|---|---|---|
| 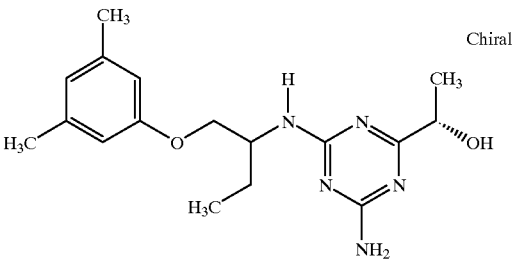 (3) | 2000 | — | 100 | 100 | 100 | 100 | 100 |
| 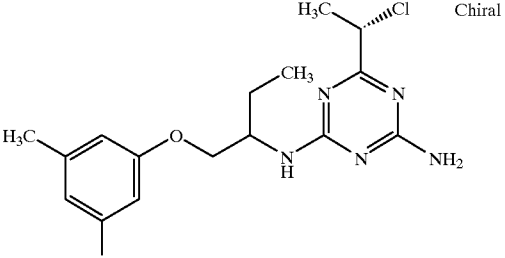 (4) | 2000 | 100 | 100 | 100 | 95 | 100 | 100 |

TABLE B-3-continued
| | | Pre-emergence/greenhouse | | | | | | |
|---|---|---|---|---|---|---|---|---|
| Active compound of Example No. | | Application rate (g of ai./ha) | Alopecurus | Setaria | Abutilon | Amaranthus | Galium | Sinapis |
| 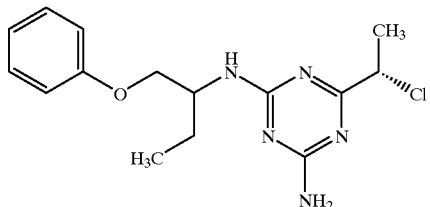 (7) | Chiral | 1000 | 95 | 95 | 100 | 100 | 100 | 100 |
| 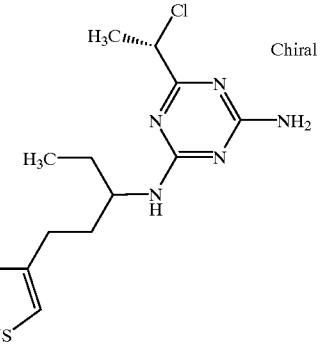 (15) | Chiral | 1000 | 100 | 100 | 100 | 100 | 100 | 100 |
TABLE B-4
| | Pre-emergence/greenhouse | | | | |
|---|---|---|---|---|---|
| Active compound of Example No. | Application rate (g of ai./ha) | Setaria | Abutilon | Galium | Sinapis |
| 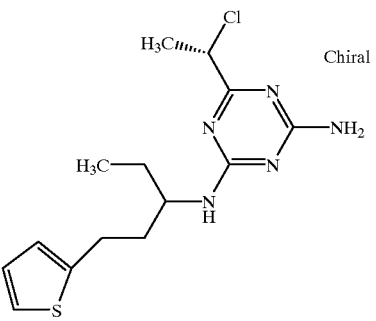 (14) | 1000 | 100 | 100 | 95 | 100 |

TABLE B-5

| | | Pre-emergence/greenhouse | | | | | |
|---|---|---|---|---|---|---|---|
| Active compound of Example No. | Application rate (g of ai./ha) | Alopecurus | Setaria | Abutilon | Galium | Sinapis | Xanthium |
| 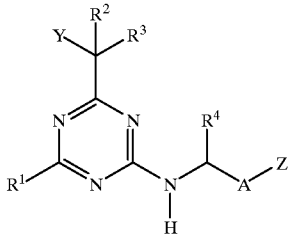 (13) | 1000 | 95 | 100 | 100 | 100 | 95 | 90 |

What is claimed is:

1. A substituted aminotriazine having at least two asymmetrically substituted carbon atoms of the formula (I), (I)

wherein

A represents a single bond, represents dimethylene (ethane-1,2-diyl, —CH$_2$CH$_2$—), oxaethanediyl (—CH$_2$O—) or 2-oxapropane-1,3-diyl (—CH$_2$OCH$_2$—), R$^1$ represents amino, represents formylamino or represents in each case optionally cyano-, fluorine-, chlorine-, methoxy- or ethoxy-substituted acetylamino, propionylamino, methoxycarbonylamino, ethoxycarbonylamino, or dimethylaminomethyleneamino, R$^2$ represents hydrogen, R$^3$ represents methyl, R$^4$ represents methyl or ethyl, Y represents fluorine, and Z represents an optionally substituted phenyl, wherein the substituents are selected from the group consisting of:

hydroxyl, amino, cyano, nitro, carbamoyl, sulphamoyl, fluorine, chlorine, bromine, in each case optionally hydroxyl-, cyano-, fluorine- or chlorine-substituted methyl, ethyl, n- or i-propyl, n-, i-, s- or t-butyl, methoxy, ethoxy, n- or i-propoxy, dimethylamino, in each case optionally fluorine- and/or chlorine-substituted acetyl, methoxycarbonyl, ethoxycarbonyl, dimethylaminocarbonyl, methylthio, ethylthio, n- or i-propylthio, methylsulphinyl, ethylsulphinyl, methylsulphonyl, ethylsulphonyl or dimethylamino-sulphonyl, in each case optionally hydroxyl-, cyano-, nitro-, fluorine-, chlorine-, methyl-, ethyl-, n- or i-propyl-, n-, i-, s- or t-butyl-, trifluoro-methyl-, methoxy-, ethoxy-, n- or i-propoxy-, difluoromethoxy- or trifluoromethoxy-substituted phenyl or phenoxy, and in each case optionally fluorine- and/or chlorinesubstituted methylenedioxy or ethylenedioxy, with the proviso that the substituents at the two carbon atoms to which R$^2$ and R$^3$ or R$^4$ are attached are configured as follows:

(a) R configuration at the carbon atom to which R$^2$ and R$^3$ are attached and R configuration at the carbon atom to which R$^4$ is attached ("R,R-diastereomers"), or (b) R configuration at the carbon atom to which R$^2$ and R$^3$ are attached and S configuration at the carbon atom to which R$^4$ is attached ("R,S-diastereomers").

2. A substituted aminotriazine according to claim 1, wherein A represents a single bond.

3. A substituted aminotriazine according to claim 1, wherein A represents dimethylene (ethane-1,2-diyl, —CH$_2$CH$_2$—), oxaethanediyl (—CH$_2$O—) or 2-oxapropane-1,3-diyl (—CH$_2$OCH$_2$—).

4. A substituted aminotriazine according to claim 1, wherein

R$^1$ represents amino or represents formylamino.

5. A substituted aminotriazine according to claim 1, wherein R$^1$ represents in each case optionally cyano-, fluorine-, chlorine-, methoxy- or ethoxy-substituted acetylamino, propionylamino, methoxycarbonylamino, ethoxycarbonylamino, or dimethylaminomethyleneamino.

6. A substituted aminotriazine according to claim 1, wherein Z represents a substituted phenyl.

7. A herbicidal composition comprising one or more compounds of the formula (I) according to claim 1 and an inert carrier.

8. A method for controlling weeds and undesirable vegetation, comprising applying an effective amount of one or more compounds of the formula (I) according to claim 1 on the weeds or their habitat.

* * * * *